US011446166B2

(12) United States Patent
Clausen et al.

(10) Patent No.: US 11,446,166 B2
(45) Date of Patent: Sep. 20, 2022

(54) PROSTHETIC FOOT WITH REMOVABLE FLEXIBLE MEMBERS

(71) Applicant: Össur Iceland ehf, Reykjavik (IS)

(72) Inventors: Arinbjorn Viggo Clausen, Reykjavik (IS); Bjarni Andresson, Seltjarnarnes (IS); Ragnar Orn Gunnarsson, Reykjavik (IS); Christophe Guy Lecomte, Reykjavik (IS); Maria Gudrun Sveinbjornsdottir, Mosfellsbaer (IS); David Sandahl, Reykjavik (IS); Atli Orn Sverrisson, Reykjavik (IS); David Langlois, Saint-Jacques-de-Leeds (CA)

(73) Assignee: Össur Iceland ehf, Reykjavik (IS)

( * ) Notice: Subject to any disclaimer, the term of this patent is extended or adjusted under 35 U.S.C. 154(b) by 178 days.

(21) Appl. No.: 16/506,306

(22) Filed: Jul. 9, 2019

(65) Prior Publication Data

US 2020/0000611 A1  Jan. 2, 2020

Related U.S. Application Data

(60) Division of application No. 14/704,117, filed on May 5, 2015, now Pat. No. 10,390,974, which is a
(Continued)

(51) Int. Cl.
*A61F 2/66* (2006.01)
*A61F 2/72* (2006.01)
(Continued)

(52) U.S. Cl.
CPC ............. *A61F 2/72* (2013.01); *A61F 2/66* (2013.01); *A61F 2/6607* (2013.01); *A61F 2/74* (2021.08);
(Continued)

(58) Field of Classification Search
CPC .............. A61F 2002/6657–6692; A61F 2002/6614–665
(Continued)

(56) References Cited

U.S. PATENT DOCUMENTS 909,859 A   1/1909  Apgar
2,475,373 A  7/1949  Catranis
(Continued)

FOREIGN PATENT DOCUMENTS

CA  2 546 858   6/2005
CH    543 277  12/1973
(Continued)

OTHER PUBLICATIONS

Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.
(Continued)

*Primary Examiner* — David H Willse
(74) *Attorney, Agent, or Firm* — Knobbe, Martens, Olson & Bear, LLP

(57) ABSTRACT

A prosthetic foot can include an attachment member, at least one first brace, at least one first flexible member, an unpowered actuator, at least one second brace, and at least one second flexible member. The attachment member can include a connector configured to connect the attachment member to a user or another prosthetic device. The at least one first brace can mount to the attachment member and the at least one first flexible member can connect to the attachment member by the at least one first brace such that a force between the ground and the attachment member can be supported by the at least one first flexible member. The unpowered actuator can mount to the attachment member
(Continued)

and the at least one second brace can mounted to the actuator. The at least one second flexible member can connect to the attachment member by the at least one second brace such that a force between the ground and the attachment member can be supported by the at least one second flexible member.

25 Claims, 53 Drawing Sheets

Related U.S. Application Data continuation of application No. 14/683,563, filed on Apr. 10, 2015, now abandoned.

(60) Provisional application No. 61/978,721, filed on Apr. 11, 2014, provisional application No. 62/042,687, filed on Aug. 27, 2014, provisional application No. 62/106,085, filed on Jan. 21, 2015.

(51) Int. Cl.
    *A61F 2/70*     (2006.01)
    *A61F 2/50*     (2006.01)
    *A61F 2/76*     (2006.01)
    *A61F 2/74*     (2006.01)

(52) U.S. Cl.
    CPC ... *A61F 2002/502* (2013.01); *A61F 2002/503* (2013.01); *A61F 2002/5004* (2013.01); *A61F 2002/5006* (2013.01); *A61F 2002/5018* (2013.01); *A61F 2002/5038* (2013.01); *A61F 2002/5069* (2013.01); *A61F 2002/5079* (2013.01); *A61F 2002/6614* (2013.01); *A61F 2002/6657* (2013.01); *A61F 2002/6664* (2013.01); *A61F 2002/6671* (2013.01); *A61F 2002/701* (2013.01); *A61F 2002/764* (2013.01); *A61F 2002/7625* (2013.01); *A61F 2002/7635* (2013.01)

(58) Field of Classification Search
    USPC .......................................................... 623/55
    See application file for complete search history.

(56) References Cited

U.S. PATENT DOCUMENTS

| | | |
|---|---|---|
| 2,568,051 A | 9/1951 | Catranis |
| 3,557,387 A | 1/1971 | Ohlenbusch et al. |
| 3,589,134 A | 6/1971 | Hackmann |
| 3,871,032 A | 3/1975 | Karas |
| 3,953,900 A | 5/1976 | Thompson |
| 3,995,324 A | 12/1976 | Burch |
| 4,030,141 A | 6/1977 | Graupe |
| 4,179,759 A | 12/1979 | Smith |
| 4,209,860 A | 7/1980 | Graupe |
| 4,387,472 A | 6/1983 | Wilson |
| 4,488,320 A | 12/1984 | Wilson |
| 4,518,307 A | 5/1985 | Bloch |
| 4,521,924 A | 6/1985 | Jacobsen et al. |
| 4,558,704 A | 12/1985 | Petrofsky |
| 4,579,558 A | 4/1986 | Ramer |
| 4,600,357 A | 7/1986 | Coules |
| 4,617,920 A | 10/1986 | Carsalade |
| 4,652,266 A | 3/1987 | Truesdell |
| 4,657,470 A | 4/1987 | Clarke et al. |
| 4,776,852 A | 10/1988 | Ruble |
| 4,805,455 A | 2/1989 | DelGiorno et al. |
| 4,843,921 A | 7/1989 | Kremer |
| 4,865,024 A | 9/1989 | Hensley et al. |
| 4,872,803 A | 10/1989 | Asakawa |
| 4,989,161 A | 1/1991 | Oaki |
| 4,994,086 A | 2/1991 | Edwards |
| 5,012,591 A | 5/1991 | Asakawa |
| 5,020,790 A | 6/1991 | Beard et al. |
| 5,062,673 A | 11/1991 | Mimura |
| 5,062,856 A | 11/1991 | Sawamura et al. |
| 5,062,857 A | 11/1991 | Berringer |
| 5,101,472 A | 3/1992 | Repperger |
| 5,116,384 A * | 5/1992 | Wilson ............... A61F 2/66 623/49 |
| 5,156,630 A | 10/1992 | Rappoport et al. |
| 5,174,168 A | 12/1992 | Takagi et al. |
| 5,201,772 A | 4/1993 | Maxwell |
| 5,246,465 A | 9/1993 | Rincoe et al. |
| 5,252,102 A | 10/1993 | Singer et al. |
| 5,252,901 A | 10/1993 | Ozawa et al. |
| 5,282,460 A | 5/1994 | Boldt |
| 5,327,790 A | 7/1994 | Levin et al. |
| 5,376,133 A | 12/1994 | Gramnaes |
| 5,376,138 A | 12/1994 | Bouchard et al. |
| 5,376,141 A | 12/1994 | Phillips |
| 5,383,939 A | 1/1995 | James |
| 5,394,132 A | 2/1995 | Poil |
| 5,413,611 A | 5/1995 | Haslam, II et al. |
| 5,425,780 A | 6/1995 | Flatt et al. |
| 5,430,643 A | 7/1995 | Seraji |
| 5,443,528 A | 8/1995 | Allen |
| 5,455,497 A | 10/1995 | Hirose et al. |
| 5,476,441 A | 12/1995 | Durfee et al. |
| 5,484,389 A | 1/1996 | Stark et al. |
| 5,571,205 A | 11/1996 | James |
| 5,571,213 A | 11/1996 | Allen |
| 5,650,704 A | 7/1997 | Pratt et al. |
| 5,662,693 A | 9/1997 | Johnson et al. |
| 5,695,527 A | 12/1997 | Allen |
| 5,704,946 A | 1/1998 | Greene |
| 5,746,774 A | 5/1998 | Kramer |
| 5,779,735 A | 7/1998 | Molino |
| 5,800,561 A | 9/1998 | Rodriquez |
| 5,800,570 A | 9/1998 | Collier |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Connor |
| 5,929,332 A | 7/1999 | Brown |
| 5,948,021 A | 9/1999 | Radcliffe |
| 5,954,621 A | 9/1999 | Joutras et al. |
| 5,957,981 A | 9/1999 | Gramnaes |
| 5,984,972 A | 11/1999 | Huston et al. |
| 6,007,582 A | 12/1999 | May |
| 6,029,374 A | 2/2000 | Herr et al. |
| 6,061,577 A | 5/2000 | Andrieu et al. |
| 6,071,313 A * | 6/2000 | Phillips ............... A61F 2/66 623/55 |
| 6,086,616 A | 7/2000 | Okuda et al. |
| 6,091,977 A | 7/2000 | Tarjan et al. |
| 6,113,642 A | 9/2000 | Petrofsky et al. |
| 6,117,177 A | 9/2000 | Chen et al. |
| 6,122,960 A | 9/2000 | Hutchings et al. |
| 6,129,766 A | 10/2000 | Johnson et al. |
| 6,187,052 B1 | 2/2001 | Molino et al. |
| 6,206,932 B1 | 3/2001 | Johnson |
| 6,206,933 B1 | 3/2001 | Shorter et al. |
| 6,361,570 B1 | 3/2002 | Gow |
| 6,378,190 B2 | 4/2002 | Akeel |
| 6,379,393 B1 | 4/2002 | Mavroidis et al. |
| 6,423,098 B1 | 7/2002 | Biedermann |
| 6,425,925 B1 | 7/2002 | Grundei |
| 6,436,149 B1 | 8/2002 | Rincoe |
| 6,443,993 B1 | 9/2002 | Koniuk |
| 6,482,236 B2 | 11/2002 | Habecker |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,858 B1 | 2/2003 | Le Moel et al. |
| 6,522,266 B1 | 2/2003 | Soehren et al. |
| 6,543,987 B2 | 4/2003 | Ehrat |
| 6,587,728 B2 | 7/2003 | Fang et al. |

(56) References Cited

U.S. PATENT DOCUMENTS

| | | |
|---|---|---|
| 6,610,101 B2 | 8/2003 | Herr et al. |
| 6,613,097 B1 | 9/2003 | Cooper |
| 6,645,252 B2 | 11/2003 | Asai et al. |
| 6,679,920 B2 | 1/2004 | Biedermann et al. |
| 6,695,885 B2 | 2/2004 | Schulman et al. |
| 6,704,024 B2 | 3/2004 | Robotham et al. |
| 6,704,582 B2 | 3/2004 | Le-Faucheur et al. |
| 6,708,103 B2 | 3/2004 | Herr et al. |
| 6,719,807 B2 | 4/2004 | Harris |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,764,521 B2 | 7/2004 | Molino et al. |
| 6,767,370 B1 | 7/2004 | Mosler et al. |
| 6,813,582 B2 | 11/2004 | Levi et al. |
| 6,824,569 B2 | 11/2004 | Okediji |
| 6,863,695 B2 | 3/2005 | Doddroe et al. |
| 6,875,241 B2 | 4/2005 | Christensen |
| 6,908,488 B2 | 6/2005 | Paasivaara et al. |
| 6,910,331 B2 | 6/2005 | Asai et al. |
| 6,955,692 B2 | 10/2005 | Grundei |
| 6,966,882 B2 | 11/2005 | Horst |
| 6,969,408 B2 | 11/2005 | Lecomte et al. |
| 7,029,500 B2 | 4/2006 | Martin |
| 7,066,896 B1 | 6/2006 | Kiselik |
| 7,066,964 B2 | 6/2006 | Wild |
| 7,112,938 B2 | 9/2006 | Takenaka et al. |
| 7,118,601 B2 | 10/2006 | Yasui |
| 7,131,998 B2 | 11/2006 | Pasolini |
| 7,137,998 B2 | 11/2006 | Bédard |
| 7,147,667 B2 | 12/2006 | Bédard |
| 7,150,762 B2 | 12/2006 | Caspers |
| 7,164,967 B2 | 1/2007 | Etienne-Cummings et al. |
| 7,182,738 B2 | 2/2007 | Bonutti et al. |
| 7,209,788 B2 | 4/2007 | Nicolelis et al. |
| 7,279,009 B2 | 10/2007 | Herr et al. |
| 7,295,892 B2 | 11/2007 | Herr et al. |
| 7,300,240 B2 | 11/2007 | Brogardh |
| 7,308,333 B2 | 12/2007 | Kern et al. |
| 7,313,463 B2 | 12/2007 | Herr et al. |
| 7,314,490 B2 | 1/2008 | Bédard et al. |
| 7,347,877 B2 | 3/2008 | Clausen et al. |
| 7,381,192 B2 | 6/2008 | Brodard et al. |
| 7,396,337 B2 | 7/2008 | McBean et al. |
| 7,410,471 B1 | 8/2008 | Campbell et al. |
| 7,410,472 B2 | 8/2008 | Yakimovich et al. |
| 7,455,696 B2 | 11/2008 | Bisbee, III et al. |
| 7,462,201 B2 | 12/2008 | Christensen |
| 7,485,152 B2 | 2/2009 | Haynes et al. |
| 7,520,904 B2 | 4/2009 | Christensen |
| 7,531,006 B2 | 5/2009 | Clausen et al. |
| 7,552,664 B2 | 6/2009 | Bulatowicz |
| 7,575,602 B2 | 8/2009 | Amirouche et al. |
| 7,578,799 B2 | 8/2009 | Thorsteinsson et al. |
| 7,588,604 B2 | 9/2009 | Okuda |
| 7,618,464 B2 | 11/2009 | Christensen |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,704,283 B2 | 4/2010 | Ninomiya |
| 7,731,759 B2 | 6/2010 | Pusch et al. |
| 7,736,394 B2 | 6/2010 | Bédard et al. |
| 7,799,091 B2 | 9/2010 | Herr et al. |
| 7,811,333 B2 | 10/2010 | Jónsson et al. |
| 7,811,334 B2 | 10/2010 | Ragnarsdottir et al. |
| 7,815,689 B2 | 10/2010 | Bédard et al. |
| 7,846,213 B2 | 12/2010 | Lecomte et al. |
| 7,867,284 B2 | 1/2011 | Bédard |
| 7,918,808 B2 | 4/2011 | Simmons |
| 7,942,935 B2 | 5/2011 | Iversen et al. |
| 7,955,398 B2 | 6/2011 | Bédard et al. |
| 7,985,265 B2 | 7/2011 | Moser et al. |
| 7,992,849 B2 | 8/2011 | Sugar et al. |
| 8,011,229 B2 | 9/2011 | Lieberman et al. |
| 8,048,007 B2 | 11/2011 | Roy |
| 8,048,172 B2 | 11/2011 | Jonsson et al. |
| 8,057,550 B2 | 11/2011 | Clausen |
| 8,075,633 B2 | 12/2011 | Herr et al. |
| 8,083,807 B2 | 12/2011 | Auberger et al. |
| 8,087,498 B2 | 1/2012 | Dupuis et al. |
| 8,109,890 B2 | 2/2012 | Kamiar et al. |
| 8,142,370 B2 | 3/2012 | Weinberg et al. |
| 8,231,687 B2 | 7/2012 | Bédard et al. |
| 8,323,354 B2 | 12/2012 | Bédard et al. |
| 8,366,788 B2 | 2/2013 | Moser et al. |
| 8,403,997 B2 | 3/2013 | Sykes et al. |
| 8,419,804 B2 | 4/2013 | Herr et al. |
| 8,435,309 B2 | 5/2013 | Gilbert et al. |
| 8,480,760 B2 | 7/2013 | Hansen et al. |
| 8,500,823 B2 | 8/2013 | Herr et al. |
| 8,512,415 B2 | 8/2013 | Herr et al. |
| 8,551,184 B1 | 10/2013 | Herr |
| 7,431,737 C1 | 12/2013 | Ragnarsdottir et al. |
| 8,601,897 B2 | 12/2013 | Lauzier et al. |
| 8,617,254 B2 | 12/2013 | Bisbee, III et al. |
| 8,652,218 B2 | 2/2014 | Goldfarb et al. |
| 8,657,886 B2 | 2/2014 | Clausen et al. |
| 8,702,811 B2 | 4/2014 | Ragnarsdottir et al. |
| 7,896,927 C1 | 5/2014 | Clausen et al. |
| 8,764,850 B2 | 7/2014 | Hanset et al. |
| 8,790,282 B2 | 7/2014 | Jung et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,864,846 B2 | 10/2014 | Herr et al. |
| 8,870,967 B2 | 10/2014 | Herr et al. |
| 8,888,864 B2 | 11/2014 | Iversen et al. |
| 8,915,968 B2 | 12/2014 | Langlois et al. |
| 8,986,397 B2 | 3/2015 | Bédard et al. |
| 9,032,635 B2 | 5/2015 | Herr et al. |
| 9,044,346 B2 | 6/2015 | Langlois et al. |
| 9,060,883 B2 | 6/2015 | Herr et al. |
| 9,060,884 B2 | 6/2015 | Langlois |
| 9,066,819 B2 | 6/2015 | Gramnaes |
| 9,078,774 B2 | 7/2015 | Jónsson et al. |
| 9,114,029 B2 | 8/2015 | Ásgeirsson et al. |
| 9,221,177 B2 | 12/2015 | Herr et al. |
| 9,271,851 B2 | 3/2016 | Claussen et al. |
| 9,289,316 B2 | 3/2016 | Ward et al. |
| 9,345,591 B2 | 5/2016 | Bisbee, III et al. |
| 9,345,592 B2 | 5/2016 | Herr et al. |
| 9,351,856 B2 | 5/2016 | Herr et al. |
| 9,358,137 B2 | 6/2016 | Bédard et al. |
| 9,459,698 B2 | 10/2016 | Lee |
| 9,462,966 B2 | 10/2016 | Clausen et al. |
| 9,498,401 B2 | 11/2016 | Herr et al. |
| 9,526,635 B2 | 12/2016 | Gilbert et al. |
| 9,526,636 B2 | 12/2016 | Bédard et al. |
| 9,532,877 B2 | 1/2017 | Holgate |
| 9,554,922 B2 | 1/2017 | Casler et al. |
| 9,561,118 B2 | 2/2017 | Clausen et al. |
| 9,604,368 B2 | 3/2017 | Holgate |
| 9,622,884 B2 | 4/2017 | Holgate et al. |
| 9,649,206 B2 | 5/2017 | Bédard |
| 9,682,005 B2 | 6/2017 | Herr et al. |
| 9,687,377 B2 | 6/2017 | Han et al. |
| 9,707,104 B2 | 7/2017 | Clausen |
| 9,717,606 B2 | 8/2017 | Gramnaes |
| 9,737,419 B2 | 8/2017 | Herr et al. |
| 9,808,357 B2 | 11/2017 | Langlois |
| 9,839,552 B2 | 12/2017 | Han et al. |
| 9,895,240 B2 | 2/2018 | Langlois et al. |
| 10,195,057 B2 | 2/2019 | Clausen |
| 10,251,762 B2 | 4/2019 | Langlois |
| 10,299,943 B2 | 5/2019 | Clausen et al. |
| 10,307,271 B2 | 6/2019 | Holgate et al. |
| 10,369,019 B2 | 8/2019 | Clausen et al. |
| 10,390,974 B2 | 8/2019 | Clausen et al. |
| 10,405,996 B2 | 9/2019 | Langlois |
| 10,543,109 B2 | 1/2020 | Holgate |
| 10,575,970 B2 | 3/2020 | Holgate |
| 10,695,197 B2 | 6/2020 | Clausen |

(56) References Cited

U.S. PATENT DOCUMENTS

| | | | |
|---|---|---|---|
| 10,940,027 B2 | 3/2021 | Langlois et al. |
| 11,007,072 B2 | 5/2021 | Gilbert et al. |
| 2001/0002772 A1 | 6/2001 | Kim et al. |
| 2002/0007690 A1 | 1/2002 | Song et al. |
| 2002/0079857 A1 | 6/2002 | Ishii et al. |
| 2003/0005786 A1 | 1/2003 | Stuart et al. |
| 2003/0120354 A1 | 6/2003 | Doddroe et al. |
| 2004/0064195 A1 | 4/2004 | Herr |
| 2004/0073149 A1 | 4/2004 | Okediji |
| 2004/0078299 A1 | 4/2004 | Down-Logan et al. |
| 2004/0153484 A1 | 8/2004 | Unno |
| 2004/0169112 A1 | 9/2004 | Grossart |
| 2004/0217324 A1 | 11/2004 | Hsu et al. |
| 2005/0049719 A1 | 3/2005 | Wilson |
| 2005/0049721 A1 | 3/2005 | Sulprizio |
| 2005/0070834 A1 | 3/2005 | Herr et al. |
| 2005/0107889 A1 | 5/2005 | Bédard et al. |
| 2005/0113973 A1 | 5/2005 | Endo et al. |
| 2005/0137717 A1 | 6/2005 | Gramnaes |
| 2005/0166685 A1 | 8/2005 | Boiten |
| 2005/0216097 A1 | 9/2005 | Rifkin |
| 2005/0251079 A1 | 11/2005 | Carvey et al. |
| 2005/0283257 A1 | 12/2005 | Bisbee et al. |
| 2006/0025959 A1 | 2/2006 | Gomez et al. |
| 2006/0069336 A1 | 3/2006 | Krebs et al. |
| 2006/0122710 A1 | 6/2006 | Bédard et al. |
| 2006/0184280 A1 | 8/2006 | Oddsson et al. |
| 2006/0189899 A1 | 8/2006 | Flaherty et al. |
| 2006/0206043 A1 | 9/2006 | Yakimovich et al. |
| 2006/0224246 A1 | 10/2006 | Clausen et al. |
| 2006/0249315 A1 | 11/2006 | Herr et al. |
| 2006/0259153 A1 | 11/2006 | Harn et al. |
| 2006/0260620 A1 | 11/2006 | Kazerooni et al. |
| 2007/0043449 A1 | 2/2007 | Herr et al. |
| 2007/0061016 A1 | 3/2007 | Kuo et al. |
| 2007/0083272 A1 | 4/2007 | Van De Veen |
| 2007/0123997 A1 | 5/2007 | Herr et al. |
| 2007/0129653 A1 | 6/2007 | Sugar et al. |
| 2007/0162152 A1 | 7/2007 | Herr et al. |
| 2008/0004718 A1 | 1/2008 | Mosler |
| 2008/0046096 A1 | 2/2008 | Bédard et al. |
| 2008/0058668 A1 | 3/2008 | Seyed Momen et al. |
| 2008/0141813 A1 | 6/2008 | Rat |
| 2008/0262635 A1 | 10/2008 | Moser et al. |
| 2008/0306612 A1 | 12/2008 | Mosler |
| 2009/0030530 A1 | 1/2009 | Martin |
| 2009/0082869 A1 | 3/2009 | Slemker et al. |
| 2009/0088912 A1 | 4/2009 | Rajaraman |
| 2009/0192625 A1 | 7/2009 | Boiten |
| 2009/0204229 A1 | 8/2009 | Mosley et al. |
| 2009/0204230 A1 | 8/2009 | Kattenborn et al. |
| 2010/0023133 A1 | 1/2010 | Fairbanks et al. |
| 2010/0030343 A1 | 2/2010 | Hansen et al. |
| 2010/0042228 A1 | 2/2010 | Doddroe et al. |
| 2010/0094431 A1 | 4/2010 | Albrecht-Laatsch |
| 2010/0113980 A1 | 5/2010 | Herr et al. |
| 2010/0114329 A1 | 5/2010 | Casler et al. |
| 2010/0131101 A1 | 5/2010 | Engeberg et al. |
| 2010/0161077 A1 | 6/2010 | Boone et al. |
| 2010/0174384 A1 | 7/2010 | Herr et al. |
| 2010/0185301 A1 | 7/2010 | Hansen et al. |
| 2010/0241242 A1 | 9/2010 | Herr et al. |
| 2010/0262260 A1 | 10/2010 | Bédard et al. |
| 2010/0275718 A1 | 11/2010 | Stuart et al. |
| 2010/0305716 A1 | 12/2010 | Pusch et al. |
| 2010/0324456 A1 | 12/2010 | Jónsson et al. |
| 2010/0324699 A1 | 12/2010 | Herr et al. |
| 2011/0015761 A1 | 1/2011 | Celebi et al. |
| 2011/0082566 A1 | 4/2011 | Herr et al. |
| 2011/0087339 A1 | 4/2011 | Pusch et al. |
| 2011/0106274 A1 | 5/2011 | Ragnarsdottir et al. |
| 2011/0125290 A1 | 5/2011 | Langlois |
| 2011/0130847 A1 | 6/2011 | Bédard et al. |
| 2011/0132131 A1 | 6/2011 | Worz |
| 2011/0137429 A1 | 6/2011 | Bédard et al. |
| 2011/0166674 A1 | 7/2011 | Montmartin |
| 2011/0196509 A1 | 8/2011 | Jansen et al. |
| 2011/0202144 A1 | 8/2011 | Palmer et al. |
| 2011/0208322 A1 | 8/2011 | Rifkin et al. |
| 2011/0224804 A1 | 9/2011 | Clausen et al. |
| 2011/0295384 A1 | 12/2011 | Herr et al. |
| 2011/0295385 A1 | 12/2011 | Herr et al. |
| 2012/0016492 A1 | 1/2012 | Clausen |
| 2012/0078415 A1 | 3/2012 | Kubo et al. |
| 2012/0130508 A1 | 5/2012 | Harris et al. |
| 2012/0203359 A1 | 8/2012 | Schimmels et al. |
| 2012/0209405 A1 | 8/2012 | Herr et al. |
| 2012/0226364 A1 | 9/2012 | Kampas et al. |
| 2012/0259430 A1 | 10/2012 | Han et al. |
| 2012/0283845 A1 | 11/2012 | Herr et al. |
| 2012/0330439 A1 | 12/2012 | Goldfarb et al. |
| 2013/0035769 A1 | 2/2013 | Bédard et al. |
| 2013/0142608 A1 | 6/2013 | Zhang et al. |
| 2013/0144402 A1 | 6/2013 | Clausen et al. |
| 2013/0173022 A1 | 7/2013 | Arabian et al. |
| 2013/0197408 A1 | 8/2013 | Goldfarb et al. |
| 2013/0204395 A1 | 8/2013 | Gramnaes |
| 2013/0218295 A1 | 8/2013 | Holgate et al. |
| 2013/0218298 A1 | 8/2013 | Mosler |
| 2013/0268093 A1 | 10/2013 | Gilbert et al. |
| 2013/0282141 A1 | 10/2013 | Herr et al. |
| 2013/0297041 A1 | 11/2013 | Bédard |
| 2013/0310949 A1 | 11/2013 | Goldfarb et al. |
| 2014/0039642 A1* | 2/2014 | Nijiman .................. A61F 2/66 623/33 |
| 2014/0081424 A1 | 3/2014 | Herr et al. |
| 2014/0114437 A1 | 4/2014 | Herr et al. |
| 2014/0121782 A1 | 5/2014 | Herr et al. |
| 2014/0156025 A1 | 6/2014 | Bisbee, III et al. |
| 2014/0191522 A1 | 7/2014 | Birglen |
| 2014/0243997 A1 | 8/2014 | Clausen et al. |
| 2014/0277586 A1 | 9/2014 | Clausen |
| 2015/0032225 A1 | 1/2015 | Oddsson et al. |
| 2015/0073566 A1 | 3/2015 | Ragnarsdottir et al. |
| 2015/0127118 A1 | 5/2015 | Herr et al. |
| 2015/0164661 A1 | 6/2015 | Ragnarsdottir et al. |
| 2015/0209214 A1 | 7/2015 | Herr et al. |
| 2015/0223952 A1 | 8/2015 | Langlois |
| 2015/0265429 A1 | 9/2015 | Jónsson et al. |
| 2015/0297368 A1 | 10/2015 | Langlois |
| 2016/0158031 A1 | 6/2016 | Ward et al. |
| 2016/0158032 A1 | 6/2016 | Ward et al. |
| 2016/0302956 A1 | 10/2016 | Gilbert et al. |
| 2017/0049659 A1 | 2/2017 | Farris et al. |
| 2017/0112640 A1 | 4/2017 | Clausen et al. |
| 2017/0241497 A1 | 8/2017 | Mooney et al. |
| 2017/0304083 A1 | 10/2017 | Clausen |
| 2017/0340504 A1 | 11/2017 | Sanz Merodio et al. |
| 2018/0125678 A1 | 5/2018 | Langlois |
| 2018/0177618 A1 | 6/2018 | Langlois |
| 2019/0175369 A1 | 6/2019 | Langlois |
| 2019/0224026 A1 | 7/2019 | Clausen |
| 2019/0365545 A1 | 12/2019 | Langlois |
| 2020/0214856 A1 | 7/2020 | Holgate |
| 2020/0383804 A1 | 12/2020 | Clausen |

FOREIGN PATENT DOCUMENTS

| | | |
|---|---|---|
| CN | 2043873 U | 9/1989 |
| CN | 1215614 | 5/1999 |
| CN | 2400072 Y | 10/2000 |
| CN | 1088988 | 8/2002 |
| CN | 2776340 | 5/2006 |
| CN | 1929797 | 3/2007 |
| DE | 39 23 057 | 1/1991 |
| DE | 43 05 213 | 8/1993 |
| DE | 42 29 330 | 3/1994 |
| DE | 692 26 268 | 4/1999 |
| EP | 0 358 056 | 3/1990 |
| EP | 0 380 060 | 8/1990 |
| EP | 1 166 726 | 1/2002 |
| EP | 1 169 982 | 1/2002 |
| EP | 1 410 780 | 4/2004 |
| EP | 1 442 704 | 8/2004 |

(56) References Cited

FOREIGN PATENT DOCUMENTS

| EP | 1 547 567 | 6/2005 |
|---|---|---|
| EP | 1 718 252 | 11/2006 |
| EP | 1 792 597 | 6/2007 |
| EP | 2 564 817 | 3/2013 |
| EP | 2 702 963 | 3/2014 |
| FR | 2293 185 | 7/1976 |
| FR | 2 623 086 | 5/1989 |
| FR | 2 816 463 | 5/2002 |
| GB | 2 201 260 | 8/1988 |
| GB | 2 228 201 | 8/1990 |
| GB | 2 260 495 | 4/1993 |
| GB | 2 301 776 | 12/1996 |
| GB | 2 302 949 | 2/1997 |
| GB | 2 367 753 | 4/2002 |
| JP | 59-032453 | 2/1984 |
| JP | 59-071747 | 4/1984 |
| JP | 59-088147 | 5/1984 |
| JP | 59-189843 | 10/1984 |
| JP | 60-177102 | 9/1985 |
| JP | 01-244748 | 9/1989 |
| JP | 05-123348 | 5/1993 |
| JP | 05-161668 | 6/1993 |
| JP | 07-024766 | 1/1995 |
| JP | 11-056885 | 3/1999 |
| JP | 11-215793 | 8/1999 |
| JP | 2002-191654 | 7/2002 |
| JP | 2005-500 | 1/2005 |
| JP | 2005-536317 | 12/2005 |
| JP | 2009-153660 | 7/2009 |
| KR | 2002-0041137 | 6/2002 |
| KR | 10-2006-105026 | 10/2006 |
| SU | 1447366 | 12/1988 |
| SU | 1731210 | 5/1992 |
| WO | WO 94/009727 | 5/1994 |
| WO | WO 96/041599 | 12/1996 |
| WO | WO 97/027822 | 8/1997 |
| WO | WO 00/027318 | 5/2000 |
| WO | WO 03/003953 | 1/2003 |
| WO | WO 03/088373 | 10/2003 |
| WO | WO 2004/017873 | 3/2004 |
| WO | WO 2004/017890 | 3/2004 |
| WO | WO 2005/079712 | 9/2005 |
| WO | WO 2006/076164 | 7/2006 |
| WO | WO 2006/088966 | 8/2006 |
| WO | WO 2007/025116 | 3/2007 |
| WO | WO 2007/095933 | 8/2007 |
| WO | WO 2008/080231 | 7/2008 |
| WO | WO 2010/027968 | 3/2010 |
| WO | WO 2011/005482 | 1/2011 |
| WO | WO 2011/096965 | 8/2011 |
| WO | WO 2012/091555 | 7/2012 |
| WO | WO 2013/006585 | 1/2013 |
| WO | WO 2013/0148726 | 10/2013 |
| WO | WO 2015/157723 | 10/2015 |

OTHER PUBLICATIONS

Aminian et al., "Estimation of Speed and Incline of Walking Using Neural Network," IEEE Transactions on Instrumentation and Measurement, vol. 44, No. 3, Jun. 1995, pp. 743-746.
Andrews et al., "Hybrid FES Orthosis Incorporating Closed Loop Control and Sensory Feedback," Journal of Biomedical Engineering, vol. 10, Apr. 1988, pp. 189-195.
Bar et al., "Adaptive Microcomputer Control of an Artificial Knee in Level Walking," Journal of Biomechanical Engineering, vol. 5, Apr. 1983, pp. 145-150.
Blaya, "Force-Controllable Ankle Foot Orthosis (AFO) to Assist Drop Foot Gait," Massachusetts Institute of Technology, Thesis, Feb. 2003 (believed to be catalogued on or after Jul. 8, 2003) in 97 pages.
Bonivento et al., "Automatic Tuning of Myoelectric Prostheses", Journal of Rehabilitation Research and Development, Jul. 1998, vol. 35, No. 3, pp. 294-304.
Dai et al., "Application of Tilt Sensors in Functional Electrical Stimulation," IEEE Transactions on Rehabilitation Engineering, vol. 4, No. 2, Jun. 1996, pp. 63-72.
Dietl et al., "Der Einsatz von Elektronik bei Prothesen zur Versorgung der unteren Extremität," Med. Orth. Tech., vol. 117, 1997, pp. 31-35.
DIGINFO TV, "Powered Prosthetic Thigh and Leg", uploaded Nov. 7, 2008 http://www.youtube.com/watch?v=lqitTzNEd54&feature=youtu.be%3E [Sc14704117reenshots retrieved Oct. 23, 2014 in 9 pages].
"Extension Spring Design Theory, Spring Rate of Extension Springs," http://web.archive.org/web/20131209120508/http://springipedia.com/extension-design-theory.asp as archived Dec. 9, 2013 in 1 page.
Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.
Foerster et al., "Detection of Posture and Motion by Accelerometry: A Validation Study in Ambulatory Monitoring," Computers in Human Behavior, vol. 15, 1999, pp. 571-583.
Frank et al., "Reliable Real-Time Recognition of Motion Related Human Activities Using MEMS Inertial Sensors," 2010, http://www.xsens.com/images/stories/PDF/Activity_Recognition_Final_ION_2010_Paper.pdf.
Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.
Herr et al., "Patient-Adaptive Prosthetic and Orthotic Leg Systems," In Proceedings of the 12th Nordic Baltic Conference on Biomedical Engineering and Medical Physics, Jun. 2002, pp. 4.
Heyn et al., "The Kinematics of the Swing Phase Obtained From Accelerometer and Gyroscope Measurements," 18th Annual International Conference of the IEEE Engineering in Medicine and Biology Society, Amsterdam 1996, pp. 463-464.
International Preliminary Report on Patentability and Written Opinion in PCT Application No. PCT/US2015/025461, dated Oct. 12, 2016.
International Search Report and Written Opinion in PCT Application No. PCT/US2015/025461, dated Sep. 2, 2015.
Invitation to Pay Additional Fees in PCT Application No. PCT/US2015/025461, dated Jun. 29, 2015.
Jonic et al., "Three Machine Learning Techniques for Automatic Determination of Rules to Control Locomotion," IEEE, Transactions on Biomedical Engineering, vol. 46, No. 3, Mar. 1999, pp. 300-310.
Kirkwood et al., "Automatic Detection of Gait Events: A Case Study Using Inductive Learning Techniques," Journal of Biomedical Engineering, vol. 11, Nov. 1989, pp. 511-516.
Kostov et al., "Machine Learning in Control of Functional Electrical Stimulation Systems for Locomotion," IEEE Transactions on Biomedical Engineering, vol. 42, No. 6, Jun. 1995, pp. 541-551.
Lee et al., "Activity and Location Recognition Using Wearable Sensors," Pervasive Computing, Jul.-Sep. 2002, pp. 24-32.
Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12. Asserted by iWalk in Civil Action No. 12-CV-11061 FDS to constitute prior art to U.S. Patent Nos. 7,431,737 and 7,896,927. Applicant requests that the Examiner consider this reference as qualifying as prior art to the present application, but reserves the right to challenge the reference's prior art status at a later date.
Martin, C.W., Otto Bock C-leg: A Review of Its Effectiveness, WCB Evidence Based Group, Nov. 27, 2003.
Martinez-Villalpando et al., "Agonist-Antagonist Active Knee Prosthesis: A Preliminary Study in Level-Ground Walking", Journal of Rehabilitation Research & Development, 2009, vol. 46, No. 3, pp. 361-373.
Mayagoitia et al., "Accelerometer and Rate Gyroscope Measurement of Kinematics: An Inexpensive Alternative to Optical Motion Analysis Systems," Journal of Biomechanics, vol. 35, 2002, pp. 537-542.

(56) References Cited

OTHER PUBLICATIONS

Michael, John W., M.Ed., "Upper Limb Powered Components and Controls: Current Concepts", Clinical Prosthetics and Orthotics, 1986, vol. 10, No. 2, pp. 66-77.
Moe-Nilssen, R.; "A New Method for Evaluating Motor Control in Gait Under Real-Life Environmental Conditions. Part 1: The Instrument" Clinical Biomechanics, vol. 13, 1998, pp. 320-327.
Moe-Nilssen, R.; "A New Method for Evaluating Motor Control in Gait Under Real-Life Environmental Conditions. Part 2: Gait Analysis" Clinical Biomechanics, vol. 13, 1998, pp. 328-335.
Nakagawa, Akio; "Intelligent Knee Mechanism and the Possibility to Apply the Principle to the Other Joints," Proceedings of the 20th Annual International Conference of the IEEE Engineering in Medicine and Biology Society, vol. 20, No. 5, Dec. 1998, pp. 2282-2287.
Petrofsky et al., "Feedback Control System for Walking in Man," Computers in Biology and Medicine, vol. 14, No. 2, pp. 135-149, 1984.
Popovic et al., "Control Aspects of Active Above-Knee Prosthesis," International Journal of Man-Machine Studies, vol. 35, No. 6, Dec. 1991, pp. 751-767.
Reitman et al., "Gait Analysis in Prosthetics: Opinions, Ideas, and Conclusions," Prosthetics and Orthotics International, vol. 26, 2002, 50-57.
Robinson et al., "Series Elastic Actuator Development for a Biomimetic Walking Robot," MIT Leg Laboratory, 1999, pp. 1-8.
Sekine et al., "Classification of Waist-Acceleration Signals in a Continuous Walking Record," Medical Engineering & Physics, 2000, pp. 285-291.
Sigurdsson et al., "12th Nordic Baltic Conference on Biomedical Engineering and Medical Physics," Proceeding of the International Federation for Medical & Biological Engineering, Jun. 18-22, 2002, Reykjavik, Iceland, pp. 6.
Smidt et al., "An Automated Accelerometry System for Gait Analysis," Journal of Biomechanics, vol. 10, 1977, pp. 367-375.
"The Electronic C-Leg® Knee Joint System," Instructions for Use, Otto Bock®, 2002, pp. 30. http://www.ottobockus.com/products/lower_limb_prosthetics/c-leg_instructions.pdf (printed Jul. 20, 2006) Asserted by iWalk in Civil Action No. 12-CV-11061 FDS to constitute prior art to U.S. Patent Nos. 7,431,737 and 7,896,927. Applicant requests that the Examiner to consider this reference as qualifying as prior art to the present application, but reserves the right to challenge the reference's prior art status at a later date.
Tomović et al., "A Finite State Approach to the Synthesis of Bioengineering Control Systems," IEEE Transactions of Human Factors in Electronics, vol. HFE-7, No. 2, Jun. 1966, pp. 65-69.
Tong et al., "A Practical Gait Analysis System Using Gyroscopes," Medical Engineering and Physics, vol. 21, 1999, pp. 87-94.
Tong et al., "Virtual Artificial Sensor Technique for Functional Electrical Stimulation," Medical Engineering & Physics, vol. 20, 1998, pp. 458-468.
Townsend et al., "Biomechanics and Modeling of Bipedal Climbing and Descending," Journal of Biomechanics, vol. 9, No. 4, 1976, pp. 227-239.
Van Der Kooij et al., "A Multisensory Integration Model of Human Stance Control," Biological Cybernetics, vol. 80, pp. 299-308, 1998.
Veltink et al., "Detection of Static and Dynamic Activities using Uniaxial Accelerometers," IEEE Transactions on Rehabilitation Engineering, vol. 4, No. 4, Dec. 1996, pp. 375-385.
Veltink et al., "The Feasibility of Posture and Movement Detection by Accelerometry," 15th Annual International Conference of the IEEE Engineering in Medicine and Biology Society, Oct. 28-31, 1993, San Diego, California, pp. 1230-1231.
Willemsen et al., "Real-Time Gait Assessment Utilizing a New Way of Accelerometry," Journal of Biomechanics, vol. 23, No. 8, 1990. pp. 859-863.
Woodward et al., "Skeletal Accelerations Measured During Different Exercises," Proceedings of the Institution of Mechanical Engineers, Part H, Journal of Engineering in Medicine, vol. 207, No. 2, Jun. 1993, pp. 79-85.
Official Communication in European Application No. 15776980.3, dated Oct. 27, 2017.
Hanafusa et al., "A Robot Hand with Elastic Fingers and Its Application to Assembly Process," Robot Motion, Brady et al., MIT Press, Cambridge, MA, 1982, pp. 337-359.
Hashimoto et al., "An Instrumented Compliant Wrist Using a Parallel Mechanism," Japan/USA Symposium on Flexible Automation, vol. 1, ASME, 1992, pp. 741-744.
Howard, Russell Duane; "Joint and Actuator Design for Enhanced Stability in Robotic Force Control," Massachusetts Institute of Technology, Thesis, Sep. 1990 (believed to be catalogued on or after Sep. 19, 1990) in 219 pages.
Pfeffer et al., "Experiments with a Dual-Armed, Cooperative, Flexible-Drivetrain Robot System," Proceedings of 1993 IEEE International Conference on Robotics and Automation, vol. 3, May 5, 1993, pp. 601-608.
Rapport De Recherche Europeenne EP 01169982, dated Nov. 6, 2001.
Robinson, David William; "Design and Analysis of Series Elasticity in Closed-Loop Actuator Force Control," Massachusetts Institute of Technology, Thesis, Jun. 2000 in 123 pages.
Sugano et al., "Force Control of the Robot Finger Joint Equipped with Mechanical Compliance Adjuster," Proceedings of the 1992 IEEE/RSJ International Conference on Intelligent Robots & Systems, Jul. 7-10, 1992, pp. 2005-2013.
Williamson, Matthew M.; "Series Elastic Actuators," Massachusetts Institute of Technology Artificial Intelligence Laboratory, A.I. Technical Report No. 1524, Jan. 1995, pp. 1-83.
Official Communication in Chinese Patent Application No. 201580026745.8, dated Mar. 6, 2019.
Official Communication in Chinese Patent Application No. 201580026745.8, dated Jul. 23, 2019.

* cited by examiner

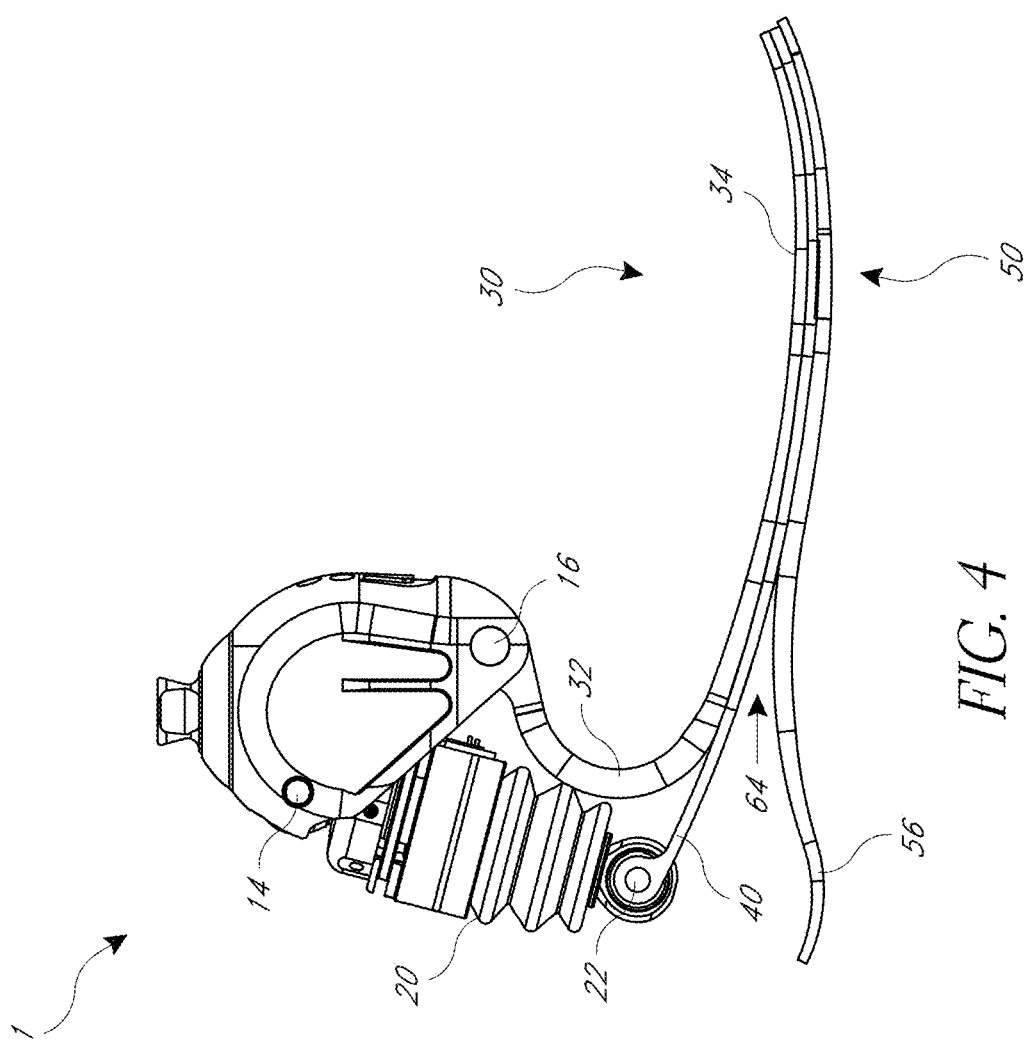

● 1. Rotational Sensor position

■ 2. Proximity Sensor position

▲ 3. Bend/Strain Sensor position

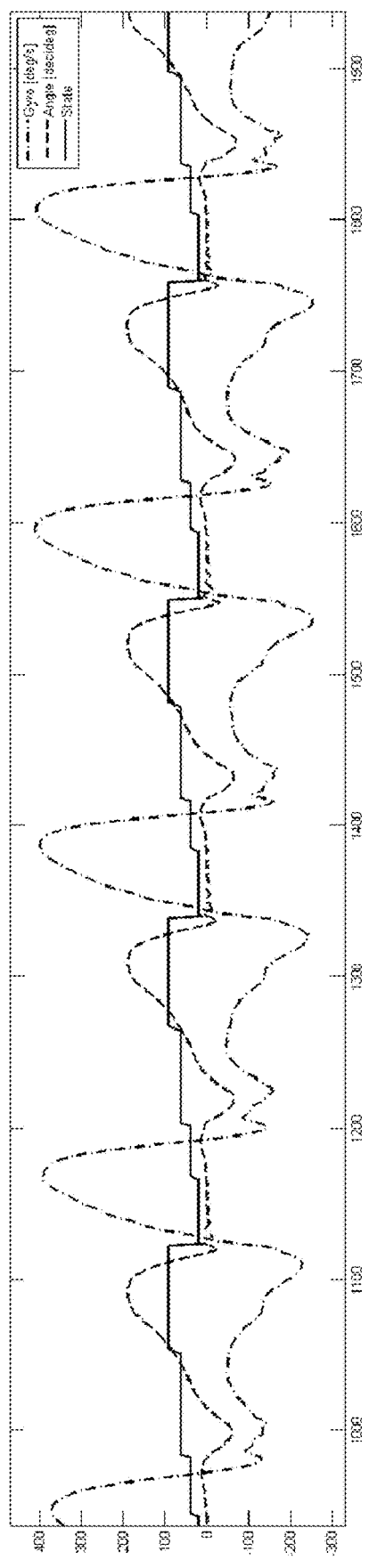
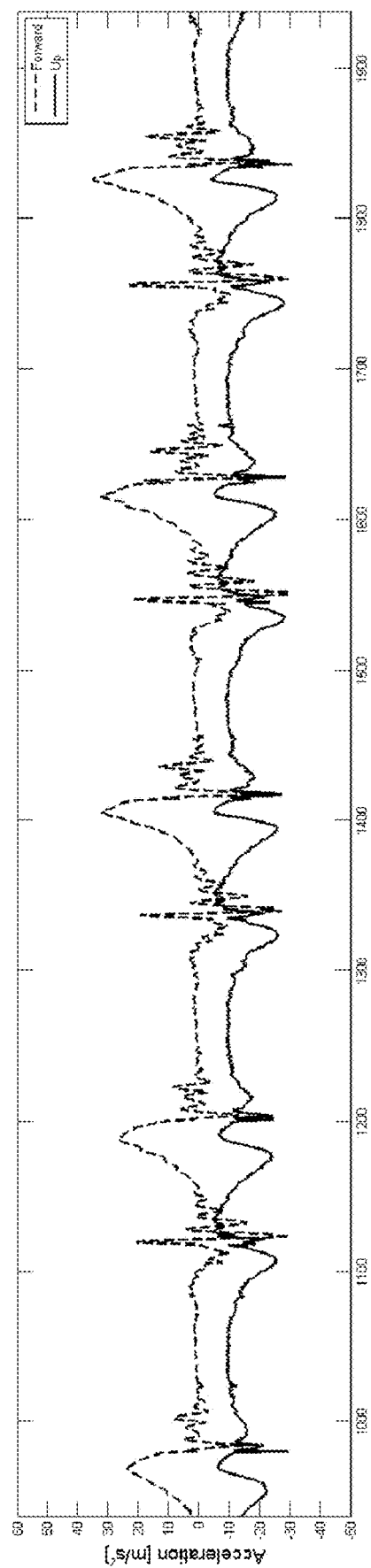
FIG. 52A
FIG. 52B

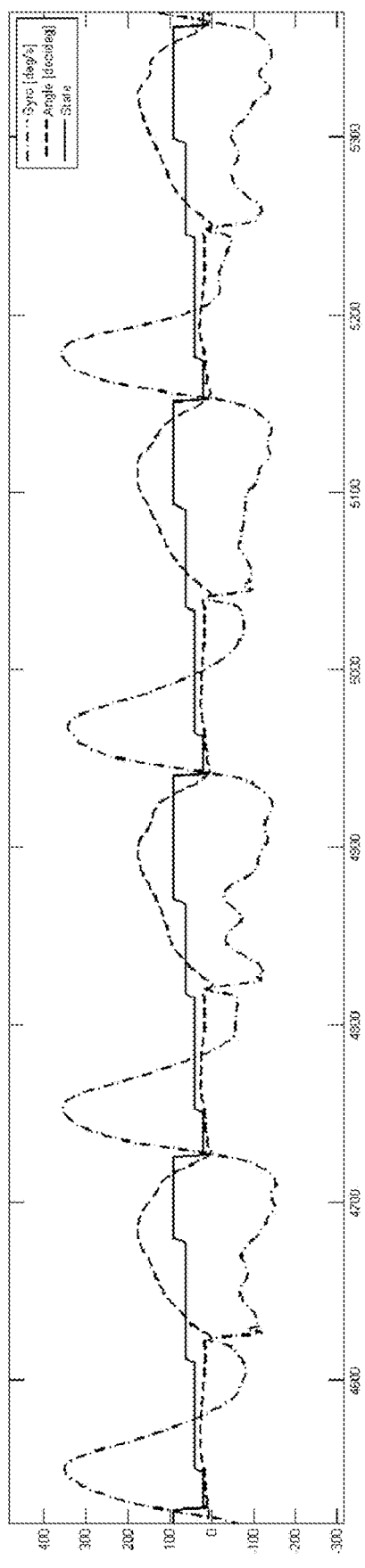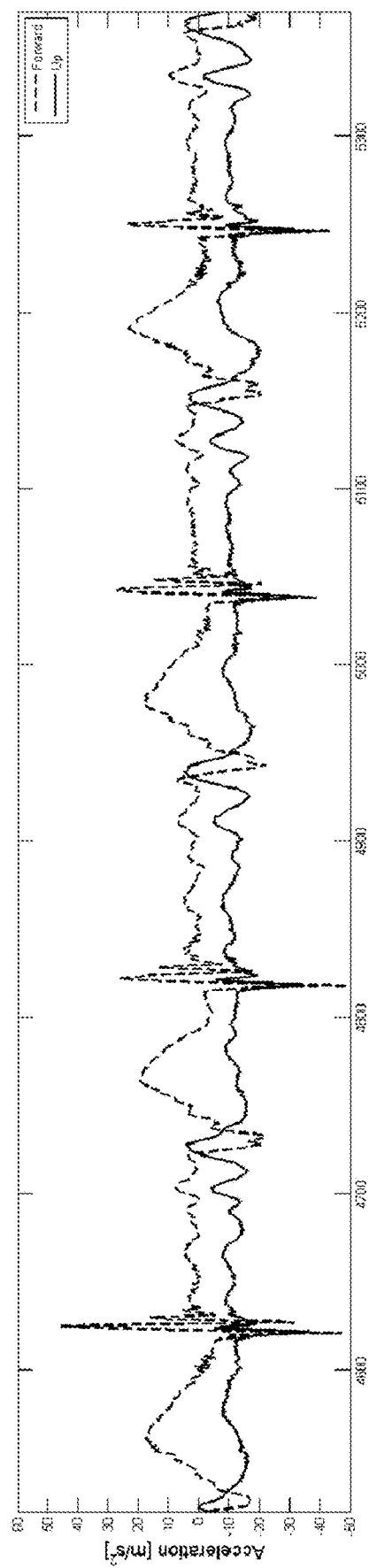
FIG. 54A
FIG. 54B

PROSTHETIC FOOT WITH REMOVABLE FLEXIBLE MEMBERS

PRIORITY INFORMATION

The present application is a divisional application of U.S. application Ser. No. 14/704,117, filed on May 5, 2015, and entitled, "PROSTHETIC FOOT WITH REMOVABLE FLEXIBLE MEMBERS," now U.S. Pat. No. 10,390,974, which is a continuation application of U.S. application Ser. No. 14/683,563, filed on Apr. 10, 2015, and entitled, "PROSTHETIC FOOT WITH REMOVABLE FLEXIBLE MEMBERS," now abandoned, which claims priority benefit under 35 U.S.C. § 119(e) to U.S. Provisional Patent Application Ser. No. 61/978,721 filed Apr. 11, 2014 and entitled PROSTHETIC FOOT WITH REMOVABLE FLEXIBLE MEMBERS; U.S. Provisional Patent Application Ser. No. 62/042,687, filed Aug. 27, 2014 and entitled PROSTHETIC FOOT WITH REMOVABLE FLEXIBLE MEMBERS; and U.S. Provisional Application Ser. No. 62/106,085, filed Jan. 21, 2015 and entitled PROSTHETIC FOOT, the entirety of each hereby expressly incorporated by reference herein.

BACKGROUND

Field

The present application relates to prosthetic feet and other prosthetic devices including a spring, and more particularly to prosthetic feet and other prosthetic devices having one or more flexible members between two or more joints (e.g., pivots) and allowing for variable stiffness during use.

Description of the Related Art

In the field of prosthetics, particularly prosthetic feet, it is desirable to provide a high level of functionality with reliable performance. Further, as each user is different, it is desirable to provide a prosthesis that can be adapted to the particular needs of each individual user.

SUMMARY

Particularly in the area of prosthetic feet, it is desirable to provide a prosthesis that provides stability throughout the gait cycle and in other activities such as stance. Further, during movement it is often desirable for a prosthetic foot to absorb and return elastic energy, while having enhanced energy conservation during ambulation. Even further, it is desirable for a prosthetic foot to be adjustable to an individual who may have various weights, heights, stride lengths, etc., as well as for prosthetic foot designs to allow for a variable stiffness, depending on the activity level of the amputee.

In accordance with one embodiment, a prosthetic foot is provided having one or more flexible members between two or more joints (e.g., pivots) to provide improved control and stability during a stance phase of gait cycle (e.g., provide more movement during stance). In one embodiment, the prosthetic foot is purely a mechanical foot. In another embodiment the prosthetic foot can include an actuator. In some embodiments, the actuator can be an active actuator (e.g., an electric motor, such as a motor with a power between approximately 60 W and 100 W) that can be selectively actuated (e.g., via an electric controller) to impart mechanical motion to the prosthetic foot (e.g., to change the orientation of the prosthetic ankle during a swing phase of gait cycle to dorsiflexion and then to plantarflexion). In another embodiment, the actuator can be a passive actuator (e.g., resilient member, spring or stiff beam).

In another embodiment, a prosthetic foot is provided with a variable stiffness control which allows the stiffness of the prosthetic foot to be adjusted for different types of gait. In some embodiments, the variable stiffness control is mechanically actuatable (e.g., actuated manually by a user) to vary the stiffness of one or more flexible elements of the prosthetic foot (e.g., by changing the length of a lever arm of a flexible element, or by varying a gap between adjacent flexible elements). In another embodiment, the variable stiffness control can be automatically or actively adjusted during ambulation by the user (e.g., automatic adjustment of a lever arm of a flexible element, or active varying of a gap between adjacent flexible elements), e.g., based on the activity level of the user or the phase of gait cycle. In some embodiments the variable stiffness control can be automatically adjusted based on a sensed parameter of gait (e.g., sensed with one or more sensors on the prosthetic device).

In still another embodiment, the prosthetic foot or device can include a housing or adapter (e.g., for coupling the prosthetic foot or device to another prosthetic component) with a mechanism that provides for flexible motion in one or more planes (e.g., sagittal, coronal, transverse) so as to allow motion of the housing or adapter in a medial-lateral, anterior-posterior, or torsional direction. In one embodiment, where the prosthetic device is a prosthetic foot, the housing or adapter can be located generally at a location associated with a natural human ankle, and provide for motion similar to that of a natural human ankle. In some embodiments, the mechanism can include one or more slots or openings in one or more surfaces of the housing or adapter (e.g., slots on medial and lateral surfaces of the housing or adapter), that movably receive one or more pins, axles or joint members that connect the housing or adapter with other components (e.g., flexible elements or foot plates) of the prosthetic foot.

In another embodiment, a prosthetic foot is provided that allows a medial-lateral movement and or twist movement in an ankle portion of the prosthetic foot during stance, thereby providing improved stability during stance.

In one embodiment, the prosthetic foot can comprise an adapter member comprising a connector configured to connect the adapter member to a user or another prosthetic device. The prosthetic foot can also comprise a bottom plate extending between a heel end and a toe end and an intermediate plate disposed above the bottom plate and extending between a proximal end and a distal end. The prosthetic foot can also comprise a support member extending between and interconnecting the proximal end of the intermediate member and a proximal portion of the adapter member, the support member pivotally coupled to the proximal end of the intermediate member. The prosthetic foot can also comprise a top plate assembly extending between a proximal end and a distal end, the top plate assembly including a split that extends from the proximal end to the distal end to divide the top plate assembly into a medial blade and a lateral blade. A distal end of the adapter member is disposed between and pivotally coupled to the medial and lateral blades at the proximal end of the top plate assembly to thereby facilitate a medial-lateral and/or a twist movement of the prosthetic foot during stance when the bottom plate is in contact with a support surface.

In one embodiment, a prosthetic foot comprises an attachment member and two or more flexible members. The attachment member can include a connector configured to connect the attachment member to a user or another prosthetic device. The two or more flexible members can be rotatably attached to the attachment member by rotatable joints such that the flexible members can both rotate and flex relative to the attachment member when the prosthetic foot contacts the ground.

In another embodiment, a prosthetic foot can include an attachment member, two or more flexible members, and an adjustable fastening member. The attachment member can include a connector configured to connect the attachment member to a user or another prosthetic device. The two or more flexible members can attach to the attachment member. Further, the two or more flexible members can extend from the attachment member to a foot portion of the prosthetic foot and be substantially movable relative to each other along their lengths. The adjustable fastening member can be configured to fasten the two or more flexible members along the foot portion of the prosthetic foot. Further, fastening can be provided at a plurality of positions along the length of the two or more flexible members to change the flexibility and resistance of the two or more flexible members.

In further embodiments, a prosthetic foot can include an attachment member, two or more flexible members, and a variable stiffness control member. The attachment member can include a connector configured to connect the attachment member to a user or another prosthetic device. The two or more flexible members can attach to the attachment member and can extend from the attachment member to a foot portion of the prosthetic foot. The flexible members can be substantially movable relative to each other along their lengths. However, the variable stiffness control member can be configured to adjust a length of a lever arm of the two or more flexible members along the foot portion of the prosthetic foot. For example, the variable stiffness control member can limit the relative motion between the flexible members.

In further embodiments, a prosthetic foot can include one or more flexible foot plates, an attachment member, and a means for modifying the stiffness of the prosthetic foot. The one or more flexible foot plates can be configured to bend along their lengths. The attachment member can include a connector configured to connect the attachment member to a user or another prosthetic device. The means for modifying the stiffness of the prosthetic foot can change the bending length of one or more of the flexible foot plates either prior to or during use.

In further embodiments, a prosthetic foot can include one or more flexible elements and an attachment member. The one or more flexible elements can be configured to bend along their lengths. The attachment member can include a connector configured to connect the attachment member to a user or another prosthetic device. Further, the attachment adapter can be connected to the one or more flexible elements via at least two pivotable joints. At least one of the flexible elements can extend between the at least two pivotable joints.

In further embodiments, a prosthetic foot can include an attachment member, at least one first brace, at least one first flexible member, an unpowered actuator, at least one second brace, and at least one second flexible member. The attachment member can include a connector configured to connect the attachment member to a user or another prosthetic device. The at least one first brace can mount to the attachment member and the at least one first flexible member can connect to the attachment member by the at least one first brace such that a force between the ground and the attachment member can be supported by the at least one first flexible member. The unpowered actuator can mount to the attachment member and the at least one second brace can be mounted to the actuator. The at least one second flexible member can connect to the attachment member by the at least one second brace such that a force between the ground and the attachment member can be supported by the at least one second flexible member.

In further embodiments, a prosthetic foot system can include a prosthetic foot and a plurality of replacement flexible members. The prosthetic foot can include an attachment member, at least one first brace, and at least one first flexible member. The attachment member can include a connector configured to connect the attachment member to a user or another prosthetic device. The at least one first brace can mount to the attachment member and the at least one first flexible member can releasably connect to the attachment member by the at least one first brace such that a force between the ground and the attachment member can be supported by the at least one first flexible member. The plurality of replacement flexible members can have different flexibility characteristics and be configured to replace the at least one flexible member to provide a different flexibility characteristic to a user.

In further embodiments, a method of adjusting a prosthetic foot can be provided. A prosthetic foot including at least one actuator and at least one first flexible member can be mounted to a user, and be used to support the user during ambulation. The at least one first flexible member can then be replaced with at least one second flexible member having different flexibility characteristics than the at least one first flexible member. The prosthetic foot can then be used to support the user during ambulation with the at least one second flexible member.

In further embodiments, a prosthetic foot includes an attachment member, at least one flexible member, at least one electric actuator, and at least one foot member. The attachment member can include a connector configured to connect the attachment member to a user or another prosthetic device. The at least one flexible member can be connected to the attachment member such that a force between the ground and the attachment member can be supported by the at least one first flexible member. At least one electric actuator can be connected to the attachment member such that a force between the ground and the actuator can be supported by the at least one actuator. The at least one foot member can be connected to the at least one flexible member and the at least one electric actuator, the at least one foot member being configured to contact the ground. Movement of the at least one actuator can cause a joint angle of the prosthetic foot to change. Further, the actuator can be configured to lock during substantially all of a stance phase of a gait cycle.

In a further embodiment, a method of operating a prosthetic foot can be provided. The prosthetic foot can include at least one electric actuator and at least one flexible member. The at least one electric actuator can be locked during a first portion of a stance phase of a gait cycle such that energy is stored in the at least one flexible member. The actuator can be released from locking and powered during a second portion of the stance phase such that the actuator provides power for toe-off and the flexible member releases stored energy for toe-off.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

FIG. 4 is a side view of the prosthetic foot of FIG. 1.

FIGS. 52A and 52B are graphs showing the behavior of a prosthetic foot during walking on level-ground.

FIGS. 54A and 54B are graphs showing the behavior of a prosthetic foot during stair descent.

DETAILED DESCRIPTION

FIGS. 1-8 depict an embodiment of a prosthetic foot 1. The prosthetic foot 1 can attach to a user or to another prosthetic device with an attachment member 10. The attachment member 10 is depicted as including a first connection portion 12 shown as a pyramid connector. The pyramid connector can attach to a stump on a user, to another prosthetic device, or to any other appropriate object. Further, it will be understood that the first connection portion 12 can include attachment features other than a pyramid connector, such as a threaded hole or screw, a latch, a magnetic member, tube clamp, or other features.

Figure 7:
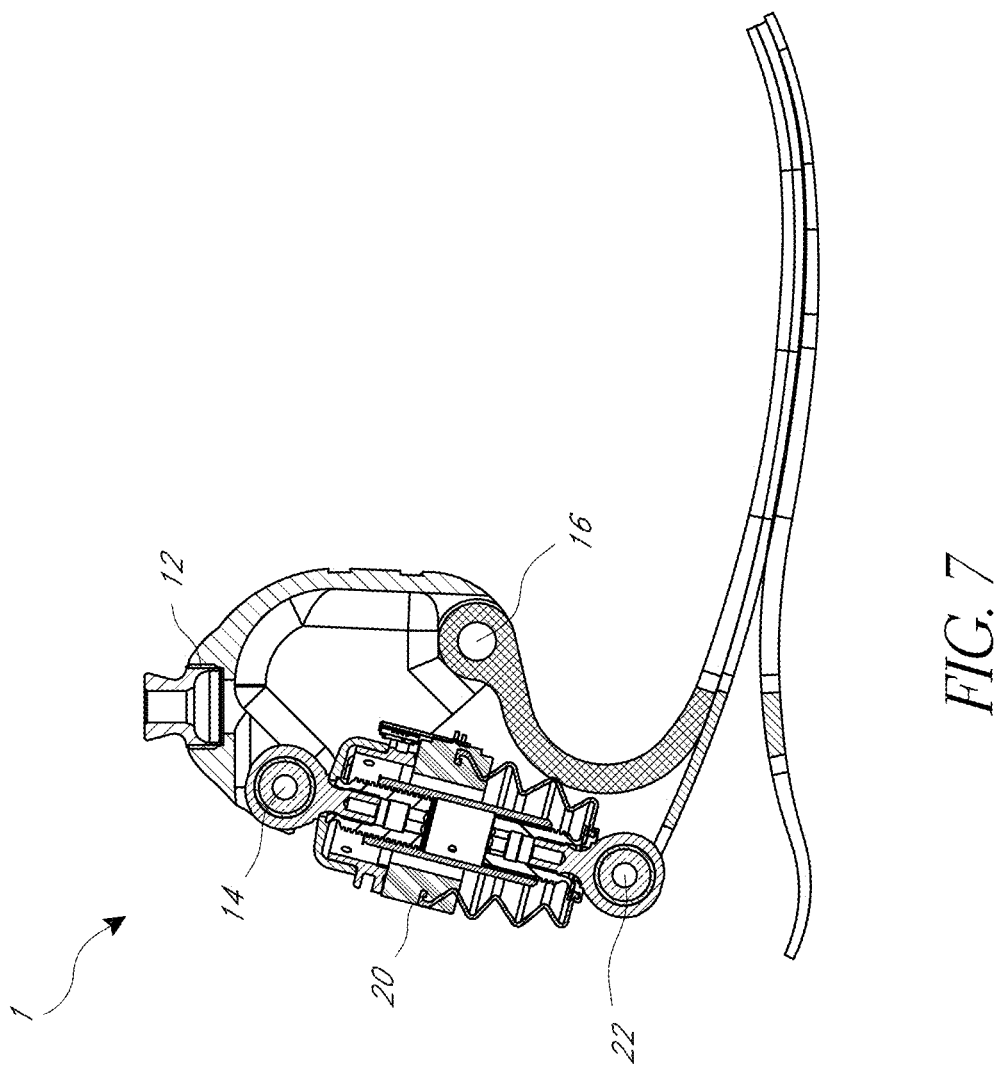
FIG. 7 is a cross-sectional side view of the prosthetic foot of FIG. 1.

The attachment member 10 can additionally include second and third connection portions 14, 16 (see FIGS. 4, 7). The attachment member 10 can serve to provide a rigid connection between the connection portions 12, 14, 16. For example, the attachment member 10 can comprise a substantially rigid material such as aluminum, steel, titanium, other metals or metallic alloys, carbon fiber, composites, or substantially rigid plastics. However, in other embodiments the attachment member 10 can be configured to provide flexibility, potentially in multiple planes. Thus, in some embodiments the attachment member 10 can comprise a more flexible material or include flexible joints between separate components of the attachment member 10. For example, in some embodiments the attachment member 10 can have a flexible connection with the first connection portion 12, allowing for motion in the medial/lateral and/or anterior/posterior directions. Further, the connection may allow torsional flexibility with the first connection portion 12. In other embodiments, as further described below, the attachment member 10 can have a flexible connection with one or both of the second and third connection portions 14, 16.

Further, in some embodiments the attachment member 10 can include other features of a prosthetic foot such as sensors configured to measure, for example, the position and movement of the prosthetic foot, the position and movement of various joints and components on the prosthetic foot (such as the rotational position and movement at the connection portions 14, 16 and an actuator 20, as further discussed below), pressures and forces on various components of the prosthetic foot 1 (such as on the attachment member 10, the actuator 20, or the flexible members 30, 40, 50, further discussed below), and other measurable characteristics of the prosthetic foot. The sensors can additionally be configured to measure the prosthetic foot's environment, such as a terrain on which the prosthetic foot 1 moves. It will be understood that these sensors can be positioned on other elements of the prosthetic foot 1, such as the actuator 20, the flexible members 30, 40, 50, and other elements, further described below. In some embodiments, one or more of the flexible members 30, 40, 50 can be foot plates (e.g., generally planar or flat, or have a generally rectangular transverse cross-section).

In some embodiments, sensors positioned in the connection portions 14, 16, 22 can provide load measurement during stance phase (for example when a user is resting on the foot 1) when flexible members 30, 40 bend due to loading on the foot. For example, the sensors can measure a bending of the flexible members 30, 40 at the connection portions 16, 22, the bending then being used to estimate a load on the flexible members. In stance phase, these measurements can therefore be used to determine if the user is loading the heel or toe by comparing it to the sensed angle (and optionally an estimated load) just before heelstrike.

In some embodiments, the sensors can include rotational sensors such as rotational hall effect sensors (for example, sensor type AS5048 manufactured by Austria Micro Systems). Such sensors can measure a rotation at the connection portions 14, 16, 22 that can be indicative of loads placed on the flexible members 30, 40, 50. Other sensors can also be used such as gap measurement sensors. The gap measurement sensors can generally include two components spaced from each other to create a gap. As the distance between the two sensors is increased or decreased, a signal can be produced indicative of this distance. For example, the gap measurement sensor can be a linear hall effect sensor (for example, sensor type SS49E-L manufactured by Honeywell International Inc.). The gap measurement sensors can be placed in or on the flexible members 30, 40, 50 to directly measure a bending of the flexible members along their length.

In some embodiments, the rotational sensors can be provided at rotational joints of a prosthetic foot 1. For example, a gap measurement sensor can be provided at any one or more of the connection portions 14, 16, and 22. The gap measurement sensor can then measure a rotational position between the elements at the connection portions 14, 16, 22, such as the attachment member 10 and the first flexible member 30, the attachment member 10 and the actuator 20, and the actuator 20 and the second flexible member 40, as depicted in the prosthetic foot 1 in FIG. 1.

Figure 38:
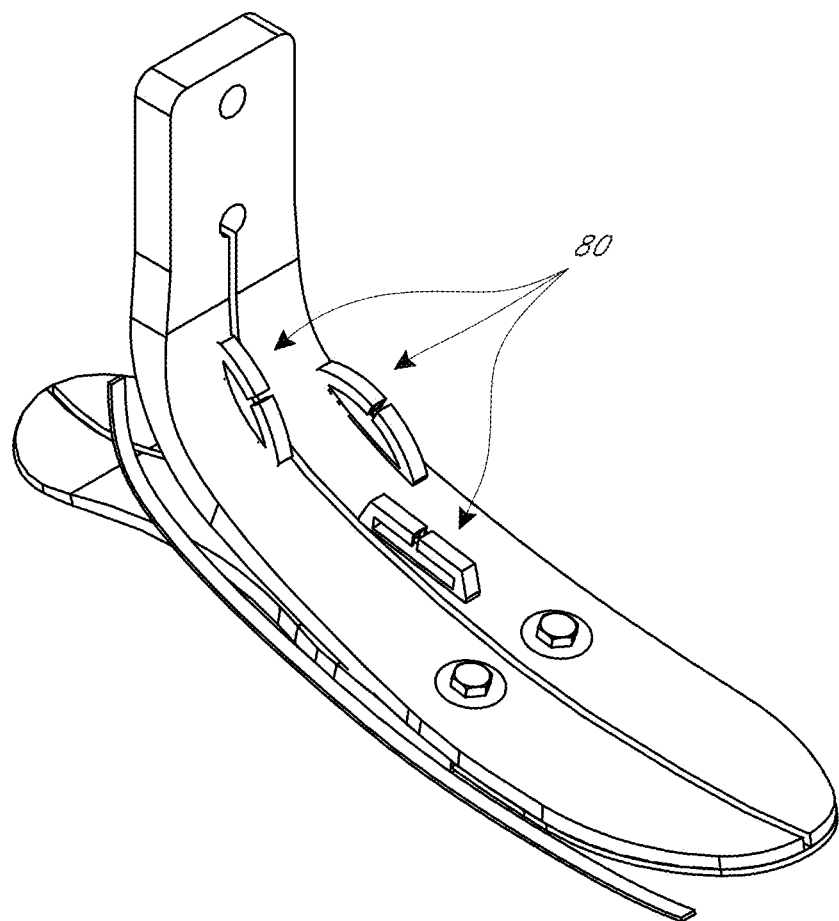
FIG. 38 is a perspective view of a portion of an embodiment of a prosthetic foot similar to the embodiments discussed in the preceding figures, including gap measurement sensors.

In other embodiments, the gap measurement sensors can be provided along one or more of the flexible members 30, 40, 50. Some embodiment sensors are depicted in FIG. 38, as an example.

Figure 51:
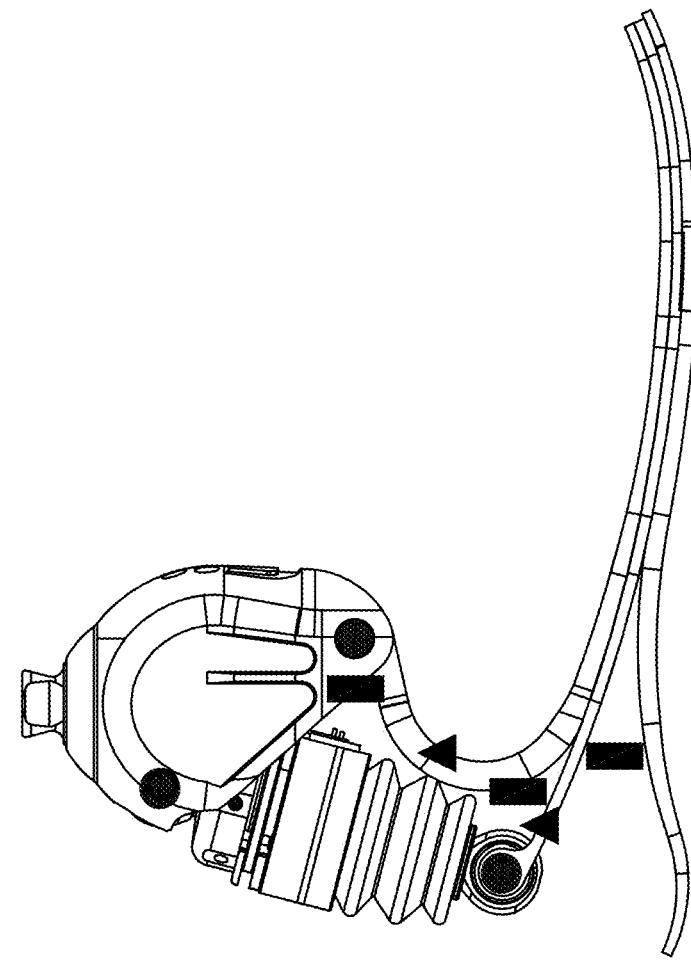
FIG. 51 is a side view of the prosthetic foot of FIG. 1, indicating the possible location of various sensors.

The prosthetic foot 1 can include other sensors such as an accelerometer, gyroscope, load sensor, or other sensors. These sensors can detect various aspects including the angular position of the prosthetic foot's joints and the angular position of the prosthetic foot relative to the earth, axial or torsional loads on the prosthetic foot, or other variables. For example, as shown in FIG. 51, rotational sensors such as an angular encoder can be positioned at rotatable joints at the connection portions 14, 16, and 22. Proximity sensors such as the gap measurement sensors discussed above, can be positioned near the connection portions 16, 22 and where the second and third flexible members 40, 50 meet to measure rotations and bending at these joints. Strain sensors can also be placed on any of the flexible members 30, 40, 50 to measure bending of these members.

The attachment member 10 can also include electronics (e.g., computer processor). For example, the attachment member 10 can include electronics configured to receive information from the sensors, discussed above. Further, in some embodiments, the attachment member 10 can include electronics configured to communicate information (e.g., information from the sensors) to other electronic devices, such as to other prosthetic devices or to an external computer (e.g., via wired or wireless communication, such as RF communication). Such electronics may also be configured to receive information from other prosthetic devices or an external computer, such information potentially including information from other sensors and/or operational commands for the prosthetic foot 1.

The information from the sensors can optionally be processed by the electronics (e.g., using one or more algorithms stored in a memory) to determine certain gait patterns, terrains, and appropriate alignment settings for the prosthetic feet described herein. For example, the foot can have a particular translational motion, rotational bending, load patterns, and other characteristics during particular types of ambulation. FIGS. 52A-62 depict various example movement patterns during particular gait patterns and transitions between gait patterns.

Figure 52C:
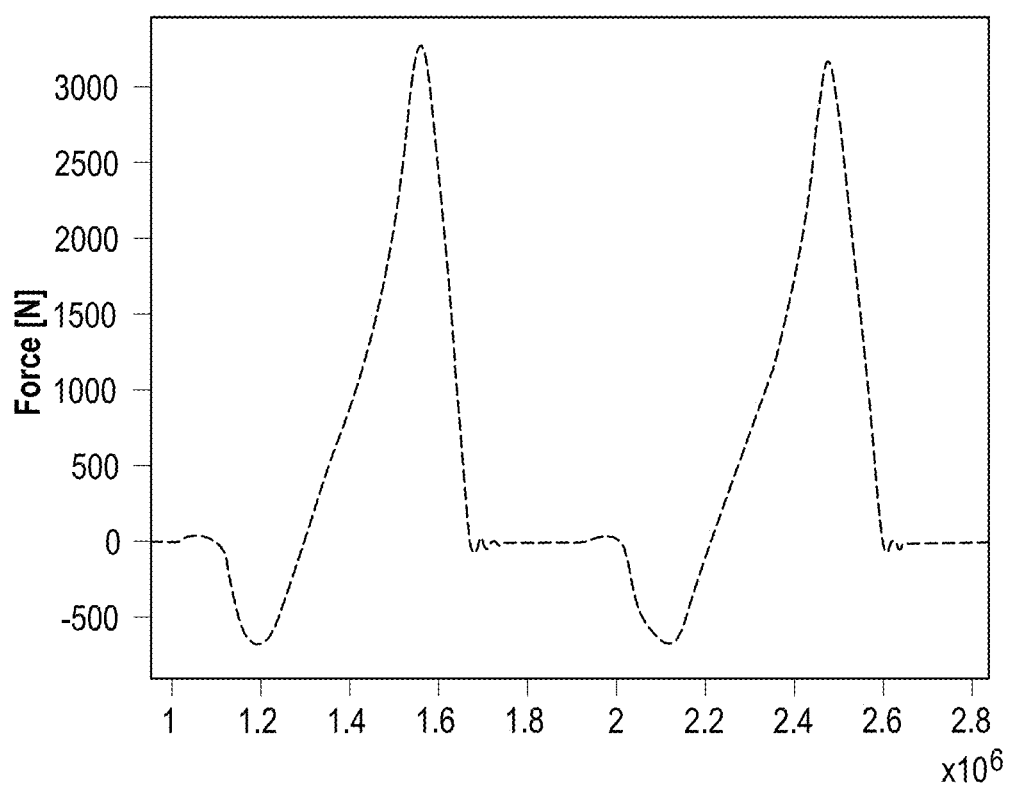
FIG. 52C is a graph showing the relative loads on the heel portion of a prosthetic foot and the toe portion of the prosthetic foot during level-ground walking.

FIGS. 52A and 52B depict data characteristic of level-ground walking by a prosthetic foot. As indicated, one line indicates a rotational bending angle of the prosthetic foot. The rotational bending angle can be measured using a variety of sensors, such as the sensors depicted in FIG. 51, and described above. In a particular embodiment, the angle can be determined from a ratio of a measured load at the heel of the foot and a measured load at the toe of the foot. Such a load measurement during level-ground walking is depicted in FIG. 52C, and it can be seen that the measured load graph is substantially similar to the angle graph in FIG. 52A. A high load on the heel can indicate plantarflexion and a high load on the toe can indicate dorsiflexion. Other methods can also be used to measure the rotational bending, such as with a rotational sensor at one of the connection portions.

Another line indicates a gyroscopic angular measurement, measured on an axis perpendicular to the sagittal plane, indicating a rotational position of the housing or cover 18 of the prosthetic foot. Thus, the gyroscopic angular measurement can indicate a rotational position of the first connection portion 12 (such as a pyramid connector), and a lower leg member or amputated stump to which the prosthetic foot connects, relative to the environment (as opposed to a bending of the joint, as measured by the load sensors discussed above).

Another line indicates the determined transitions between different portions of a gait cycle, such as pre-mid-stance, post-mid-stance, pre-mid-swing, and post-mid-swing (depicted as a step-function on the graph). These portions of the gait cycle can be determined based on the data measured. However, other data could also be used, such as data from accelerometers (which can measure rotational angle relative to gravity, and thus the environment), rotational encoders, or other sensors described herein.

Finally, the graphs also show acceleration data on the prosthetic foot in both a forward direction (perpendicular to the coronal plane) and in an upward, vertical direction (perpendicular to the transverse plane). It can be seen that acceleration is substantially zero during the stance phase. Further, it should be noted that the vertical direction is offset to below-zero due to the acceleration of gravity.

As shown in FIG. 52A, during level-ground walking the heel-load on the prosthetic foot can dominate over toe-load during the pre-mid-stance phase, indicating plantarflexion. The load can then transition toward dominant toe-load as the foot gradually transitions to post-mid-stance and dorsiflexion. The ratio between these loads can then return to baseline levels during swing phase (indicating a neutral angle), as the foot transfers no load with the ground. Other angular measurements can also be used to determine the phase of gait. Additionally, during level-ground walking the prosthetic foot can accelerate upwards and then downwards during the swing phase. An integration of this acceleration data can indicate a similar upward and then downward velocity.

Figure 53A:
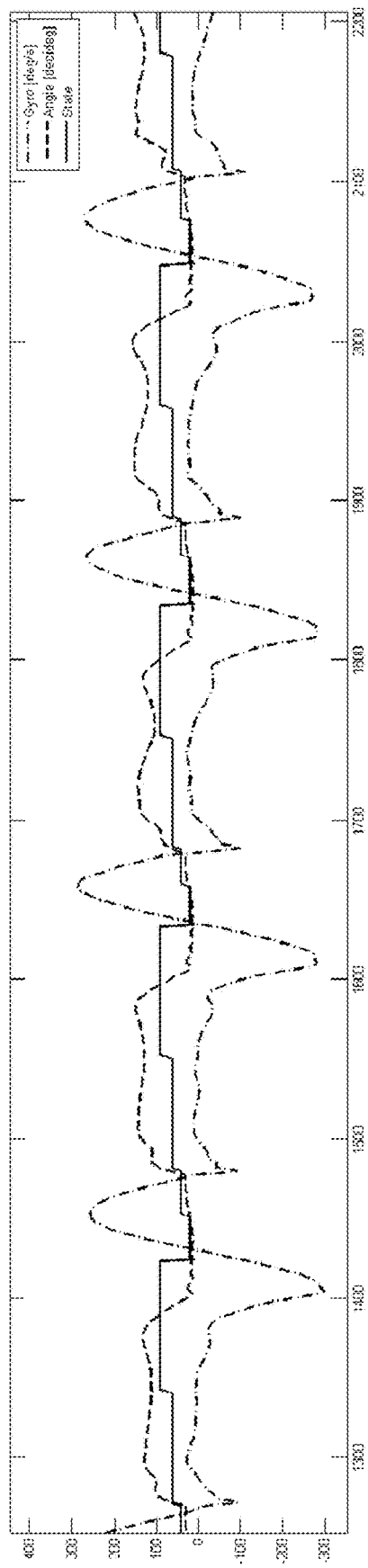
FIGS. 53A and 53B are graphs showing the behavior of a prosthetic foot during stair ascent.
Figure 53B:
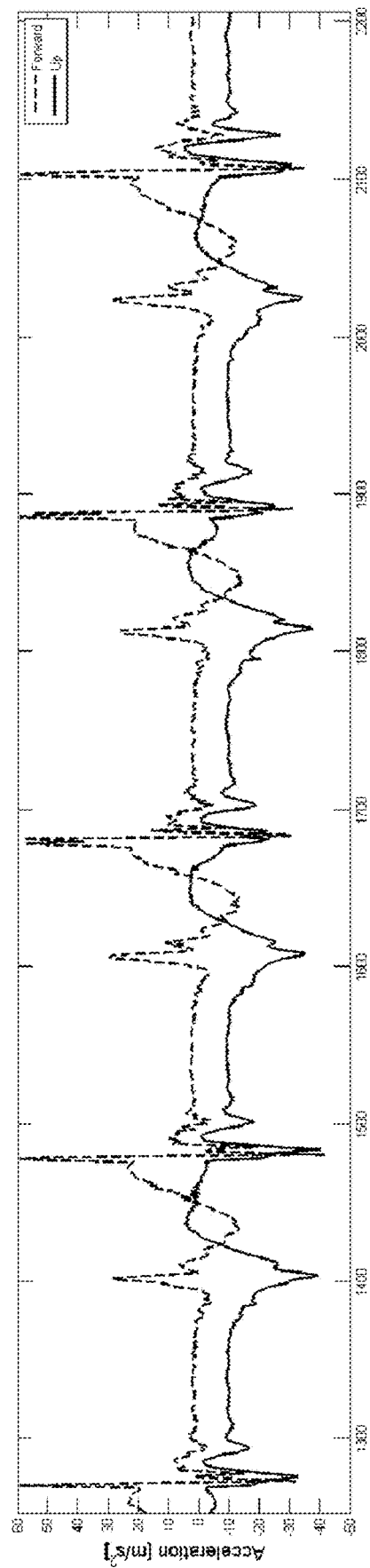
Figure 55A:
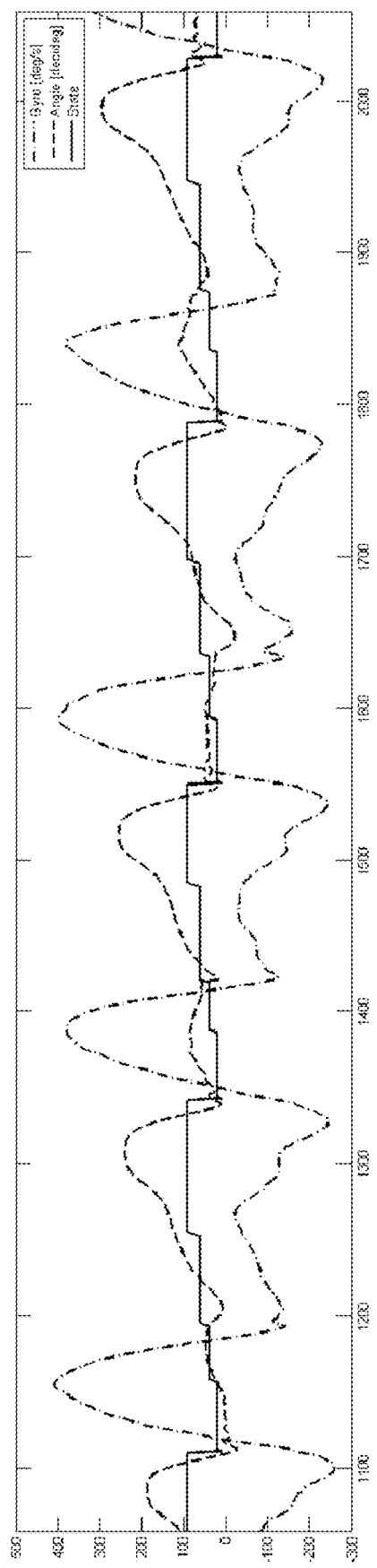
FIGS. 55A and 55B are graphs showing the behavior of a prosthetic foot during ramp ascent.
Figure 55B:
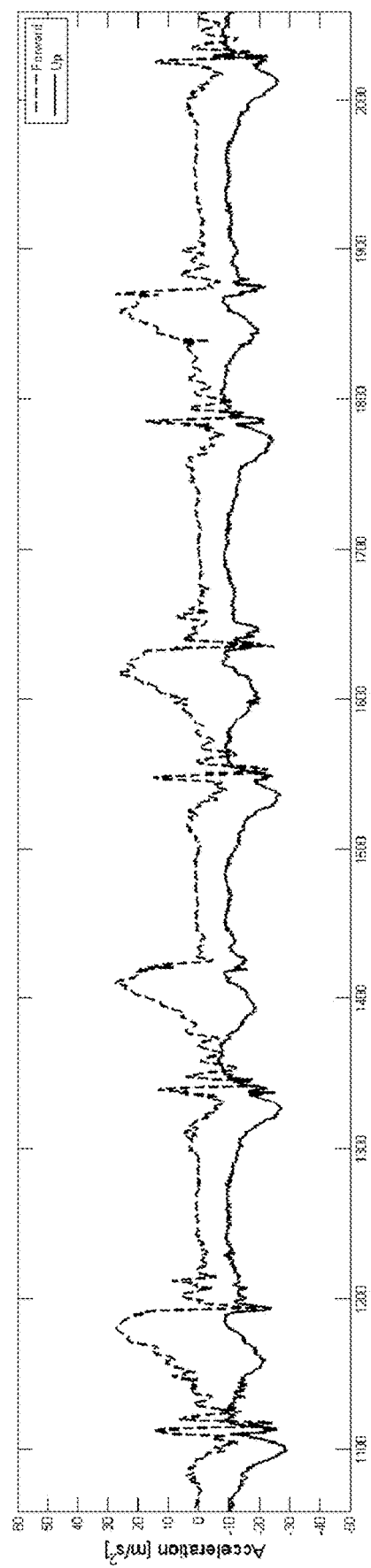
Figure 56A:
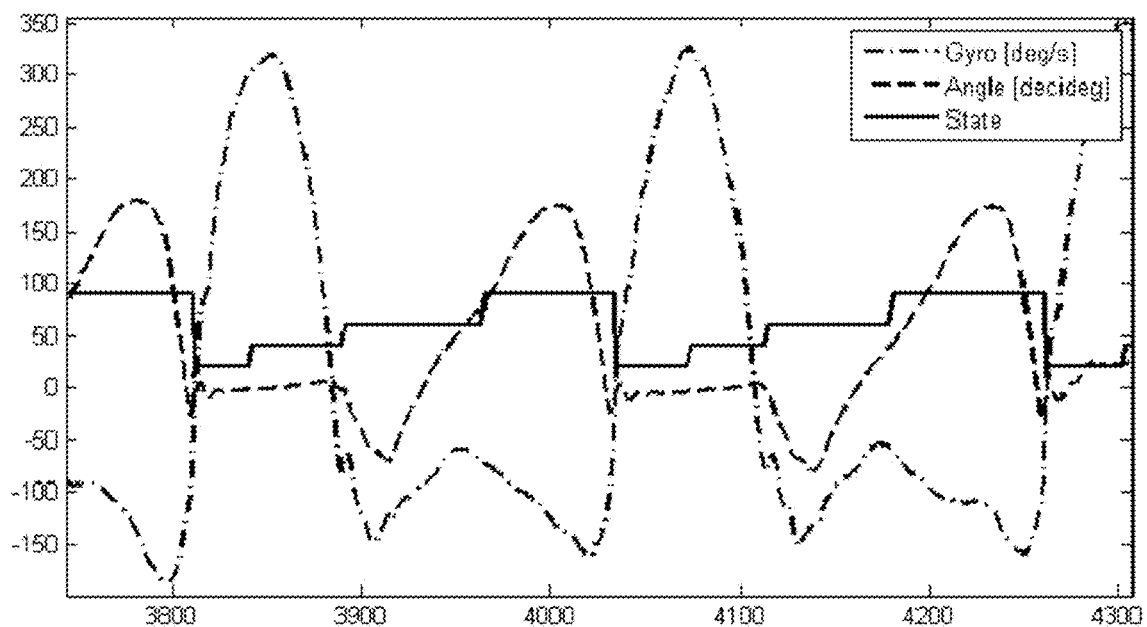
FIGS. 56A and 56B are graphs showing the behavior of a prosthetic foot during ramp descent.
Figure 56B:
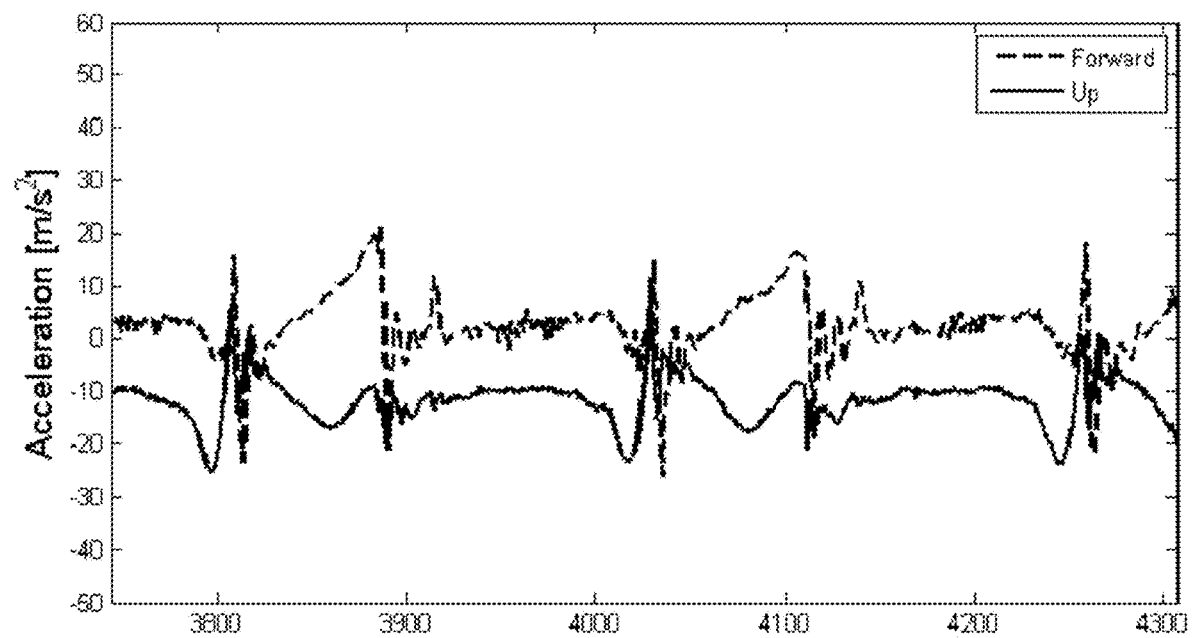
Figure 57A:
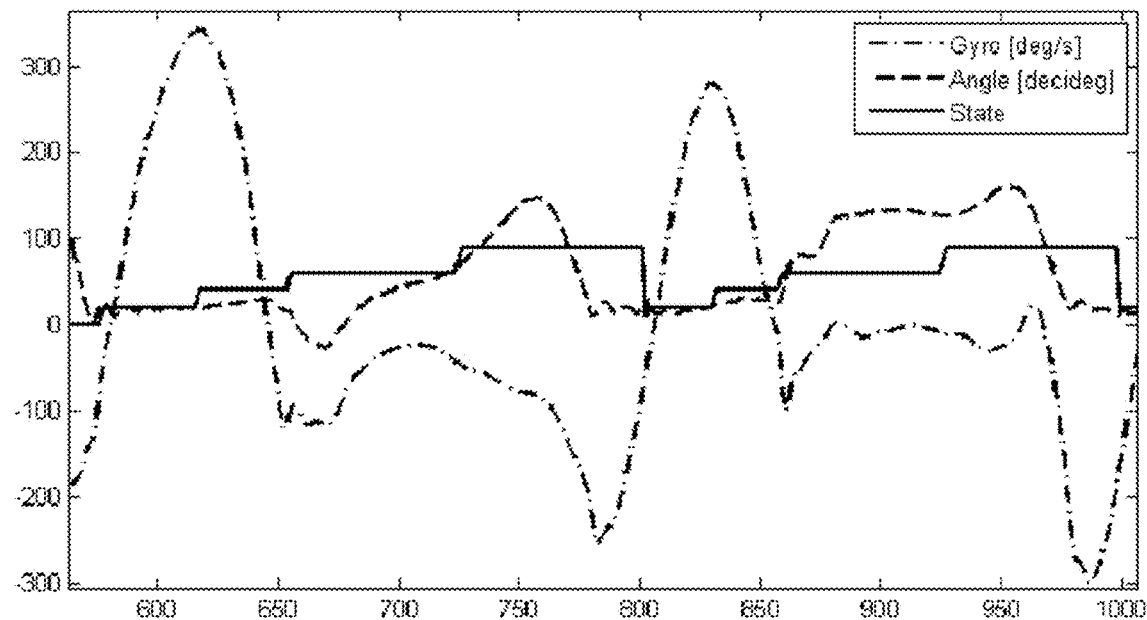
FIGS. 57A and 57B are graphs showing the behavior of a prosthetic foot while transitioning from level-ground walking to stairs ascent.
Figure 57B:
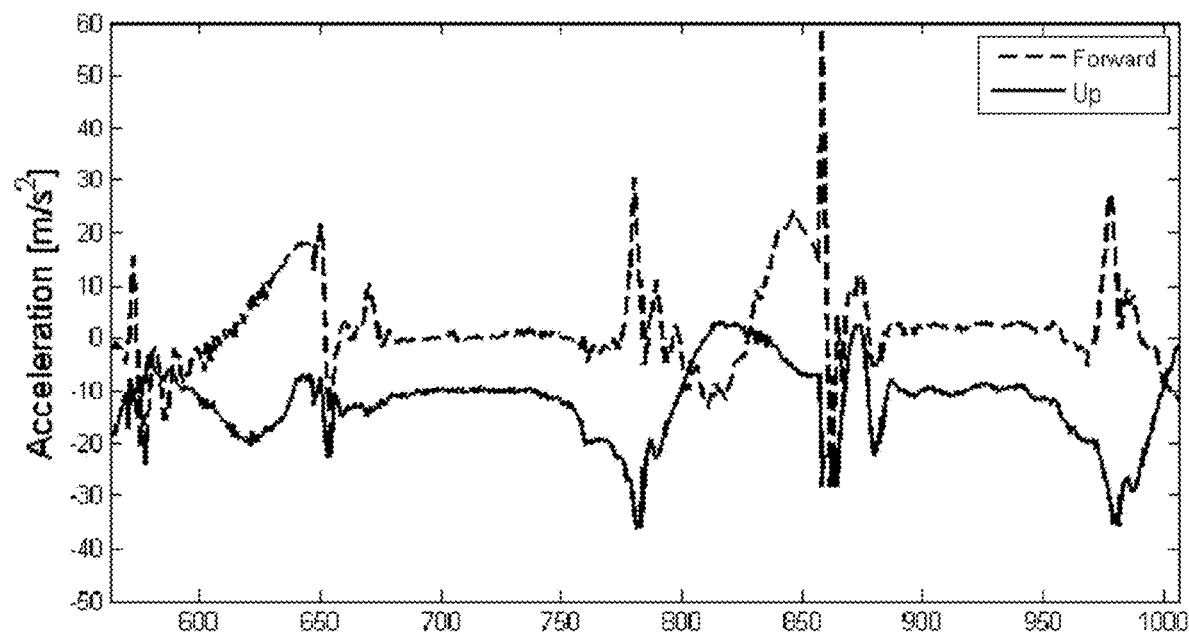

As shown in FIG. 53A, during stair-ascent the toe-load (and dorsiflexion) can be dominant throughout substantially all of stance. The load ratio (and angle of bending) can have two peaks, indicating initial contact with the ground and toe-off. As shown in FIG. 54A, stair-descent can similarly have a toe-load dominant behavior throughout substantially all of stance. However, during stair descent there may be a slight heel-load (plantarflexion) dominant portion at the beginning of stance, and a single toe-load peak. Vertical acceleration data during stair ascent (FIG. 53B) and stair descent (FIG. 54B) can indicate a generally upward or downward velocity, which can also be used to indicate the type of motion.

FIGS. 55A-55B and 56A-56B, respectively, show ramp-ascent and ramp descent. During ramp-ascent (see FIG. 55A), the heel-load (plantarflexion) can be slightly dominant early in stance, with a slowing in weight-shift toward the toe-load (dorsiflexion) during mid-stance. This slowing in the weight-shift (and angle change) can also be viewed as an inflection point in the ratio between heel and toe loads. During ramp-descent (see FIG. 56A), the heel-load at pre-mid-stance can be much stronger, and the transition toward a toe-load can be faster during mid-stance. Again, vertical acceleration data can also be used (see FIGS. 55B and 56B), as discussed above regarding stair ascent and descent.

Detection of these characteristics can indicate to modules within the electronics on the prosthetic foot what type of gait (and thus, for example, what type of terrain) with which a user is walking. For example, a strong heel-load (plantarflexion) at pre-mid-stance, a strong toe-load (dorsiflexion) at post-mid-stance, and a relatively steady transition from heel-load to toe-load (or joint angle) can indicate level-ground walking. A two-peak pattern and/or a consistently dominant toe-load (dorsiflexion) can indicate stair ascent. A one-peak toe-load pattern with a very slight heel-load (plantarflexion) at pre-mid-stance can indicate stair descent. A one-peak toe-load (dorsiflexion) pattern with a very slight heel load (plantarflexion) at pre-mid-stance and a slowing in the weight-shift (angle change) toward toe-load during mid-stance can indicate ramp ascent. Finally, a strong heel-load (plantarflexion) at pre-mid-stance, a strong toe-load (dorsiflexion) at post-mid-stance, and a quickening transition during mid-stance can indicate ramp-descent. Further, acceleration data can be used to determine if vertical velocity is generally upward, downward, or level. These are just a few examples. Additional gait patterns can also be detected, and additional sensors can also be used. The actuator can then be operated according to the detected gait pattern.

Even further, as shown in FIGS. 57A-60B, transitions from one gait pattern to another can be detected. For example, sensors in the foot can detect a velocity and direction of movement of the foot during swing phase using acceleration data from accelerometers. More particularly, in some embodiments the device can detect a change in terrain at mid-swing before landing on the new terrain using this data. Data from the first half of the swing phase can potentially provide enough information to anticipate the coming terrain transition. However, data from the second half of the swing phase can also be used to either determine a terrain transition or to determine additional aspects of the terrain and adjust the joint angle.

Figure 58A:
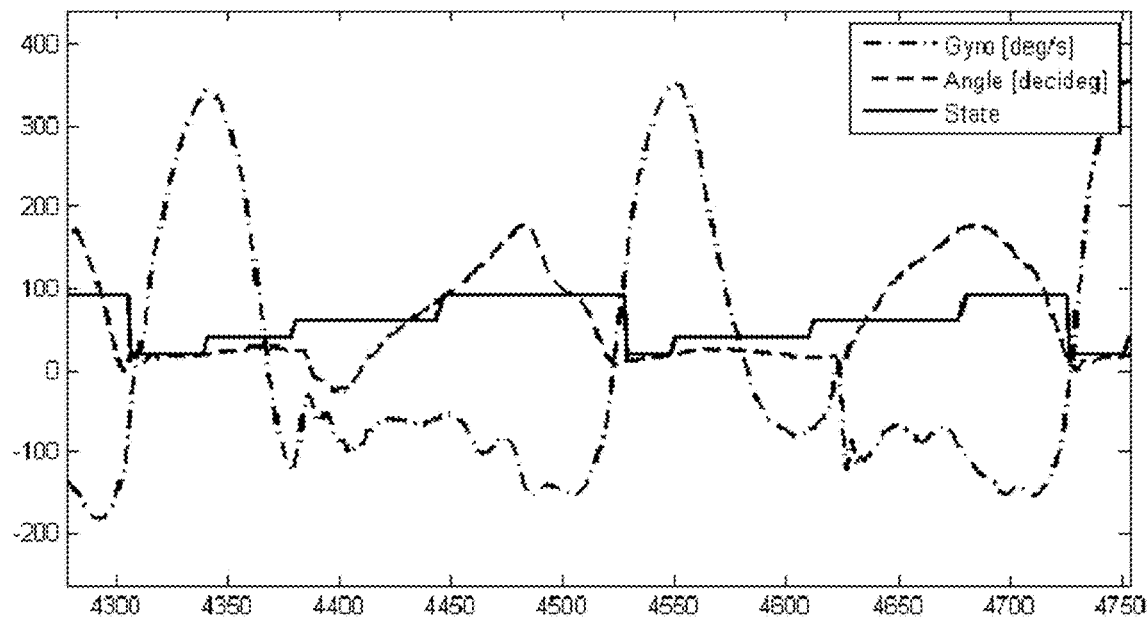
FIGS. 58A and 58B are graphs showing the behavior of a prosthetic foot while transitioning from level-ground walking to stairs descent.
Figure 58B:
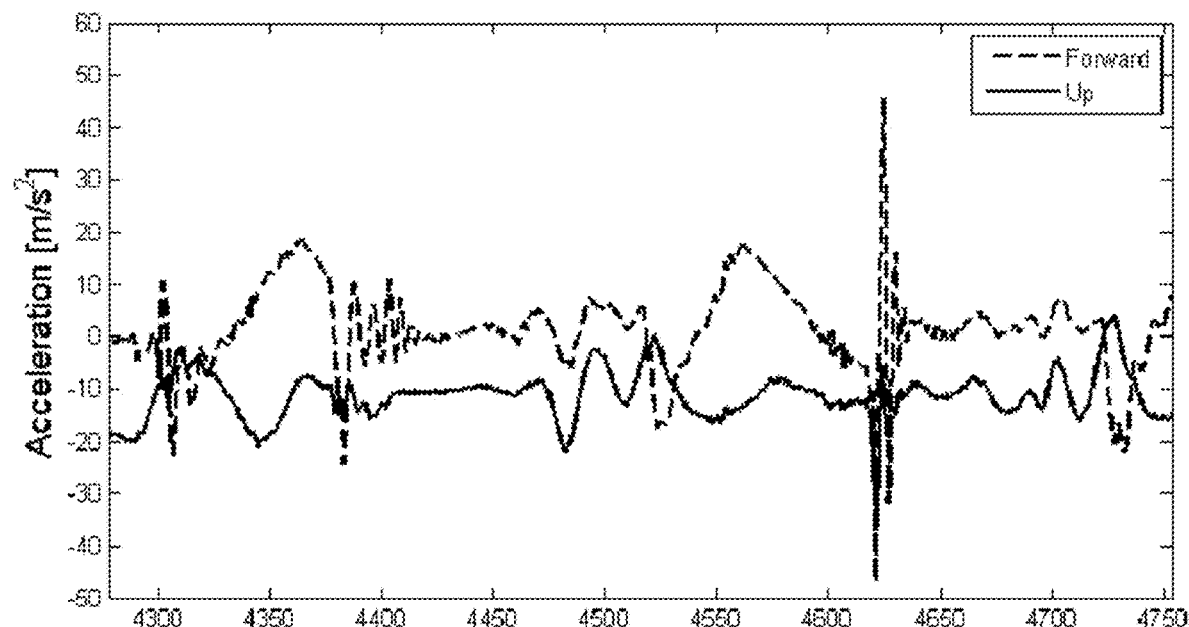
Figure 59A:
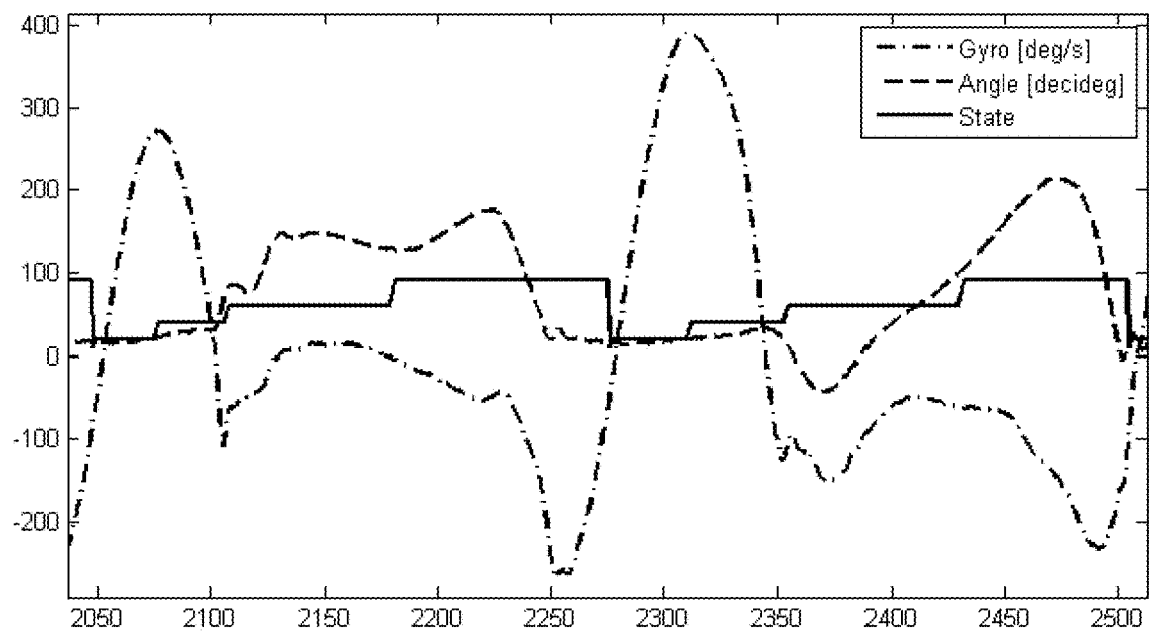
FIGS. 59A and 59B are graphs showing the behavior of a prosthetic foot while transitioning from stairs ascent to level ground walking.
Figure 59B:
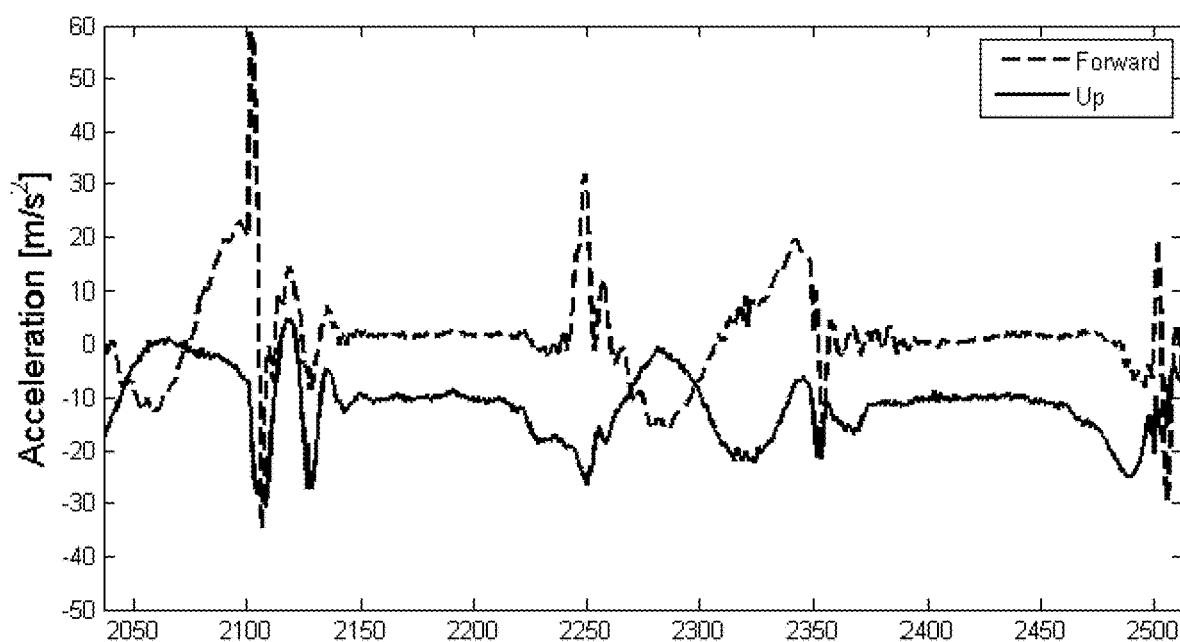
Figure 60A:
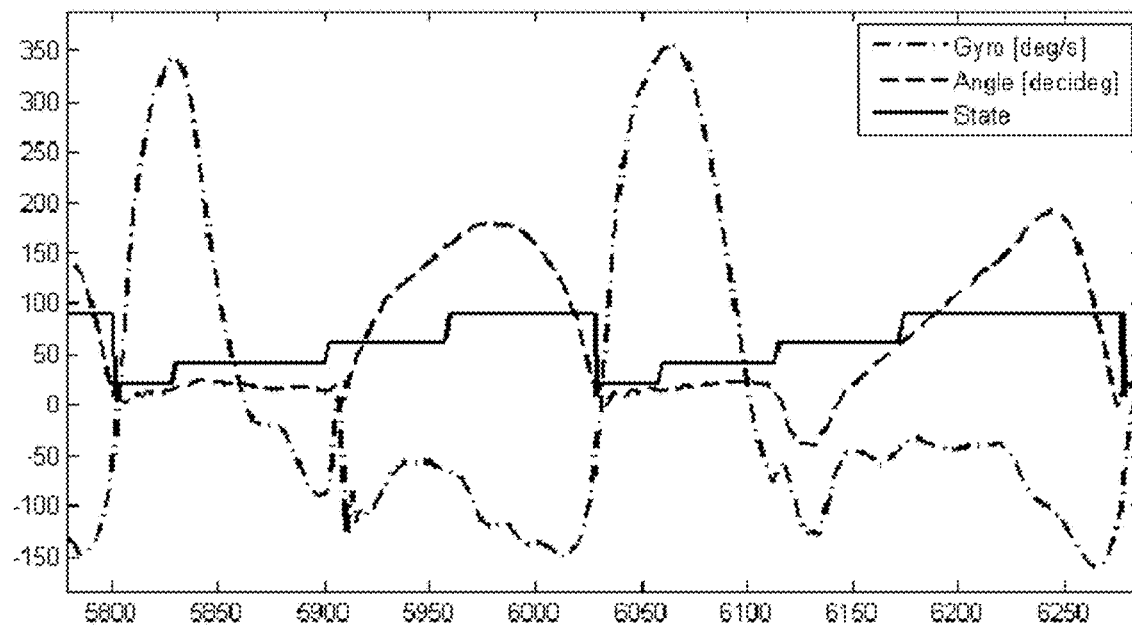
FIGS. 60A and 60B are graphs showing the behavior of a prosthetic foot while transitioning from stairs descent to level ground walking.
Figure 60B:
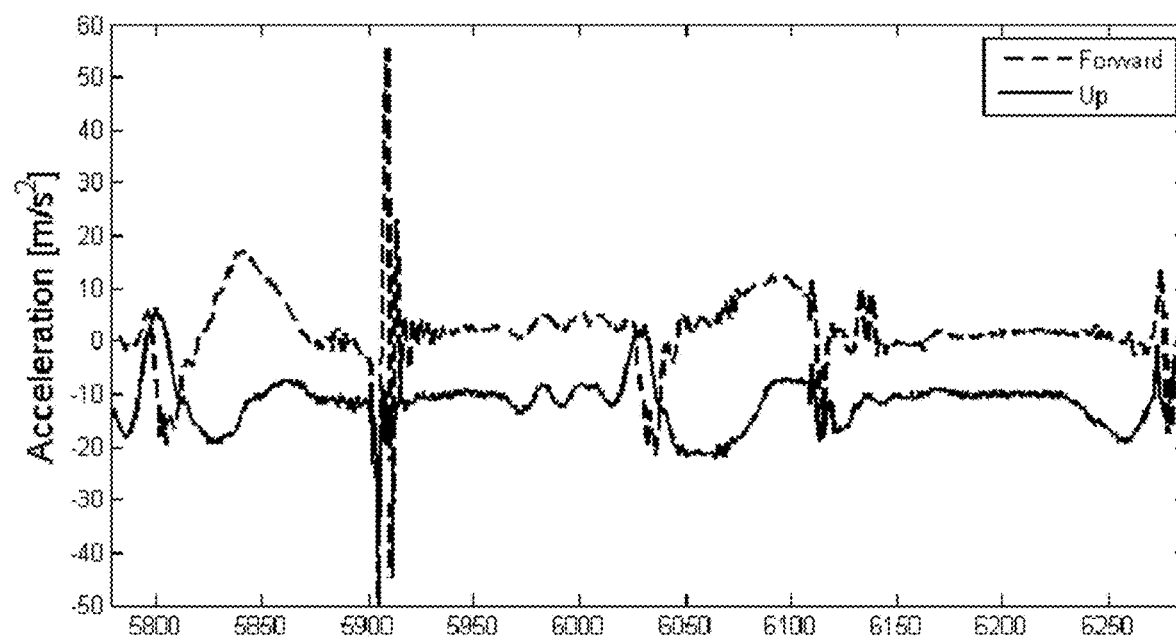

For example, velocity components in the forward direction and the upward direction can be compared to determine a general direction of motion (for example, using a two-input arctangent function). When walking on level ground, the foot typically is moving downward at mid swing. However, if the foot is moving in an upward direction at mid-swing, the foot is likely moving upwards (on stairs, or a slope). Thus, a transition from level ground to stair or ramp-ascent can be indicated when the foot moves in an upward direction at mid-swing, and the foot's behavior can be adjusted accordingly (e.g., by adjusting the ankle angle to a desired stair ascent position). Such a change in acceleration can be seen in FIG. 57B, which shows an unusually high upward acceleration during swing phase at the transition from level ground walking to stair ascent. Similarly, a transition from level ground walking to stair descent is depicted in FIGS. 58A and 58B, showing a prolonged downward acceleration during post-mid-swing. FIGS. 59A, 59B, 60A, and 60B show reverse transitions, from stair ascent/descent to level-ground walking. Such transitions can be detected in a similar manner. When detecting ramp ascent/descent, the prosthetic foot can also use additional steps to determine the inclination of the ramp. Similarly, a transition from stair or ramp-ascent to level ground walking can be indicated when the foot moves in a downward direction at mid-swing, and the foot's behavior (e.g., ankle angle) can be adjusted accordingly.

Sensors can also indicate when the prosthetic foot is going to exit a relaxed state such as a sitting or "chair" position. A gyroscope measuring rotations within the sagittal plane can indicate when the prosthetic foot is being moved backwards by a user in preparation to exit a seated position, by measuring a change in angle of the prosthetic foot relative to the environment. In other embodiments, this backward motion can be measured by an accelerometer or other sensor. The device can then exit a relaxed mode and facilitate or power movement into a dorsiflexed position in preparation to exit the seated position. This movement can potentially happen during a swinging of the prosthetic foot backwards, such that the adjustment toward dorsiflexion can occur prior to the foot touching the ground. Even further, in some embodiments the prosthetic foot can prepare for active use to assist the user out of a seated position.

Figure 61:
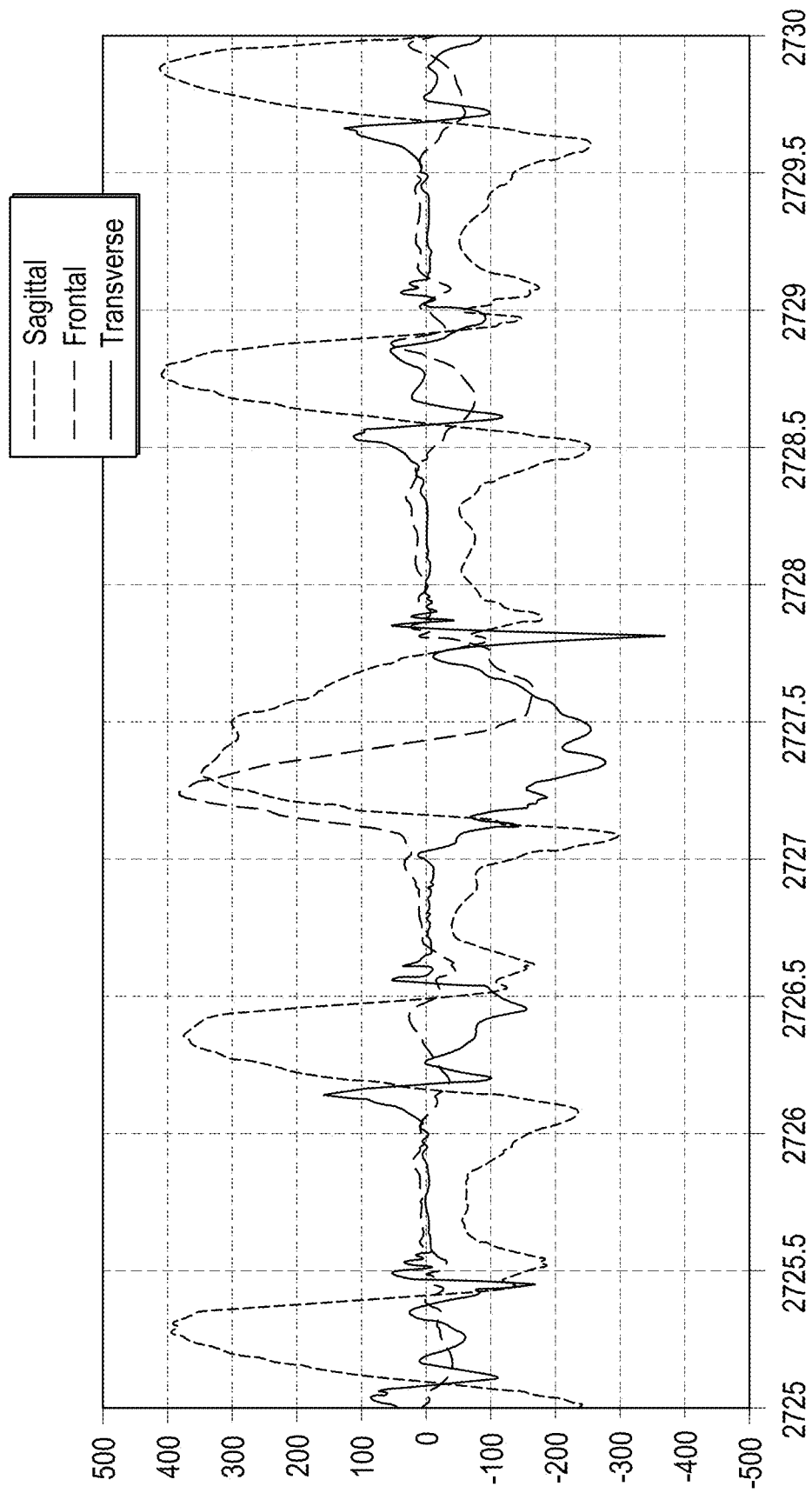
FIGS. 61 and 62 are graphs showing the behavior of a prosthetic foot while making a U-turn, as either the inside foot or outside foot.
Figure 62:
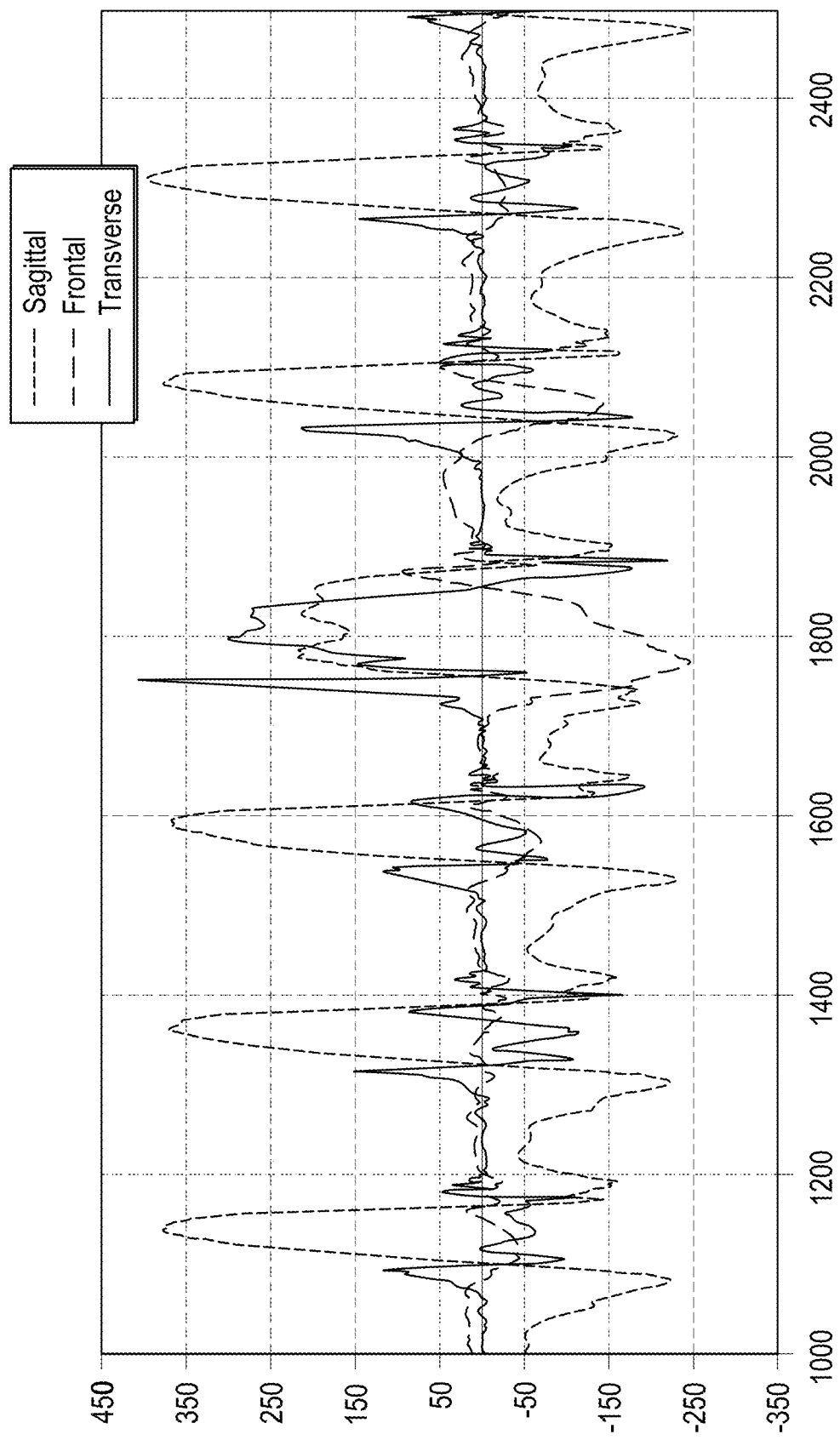

Sensors can also indicate when the user is changing direction, as shown in FIGS. 61 and 62, which shows gyroscopic measurements of angular velocity in the sagittal, coronal, and transverse planes during a U-turn, with the prosthetic foot being the inside foot (FIG. 61) or the outside foot (FIG. 62). As shown in the gait cycles before and after the U-turn, rotation in the sagittal plane dominates during normal walking. However, when a turn is being made, the foot experiences significant rotations in both the coronal and transverse planes. Thus, a comparison of angular velocity between the sagittal and coronal/transverse planes can be used to indicate a turning event. For example, if the angular velocity in the transverse or coronal plane is relatively high or more particularly higher than in the sagittal plane, this can indicate that a user is changing direction (perhaps at the end of a staircase or around a corner, or making a U-turn). The device can then transition-to or maintain level ground walking, and further can optionally set the joint angle to zero. Setting the joint angle to zero can minimize risk of falling during a complex motion such as turning by eliminating additional motion by the device.

The sensors can also be used to facilitate alignment of the prosthetic foot for a particular user and associated cosmesis, shoe, or other auxiliary device associated with the foot. For example, a range of motion of the prosthetic foot (such as a maximum dorsiflexion position and a maximum plantarflexion position) can be compared to idealized ranges of motion. Further, a heel and toe-load ratio during level ground walking can be measured and compared with idealized ratios (e.g., for every foot category and size). If the alignment is off, the heel height can be raised or lowered (either by a powered actuator, or by a static device such as a screw or other un-powered device as discussed further herein) to adjust the alignment (e.g., to change the range of motion or the neutral angle).

Additionally, the activity measured by these sensors, and other sensors described herein can be recorded for review at a later time. Additionally, the data can be time-stamped. The data can be retrieved at a later time by wired or wireless connections, and transferred to an auxiliary device. Alternatively, the data can be transferred in real-time, such as with a wireless connection to a user's mobile device.

The attachment member 10 can additionally include or define a cover 18. The cover 18 can protect various components of the prosthetic foot 1 such as electronics (as described above), the actuator 20 (describe below), or other components. In some embodiments the cover 18 can include open portions in the coronal plane, allowing flexibility of motion in the medial-lateral directions. In further embodiments the cover 18 can include open portions in the sagittal plane, allowing flexibility of motion in the anterior-posterior directions. In some embodiments, the open portions can be vertical or horizontal slots formed in the cover 18, to allow movement of pivot axles associated with any one of the connection portions 12, 14, 16.

Figure 1:
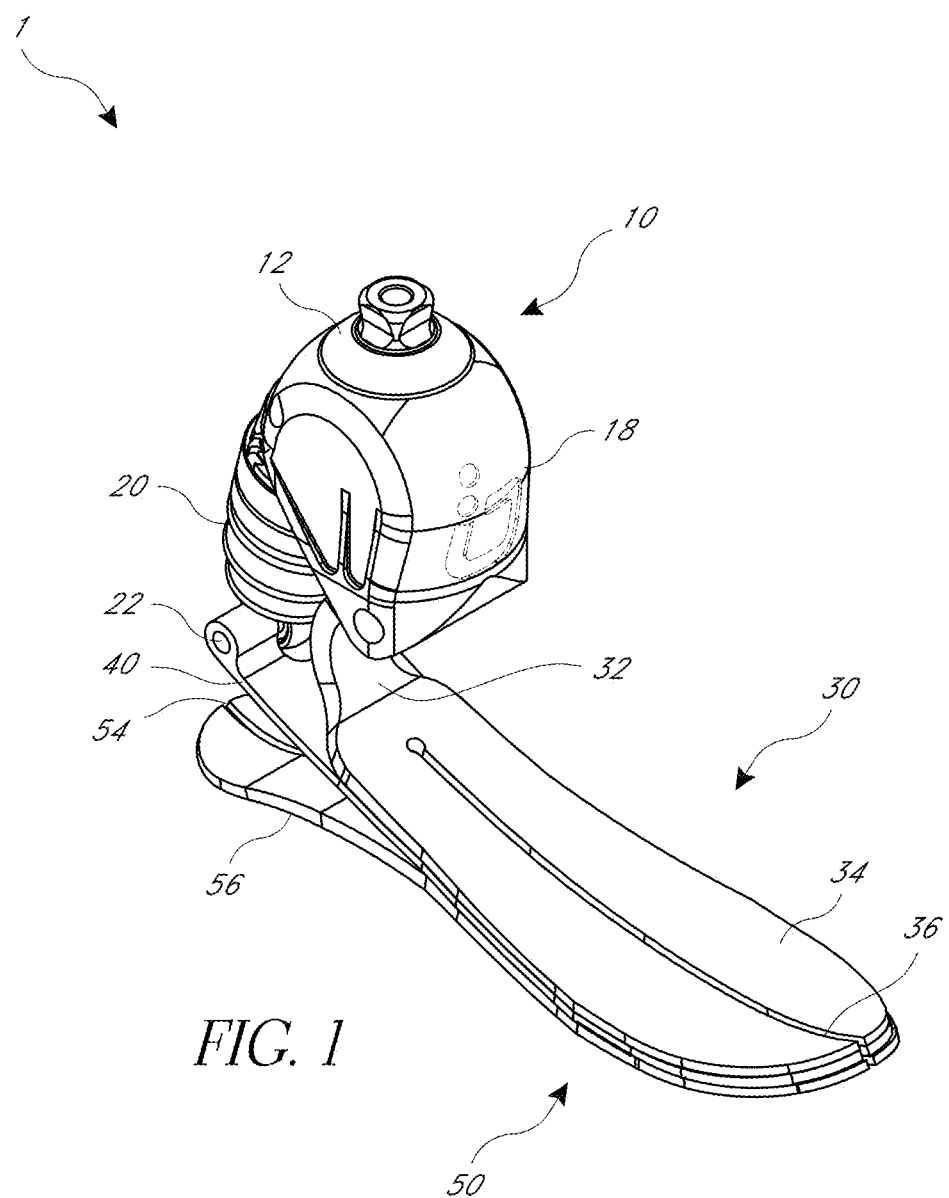
FIG. 1 is a perspective view of an embodiment of a prosthetic foot.
Figure 3:
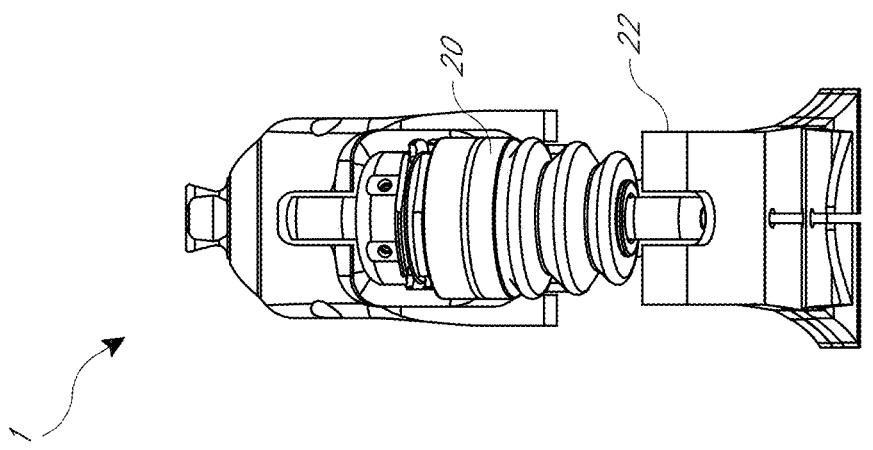
FIG. 3 is a rear view of the prosthetic foot of FIG. 1.
Figure 2:
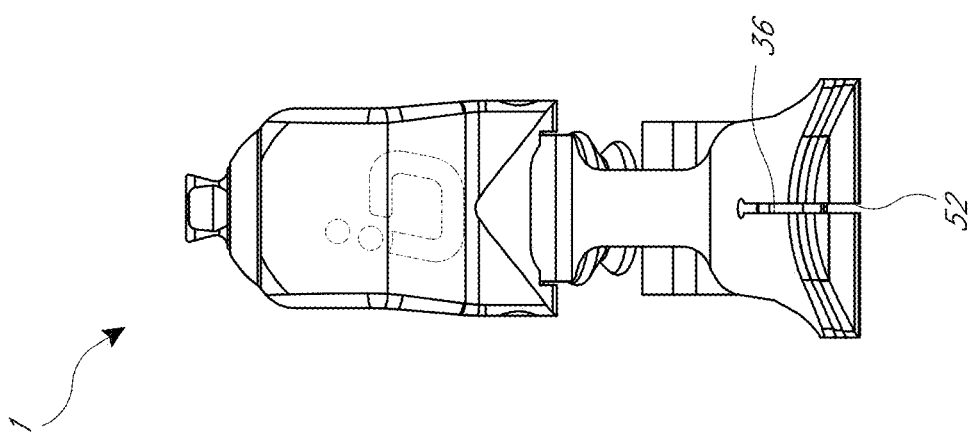
FIG. 2 is a front view of the prosthetic foot of FIG. 1.

As shown in FIG. 1, the attachment member 10 can connect to a first flexible member 30 at the third connection portion 16. In some embodiments the third connection portion 16 can provide a rotatable connection, although non-rotatable connections can also be used. In some embodiments, the rotation can be provided by an axle firmly mounted to the attachment member 10, about which the first flexible member 30 can rotate. In other embodiments, the first flexible member 30 can be fixed to the axle, and relative rotation can be allowed between the axle and the attachment member 30. In one embodiment, the first flexible member 30 can include or define a bushing or opening through which the axle extends. The first flexible member 30 can be formed from a sufficiently flexible material such as carbon fiber, though other suitable materials or combination of materials can be used (e.g., carbon and glass fibers). In other embodiments, the first flexible member 30 can be substantially inelastic, so as to provide a rigid connection. It will be understood that the other flexible members 40, 50 (described further below) can be formed of similar materials and have similar connections as the first flexible member 30.

Additionally, it will be understood that the flexible members 30, 40, 50 can include various films or coatings at least on their outer surfaces. The films can provide a variety of functions, such as reducing wear on the flexible members as they move against each other or other objects, reducing frictional forces, increasing traction with the ground or an intermediate structure between the flexible member and the ground, reducing noise from rubbing of the flexible members, and other functions. For example, in some embodiments a bottom surface of a flexible member intended to contact the ground or an intermediate structure between the member and the ground might have a toughening film and/or coating. Similarly, the bottom surface can include a film and/or coating that improves traction with the ground or an intermediate structure such as a shoe, sock, or cosmesis. Examples of films that can be used include, but are not limited to, films containing dry lubricants such as graphite and molybdenum disulfide (particularly, Dupont's DryFilm and Dow Corning's Molykote), soft metals, polytetrafluoroethylene (PTFE), vinyl, polyester, nylon, and epoxies.

Further, the first flexible member 30 can be formed into a shape configured to provide a desired flexibility or rigidity. As shown in FIG. 1, the flexible member 30 includes a C-shaped portion 32 at an upper portion (proximal portion) of the first flexible member, near the third connection portion 16. The C-shaped portion 32 is depicted as including an opening facing forward (e.g., the C-shaped portion 32 curves forwardly so that it is concave toward the front of the prosthetic foot), although in other embodiments the C-shaped portion can have an opening facing backward (e.g., the C-shaped portion can curve rearward so that it is concave toward the rear of the prosthetic foot). In some embodiments, the C-shaped portion 32 can bend more than 90 degrees, more than 110 degrees, 130 degrees, 150 degrees, or 170 degrees when unloaded. The bend of the C-shaped portion 32 can affect the resistance or flexibility of the first flexible member 30. Notably, this resistance or flexibility can be adjusted, as described further below. In other embodiments, the portion 32 can have other suitable shapes, such as generally L-shaped or angled relative to a toe portion of the prosthetic foot.

In the embodiment of FIG. 1, the flexible member 30 can extend from the lower portion of the C-shaped portion 32 into a foot portion 34. The foot portion 34 of the flexible member 30 can be substantially flat and extend from a rear portion of the prosthetic foot 1 toward a toe region of the prosthetic foot 1. The foot portion 34 can further include a slit 36. As shown in FIG. 1, the slit 36 extends longitudinally to a toe end of the flexible member 30 to separate the foot portion 34 into two or more foot members that can flex independently, although in some embodiments the slit 36 can be closed at the toe end (e.g., where at least one of the flexible members 30, 40, 50 are solid at a toe portion such that the slit terminates prior to the end of the at least one flexible member). As will be discussed further below, the slit 36 can allow the flexibility and resistance of the flexible member 30 to be altered. In another embodiment, the flexible members 30, 40, 50 can be monolithic without any slits.

As further shown in FIG. 4, the attachment member 10 can connect to an actuator 20 at the second connection portion 14. Like the third connection portion 16, the second connection portion 14 can be rotatable or non-rotatable. Notably, in FIG. 4 the third connection portion 16 is in a front portion of the attachment member 10, and the second connection portion 14 is in a rear portion of the attachment member 10. Similarly, the actuator 20 is located at a rear portion of the prosthetic foot 1. However, in other embodiments the actuator 20 can be positioned in a front portion of the prosthetic foot 1, as further described below.

The actuator 20 can be in a variety of forms and can be operated in a variety of ways, as described by way of example in U.S. patent application Ser. No. 11/367,049, issued Mar. 1, 2011 as U.S. Pat. No. 7,896,927, and U.S. patent application Ser. No. 12/816,968, published as U.S. 2010/0324698 on Dec. 23, 2010, each of which being incorporated by reference in their entirety herein and should be considered a part of this specification. For example, the actuator 20 can be a powered actuator such as a screw motor, or a passive member such as a flexible member (e.g., a spring) or a chamber with a magnetorheologic fluid, or can be a hydraulic or pneumatic system. In some embodiments, the actuator 20 can have an electric motor. The electric motor can have a power between approximately 60 W and 100 W). Further, the actuator 20 can be configured to operate in a variety of ways, as also discussed in Appendices A and B. For example, the actuator 20 can be configured to extend or contract to assist a user during a gait cycle. For example, the actuator 20 can change the orientation of the prosthetic foot 1 to dorsiflexion and then to plantarflexion during a swing phase of gait cycle so that the toe portion of the prosthetic foot 1 is raised during the initial portion of swing phase. In another embodiment, the actuator 20 can change the orientation of the prosthetic foot 1 to plantarflexion when the user is in a relaxed (e.g., sitting) position. Further, such motion of the actuator 20 can change the flexibility or resistance of the flexible members 30, 40, 50, as further described below. In some embodiments, the actuator 20 can also enter a low power mode (e.g., hibernation mode), such as a relaxed mode or an inactive mode. For example, the actuator 20 may enter a low power mode during stance, as the embodiments described herein can provide greater stability during stance, as further described below. Advantageously, the low power mode allows for the conservation of battery power used to power the actuator 20, allowing the actuator 20 to be operated for longer periods of time between battery charging.

Figure 4A:
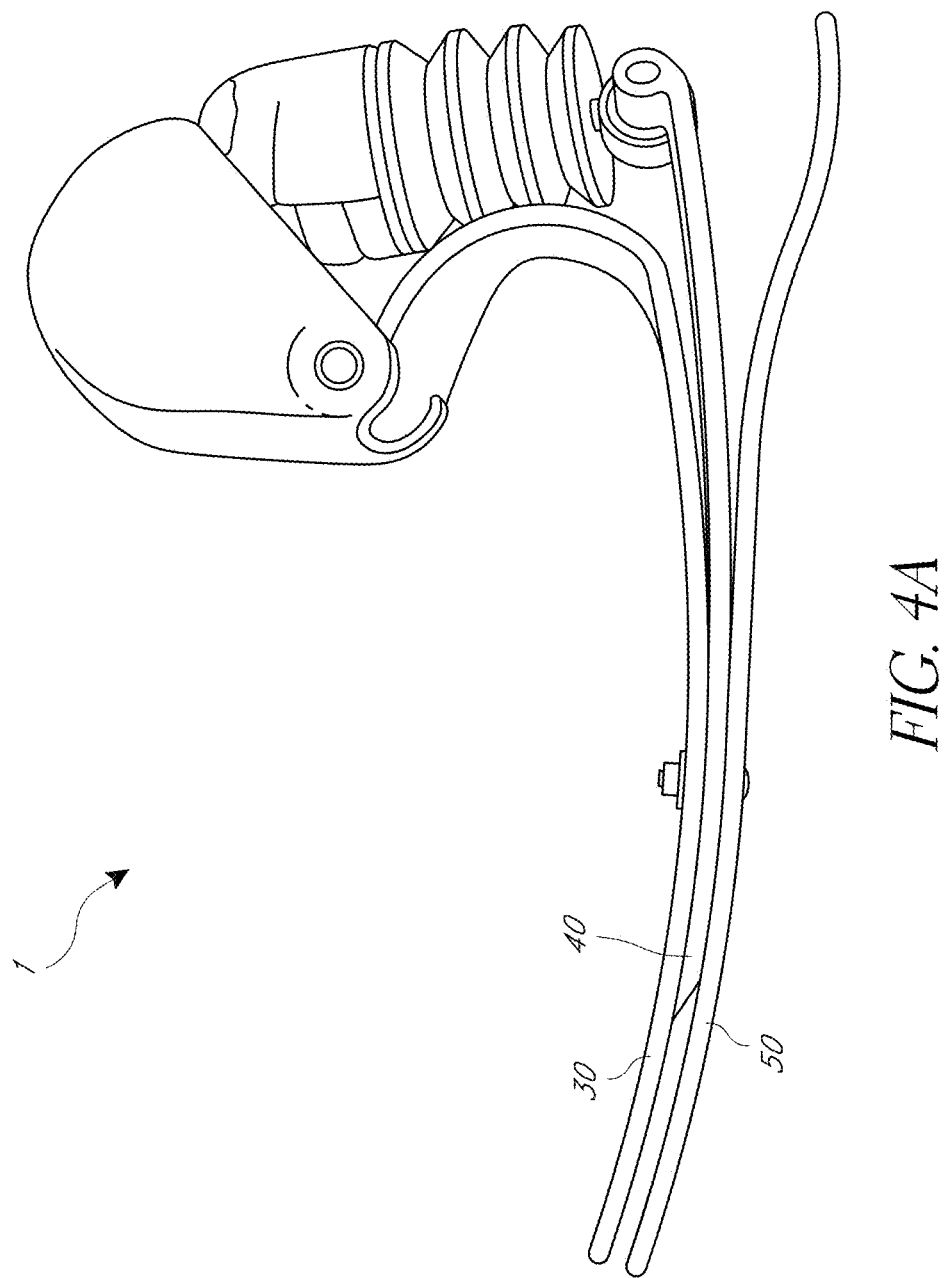
FIG. 4A is a side view of another embodiment of a prosthetic foot, similar to the prosthetic foot of FIG. 1.
Figure 5:
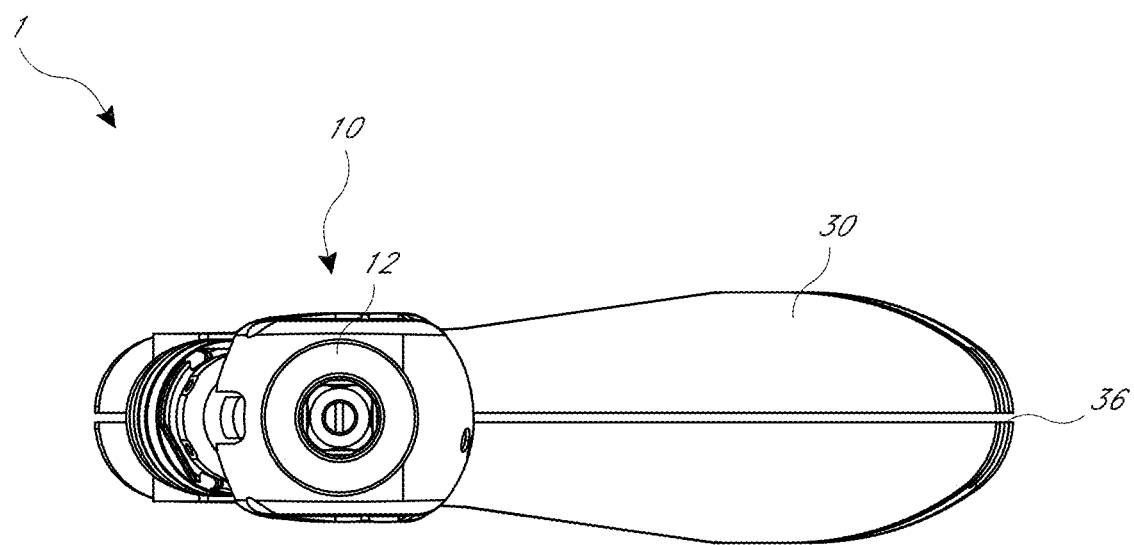
FIG. 5 is a top view of the prosthetic foot of FIG. 1.
Figure 6:
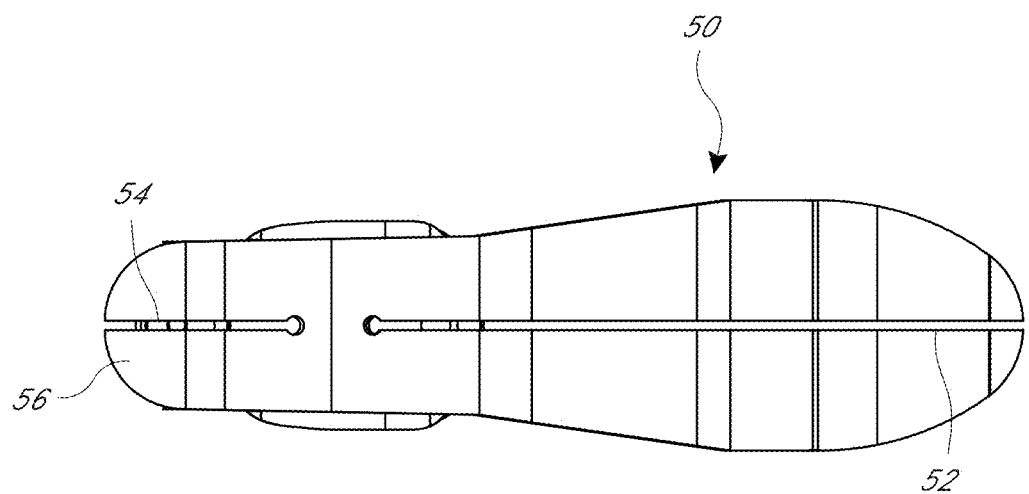
FIG. 6 is a bottom view of the prosthetic foot of FIG. 1.
Figure 8:
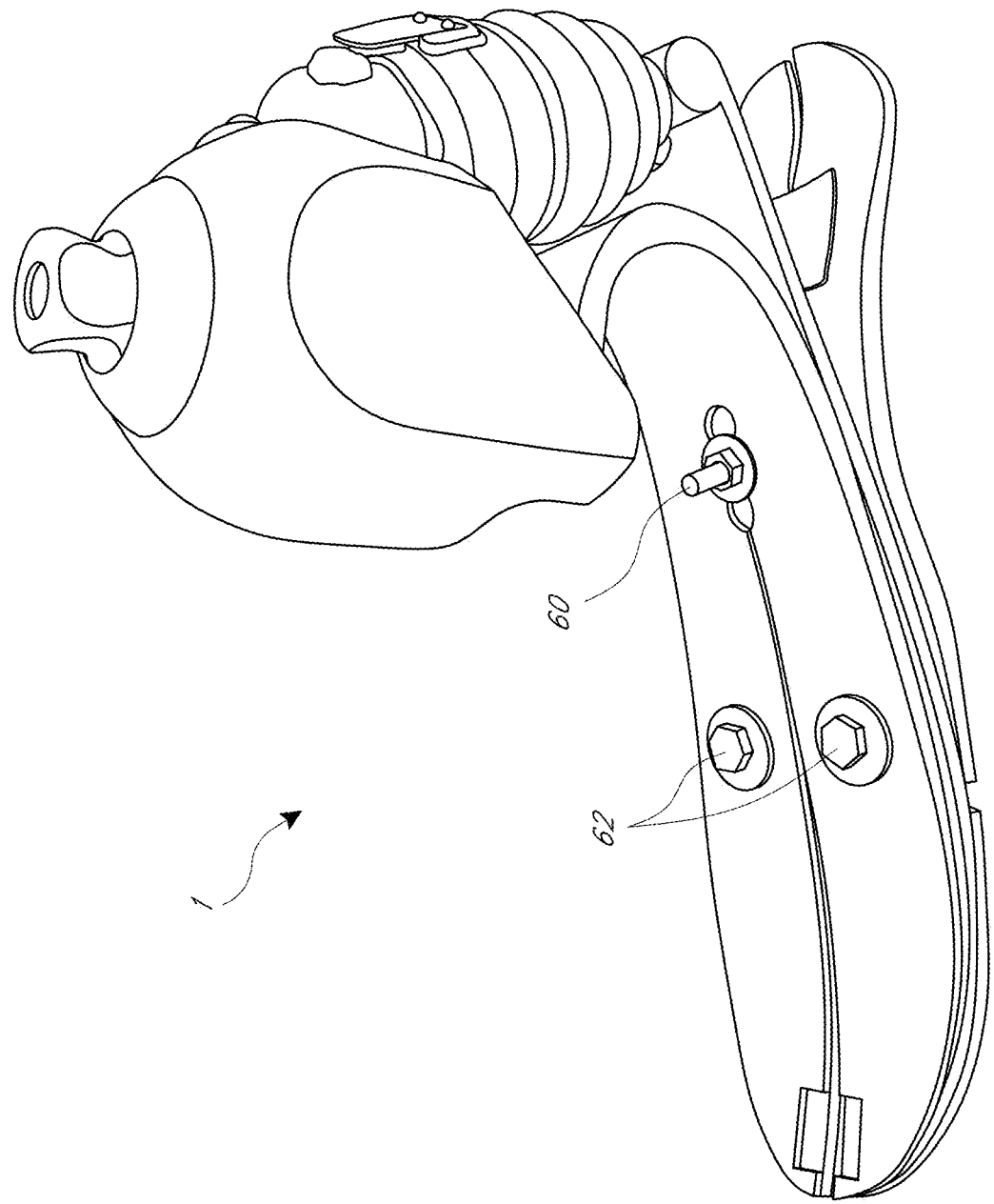
FIG. 8 is a view of the prosthetic foot of FIG. 1 with additional fasteners.
Figure 9:
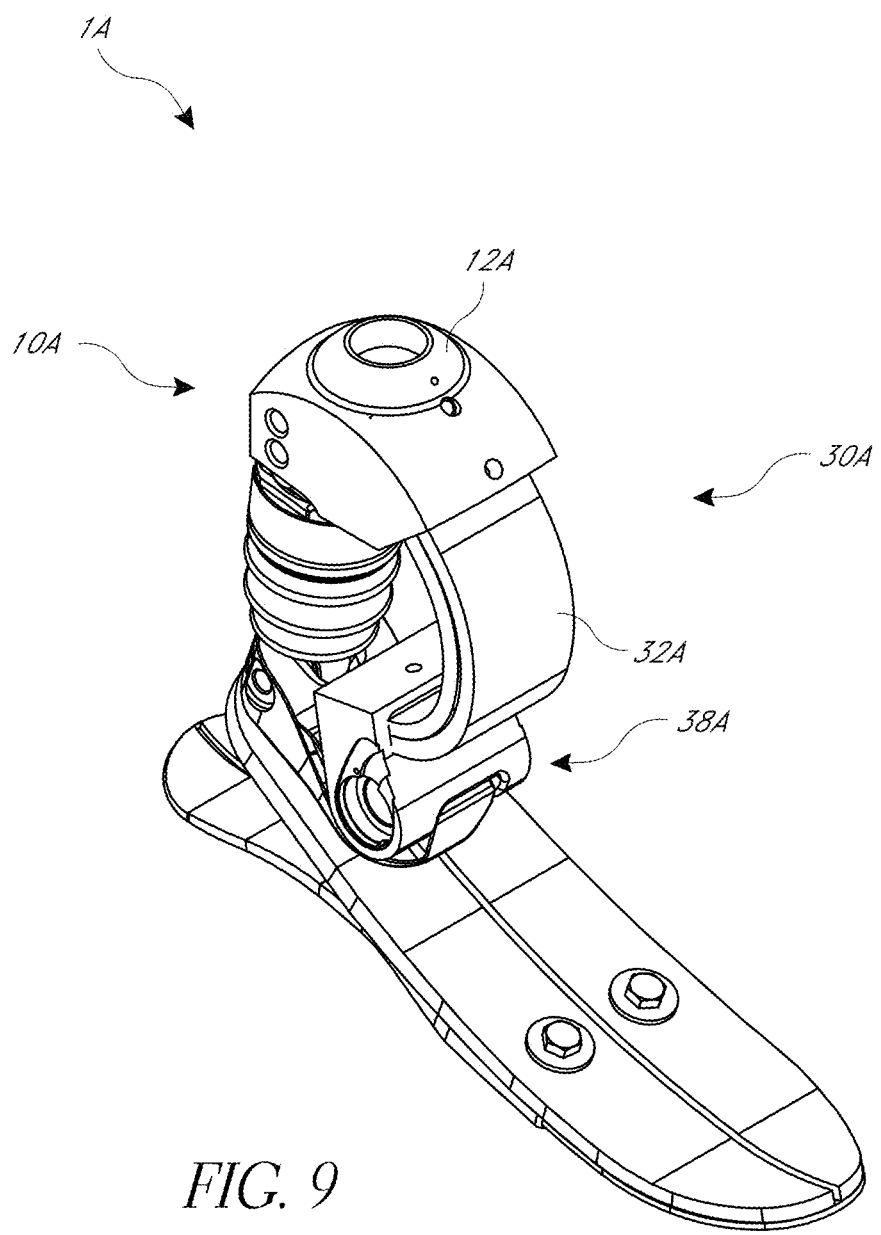
FIG. 9 is a perspective view of another embodiment of a prosthetic foot.
Figure 11:
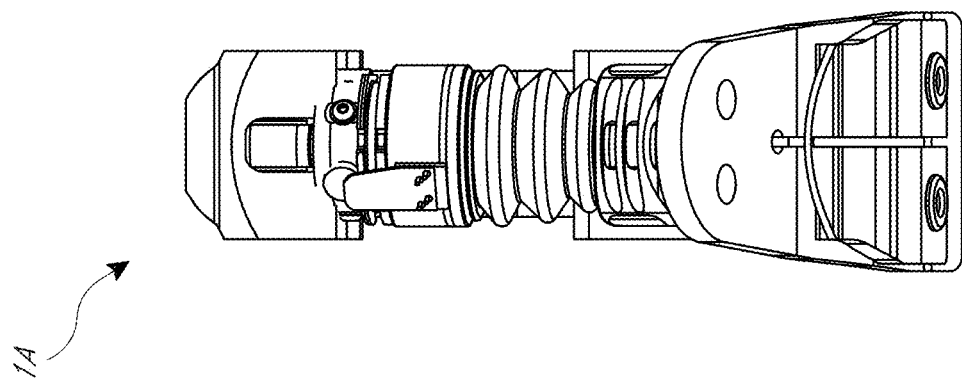
FIG. 11 is a rear view of the prosthetic foot of FIG. 9.
Figure 10:
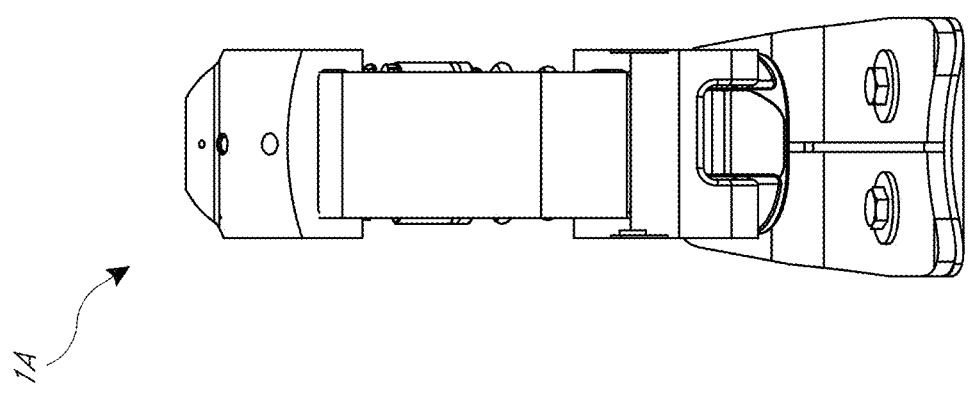
FIG. 10 is a front view of the prosthetic foot of FIG. 9.
Figure 12:
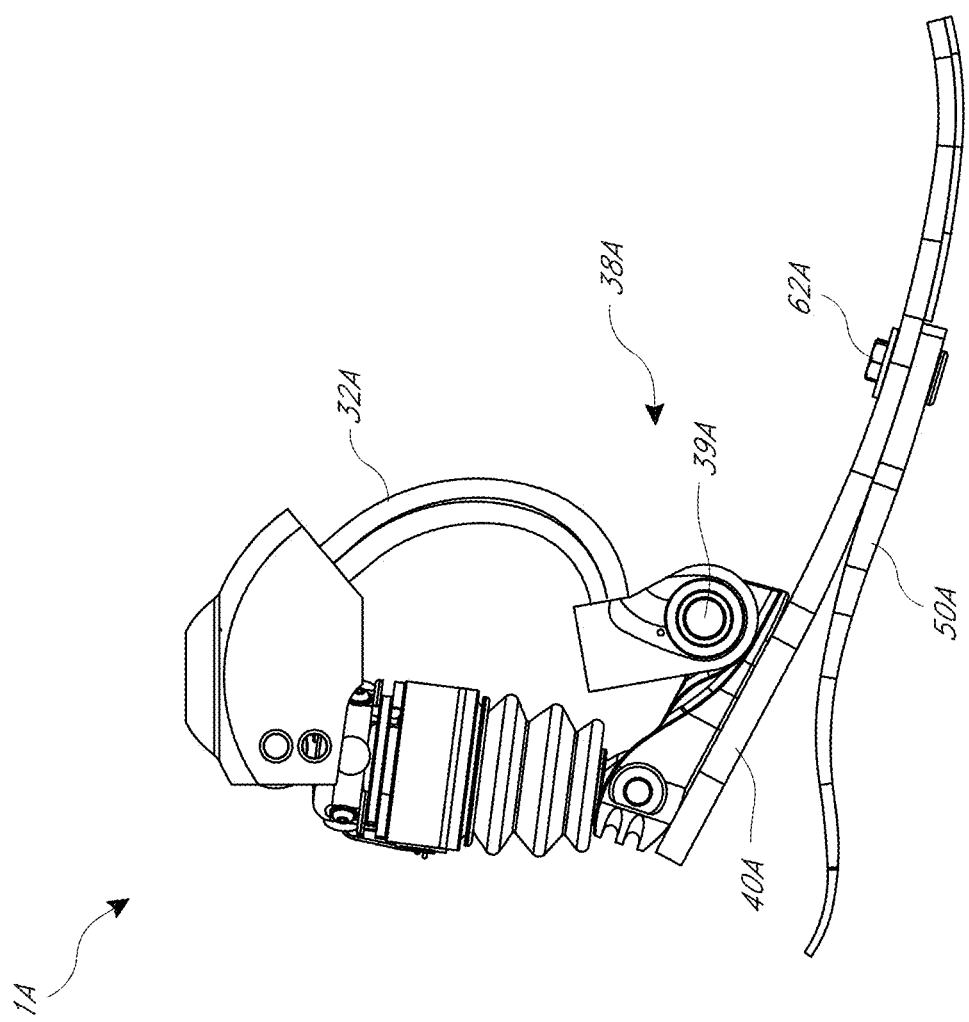
FIG. 12 is a side view of the prosthetic foot of FIG. 9.
Figure 13:
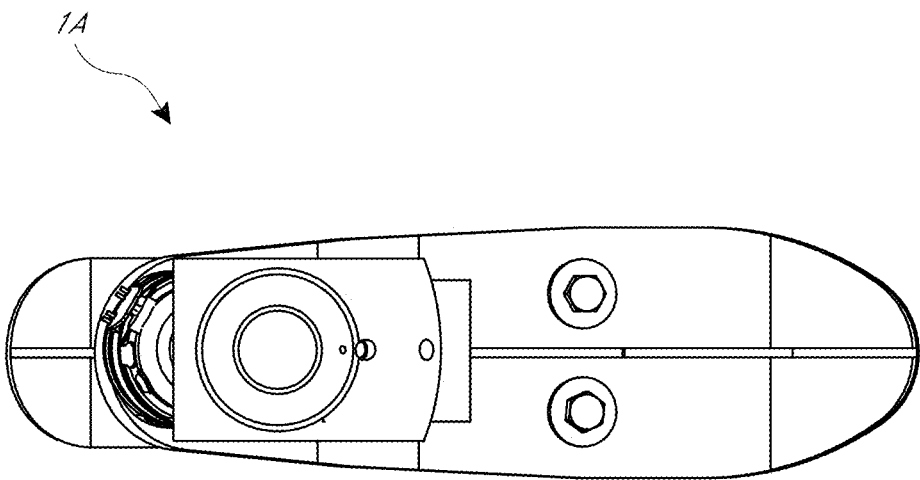
FIG. 13 is a top view of the prosthetic foot of FIG. 9.
Figure 14:
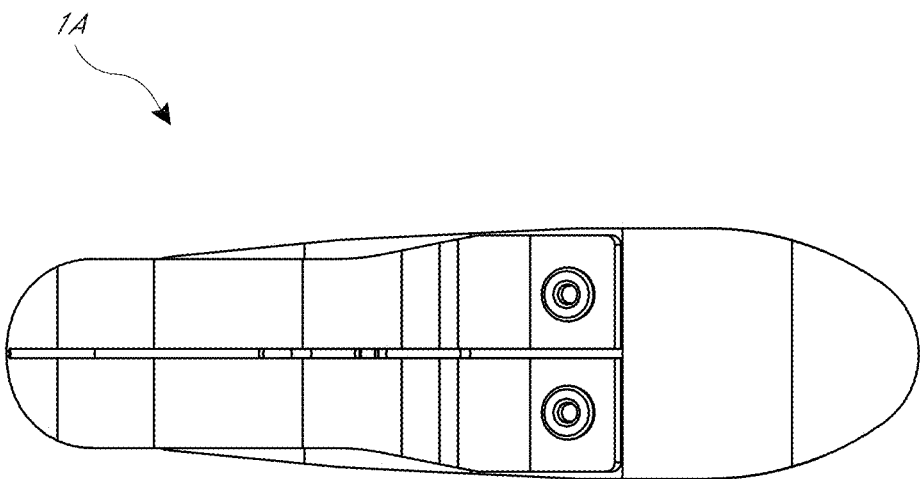
FIG. 14 is a bottom view of the prosthetic foot of FIG. 9.

Power can also be conserved, for example, by storing energy generated during ambulation. In some embodiments, the user's body weight can be used to load a spring during stance. The spring can then be held in the loaded position by a lock, ratchet, brake, or similar mechanism. The energy in the spring can then be used during toe-off by the prosthetic foot (e.g., to power a plantarflexion motion during toe-off). In other embodiments, a spring can be loaded by an actuator during a swing phase of the ambulation, held in The actuator 20 is depicted as connecting to a second flexible member 40 at a fourth connection portion 22. Like the second and third connection portions 14, 16, the fourth connection portion 22 can be rotatable or non-rotatable. In one embodiment, the second flexible member 40 can include or define a bushing or opening through which an axle extends to provide a rotatable connection or pivot axis between the second flexible member 40 and the actuator 20. The second flexible member 40 can extend into a foot portion in a manner similar to the foot portion 34 of the first flexible member 30. In one embodiment, the second flexible member 40 can extend to a distal end of the prosthetic foot 1, so that the first and second flexible members 30, 40 extend to generally the same location at the distal end of the prosthetic foot 1. Further, the second flexible member 40 can include a slit similar to the slit 36 of the first flexible member 30. Even further, the second flexible member 40 can be composed of materials similar to those for the first flexible member, such as carbon fiber. As shown, the second flexible member 40 is disposed below the first flexible member 30, and extends tangentially forward and toward the first flexible member to abut the first flexible member 30 along the foot portion 34 of the first flexible member 30. Although the first and second flexible members 30, 40 are depicted as ending at approximately the same point at a toe portion of the prosthetic foot, in some embodiments the first flexible member 30 may extend further, or the second flexible member 40 may extend further. For example, as depicted in FIG. 4A, the first and third flexible members 30, 50 can extend further than the second flexible member 40, creating a gap between the first and third flexible members 30, 50. In other embodiments, a gap can be provided between the first and second flexible members 30, 40 in a toe region of the prosthetic foot, as shown in FIG. 8. As a further example, as depicted in, for example, FIG. 12 the third flexible member 50 (e.g., member 50A, described below) can end before a toe portion of the prosthetic foot 1, such as at a metatarsal region of the foot. The first and/or second flexible members 30, 40 (e.g., only second flexible member 40A in FIG. 12) can then extend past the third flexible member 50 to the toe portion.

The prosthetic foot 1 can further include a third flexible member 50. As shown, the third flexible member 50 can extend from a heel portion 56 (e.g., a cantilevered or free end) at a bottom and rear portion of the prosthetic foot 1. This heel portion 56, as shown, can be spaced from the actuator 20 and the second flexible member 40, curving downward toward and away from the actuator 20. From the heel portion 56, the third flexible member 50 can extend to a toe portion of the prosthetic foot 1, and can generally abut the foot portion second flexible member 40, as that member abuts the first flexible member 30. Further, the third flexible member 50 can have a slit along this foot portion that generally matches the slits in the first and second flexible members 30, 40. Additionally, as shown, the third flexible member 50 can include a heel slit 54 in the heel portion 56 of the flexible member.

As shown in the figures, the slit 36 in the first flexible member 30 can align with the slit in the second flexible member 40 and a slit 52 in the third flexible member 50 in the foot portion 34. In one embodiment, the prosthetic foot 1 can have a stiffness control member 60 that can be actuated to vary the stiffness of the prosthetic foot. In some embodiments, the stiffness control member 60 can be a fastening member 60 (e.g., bolt and nut, clamp, staple, rivet, etc.) that couples two or more of the flexible members 30, 40, 50 to each other, where the fastening member 60 can travel along the slit 36 or a slot defined at least partially by the slit, best shown in FIG. 8, or travel along a slot in the flexible members 30, 40, 50 where the flexible members do not have a slit. Attachment can be provided between the flexible elements 30, 40, 50, for example, generally in a metatarsal region of the prosthetic foot 1. Advantageously, in some embodiments the fastening member's 60 position can be adjustable along the length of the slit 36. For example, when the fastening member 60 is a bolt and nut, the bolt can be moved to any desired position along the slit 36 and then fastened into place by tightening the nut. In some embodiments, an undercut or recess in the flexible members 30, 40, 50 can be provided to prevent the bolt and nut from protruding outwards. Notably, the position of the fastening member along the slit 36 can alter the flexibility and resistance of the flexible members 30, 40, 50. Where the flexible members 30, 40, 50 are not held together (e.g., by the fastening member) they can separate and act as distinct flexible members instead of combining into a single flexible member where held together. Thus, if the fastening member 60 is moved forward, the flexible members 30, 40, 50 are held together over a shorter range, allowing more separation between them, and thus greater flexibility (e.g., the lever arm of the second flexible member 40 is relatively longer, resulting in greater flexibility of the prosthetic foot 1). Alternatively, if the fastening member is moved rearward, the flexible members 30, 40, 50 are held together over a longer range, reducing the allowed separation and flexibility (e.g., the lever arm of the second flexible member 40 is relatively shorter, resulting in increased stiffness of the prosthetic foot 1). Advantageously, the fastening member 60 can be adjusted to vary the stiffness of the prosthetic foot 1.

In some embodiments, the stiffness control member 60 can be mechanically actuated, either manually by the user or automatically (e.g., actively adjusted) during ambulation by the user (e.g., based on the activity level of the user or the phase of gait cycle).

Notably, as discussed above, in some embodiments, the flexibility and resistance of the flexible members 30, 40, 50 can also be altered by the actuator 20 (independently of, or in combination with, the stiffness control member 60). Thus, it will be understood that the flexibility and resistance of the flexible members 30, 40, 50 can be altered manually and/or by an actuator. In further examples, the stiffness control member 60 can be moved (e.g., automatically moved) by an actuator to adjust the resistance and flexibility of the flexible members 30, 40, 50.

In some embodiments, it may be preferable to adjust the flexibility and resistance of the flexible members 30, 40, 50 to reduce resistance and increase flexibility while moving on level ground. Thus, for example, the stiffness control member 60 can be moved forward while ambulating on level ground to provide faster plantarflexion after heel strike. During other gait patterns, such as walking downstairs, one can reduce flexibility and increase resistance by moving the stiffness control member 60 backward. In some embodiments, these gait patterns can be detected by sensors and processors provided on or in communication with the prosthetic foot 1. An actuator can then be controlled to adjust the flexibility and resistance of the flexible members 30, 40, 50 according to the detected gait pattern.

Variations to the embodiment in FIGS. 1-8 are possible. For example, in the depicted embodiment a stiffness control member 60 (e.g., fastening member 60) can be moved to various positions along the slit 36, such that the resistance and flexibility of the flexible members 30, 40, 50 can be varied. However, in other embodiments it may be preferable to remove the slit 36 such that the flexible members 30, 40, 50 are more solid and provide a more uniform resistance. Further, in some embodiments it may be preferable to bond the flexible elements 30, 40, 50 in another manner, such as with an adhesive, so they remain permanently attached. The flexible elements 30, 40, 50 can also be held together with additional fastening members 62, depicted as nuts and bolts in FIG. 8, in addition to the adjustable fastening member 60. In other embodiments, one or more of the flexible elements 30, 40, 50 can be formed together into a single piece. For example, in some embodiments the second and third flexible members 40, 50 can be formed as a single piece.

In further embodiments this resistance can be varied by other methods. For example, in some embodiments the stiffness control member can be a wedge or insert that can be inserted where two or more of the flexible members 30, 40, 50 meet. For example, a wedge can be inserted between the first and second flexible members 30, 40 (e.g., above the second and below the first). Similarly, a wedge can be inserted between the second and third flexible members 40, 50, such as at a wedging location 64, depicted in FIG. 4. The wedge can limit the range of motion of the flexible members 30, 40, 50 relative to each other, thus increasing their resistance. The size and shape of the wedge can be chosen to cause a particular desired resistance. Further, the wedge can be moved forward or rearward to vary the flexibility and resistance between the flexible members 30, 40, 50. The wedge can also provide additional structural support, preventing the flexible members 30, 40, 50 from breaking when over-loaded or shock-loaded. Advantageously, such wedges can also be removable, such that a user can easily take them in or out depending on their desired activity.

The depicted embodiment also combines three separate flexible elements 30, 40, 50 that each provide a separate function. For example, the first flexible element 30 acts as a spring in parallel with the actuator 20. Further, the second flexible element 40 acts as a spring in series with the actuator 20. Both flexible elements 30, 40 can thus be configured to work with or against the actuator 20 at different phases of the gait cycle. Further, the flexible elements 30, 40 can be loaded or unloaded by the actuator 20. Providing one spring in parallel and the other in series allows each spring to have a different effect on the dynamics of the prosthetic foot 1 during movement. For example, during heel strike, the actuator 20 and second flexible member 40 can act in series to provide the prosthetic foot 1 with a certain level of flexibility in addition to the energy stored by the third flexible member (e.g., be relatively less stiff at heel-strike), while during toe-off, the actuator 20 and first flexible element 30 can act in parallel to provide the prosthetic foot with a different level of flexibility (e.g., be relatively more stiff at toe-off). Thus, the independent flexibility and resistance of the flexible elements 30, 40 can be chosen separately to optimize the behavior of the prosthetic foot 1.

Notably, in the depicted embodiment the first and second flexible members 30, 40 both extend toward the toe along the foot portion 34. However, they do not extend toward the heel of the prosthetic foot 1. The third flexible member 50 includes a heel portion 56. The heel portion 56 thus provides flexibility and resistance to the prosthetic foot 1 during heel strike. This response during heel strike can be determined independently of a flexibility and resistance during toe-strike or toe-off during a gait cycle, as the third flexible element 50 is a separate piece from the first and second flexible elements 30, 40. Thus, for example, a system of separate flexible members 30, 40, 50 can include versions of each flexible member with varying flexibilities and resistances. One can then choose each flexible member 30, 40, 50 to provide a desired flexibility and resistance at different times during a gait cycle, depending on the needs of a particular user.

In further embodiments, the actuator 20 can be removed or replaced with a rigid member. For example, in some embodiments the second flexible member 40 can connect directly to the second connection portion 14. In such embodiments, the first and second flexible members 30, 40 can both be rotatably connected to the attachment member 10. Further, in embodiments where the second flexible member 40 does not connect directly to the second connection portion 14, it can still rotatably connect to an intermediary member (such as a rigid member replacing the actuator 20) at a fourth connection portion 22 (as described above). In such embodiments, the three rotatable connections 14, 16, 22 can form a triangle with at least one flexible portion, the flexible portion being both the first and second flexible members 30, 40, between the fourth connection portion 22 and the third connection portion 16.

The rotatable connections 14, 16, 22 with the flexible members 30, 40 can provide a flexible resistance to rotation of the attachment member 10. Advantageously, the use of both first and second flexible members 30, 40 can provide for a natural rocking motion during stance that can provide improved stability with the prosthetic foot 1. This stability can also be provided in embodiments that include an actuator 20, e.g., when the actuator 20 is locked in a particular position or is substantially inactive.

FIGS. 9-15 depict a second embodiment of a prosthetic foot 1A. It will be understood that the prosthetic foot 1A in these figures has features similar to the prosthetic foot 1 described above, and thus will be described in terms of its differences. As shown, the prosthetic foot 1A includes a first flexible member 30A having a C-shaped portion 32A, similar to that in the previously described embodiments. However, in the present embodiment the C-shape portion 32A can be reversed to have an opening facing rearward (e.g., the C-shaped portion 32A has a concave shape facing toward the rear of the prosthetic foot 1). Further, as shown, the first flexible member 30A can include two parallel flexible pieces. Additionally, as shown, the first flexible member 30A can attach to the attachment member 10A at a second connection portion 14A that is non-rotatable, although in other embodiments the second connection portion 14A can be rotatable (e.g., via a pivot location, as shown in previous embodiments). Further, as shown, the first flexible member 30A can be shortened to not include a foot portion, like the foot portion 34 in the previous embodiments. Instead, the first flexible member 30A can attach to a fifth connection body 38A, also via a non-rotatable connection. However, the fifth connection body 38A can provide a rotatable connection to the second flexible member 40A, as shown in the figures, via a supplemental connection body 39A that can be considered to be part of the fifth connection body 38A.

Figure 15:
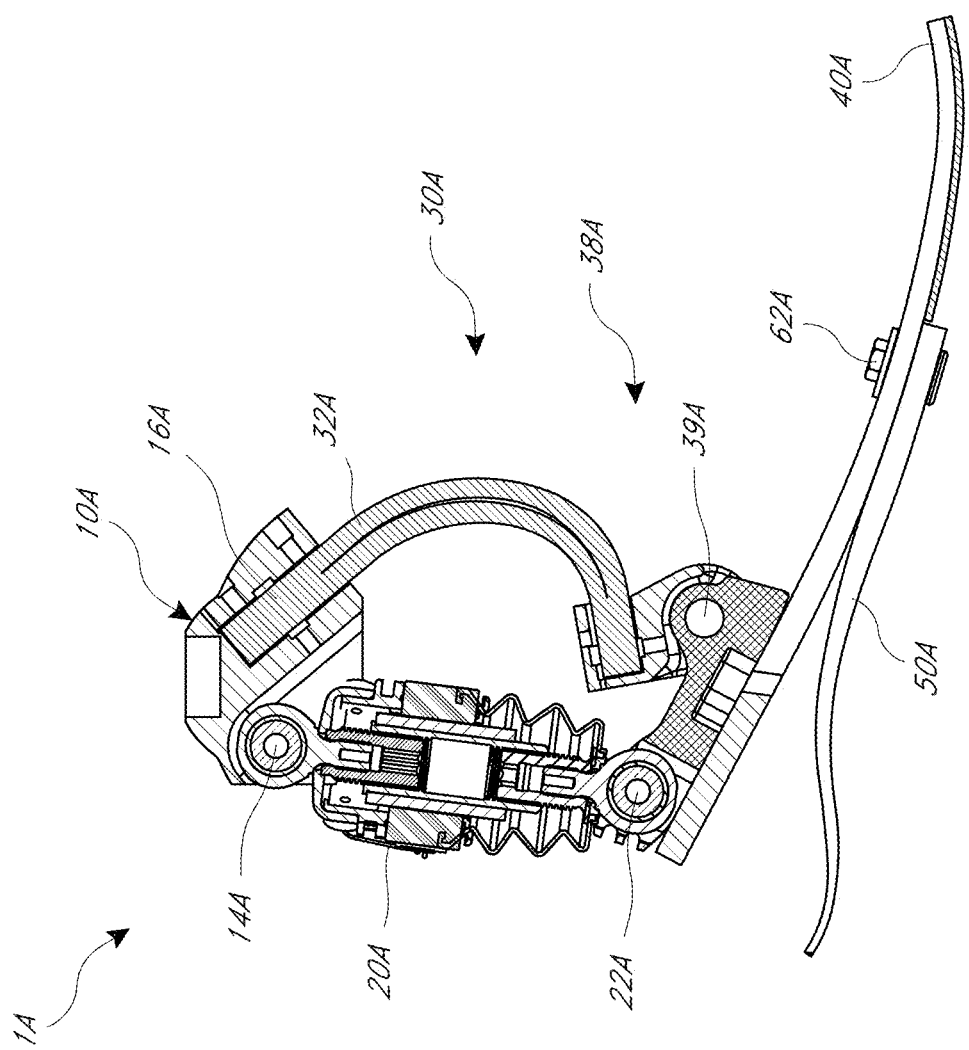
FIG. 15 is a cross-sectional side view of the prosthetic foot of FIG. 9.

Notably, the features in the embodiment in FIGS. 9-15 also form a triangle with at least one flexible portion and three rotatable connections, similar to that discussed above in the previous embodiment. For example, as best shown in FIG. 15, the prosthetic foot 1A includes a second connection portion 14A between the attachment member 10A and the actuator 20A. The actuator 20A can include a fourth connection portion 22A, connecting to the second flexible member 40A. The second flexible member 40A can connect to the first flexible member 30A with fifth connection body 59A. The first flexible member 30A can attach to the attachment member 10A, completing the triangle. In some embodiments, only one portion of the triangle can have a flexible portion. For example, in some embodiments the second flexible member 40A can be an inelastic or rigid member.

Figure 15A:
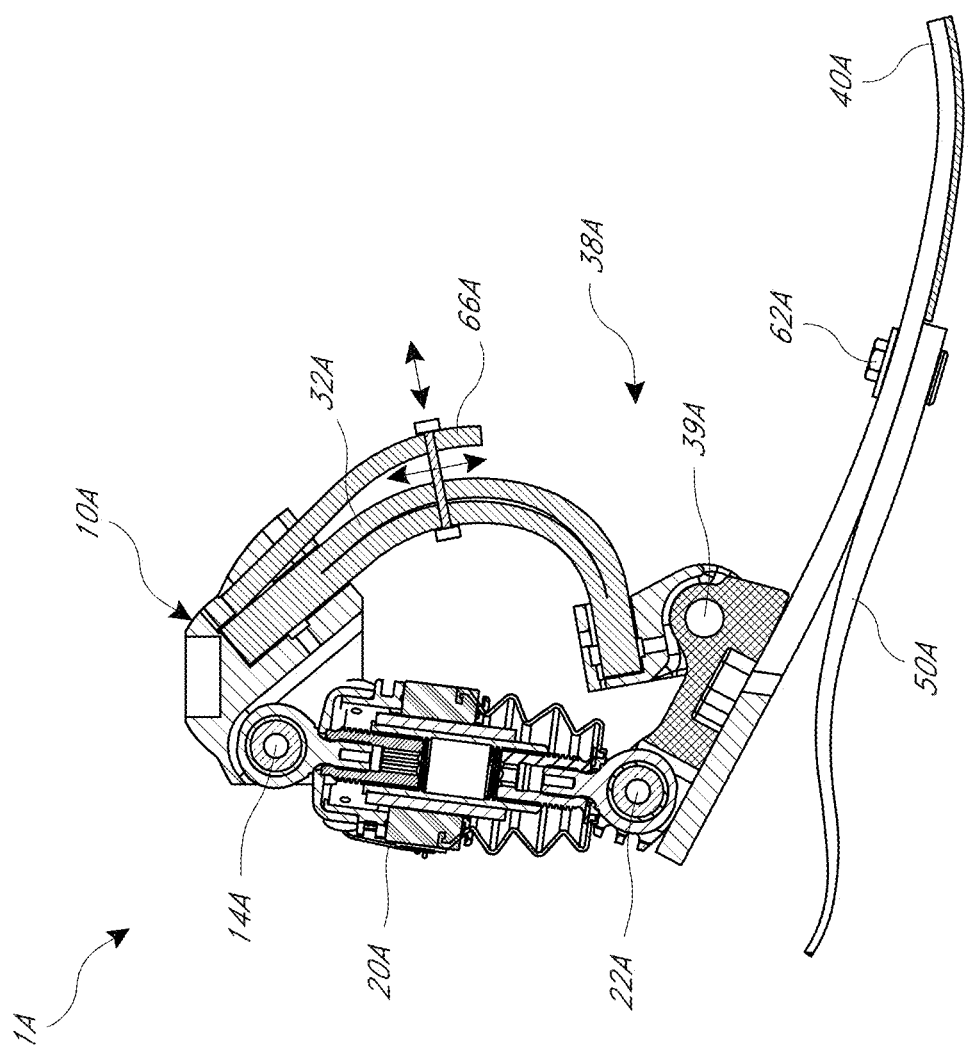
FIG. 15A is a cross-sectional view of another embodiment of a prosthetic foot, similar to the prosthetic foot of FIG. 9.
Figure 16:
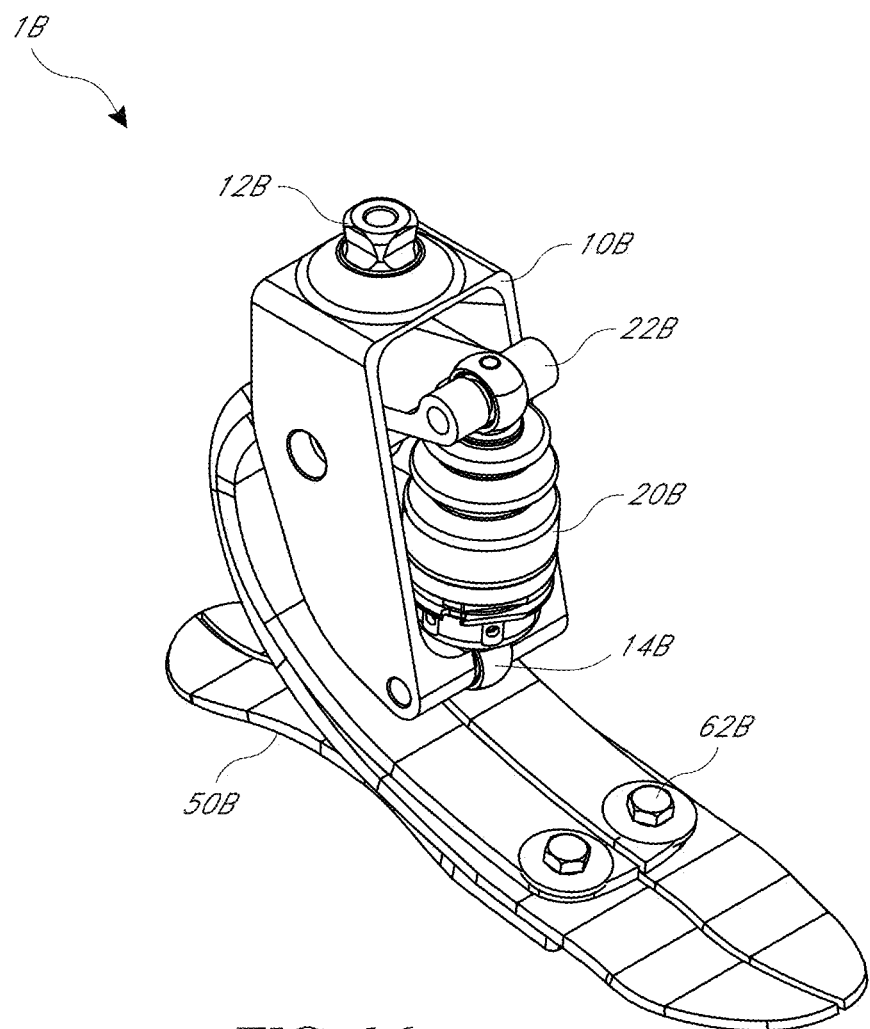
FIG. 16 is a perspective view of another embodiment of a prosthetic foot.
Figure 18:
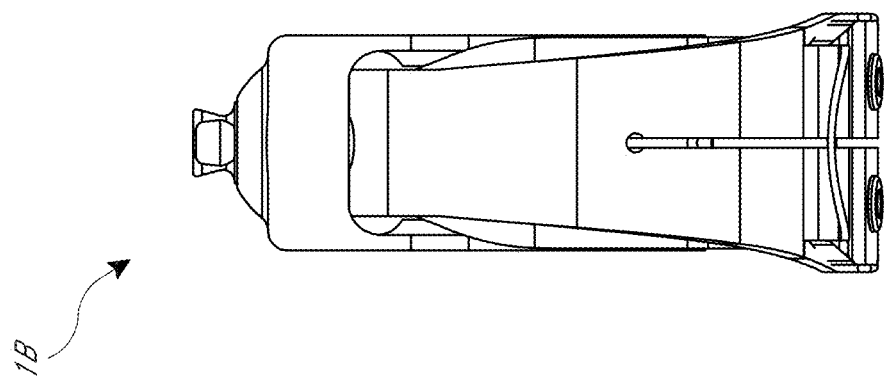
FIG. 18 is a rear view of the prosthetic foot of FIG. 16.
Figure 17:
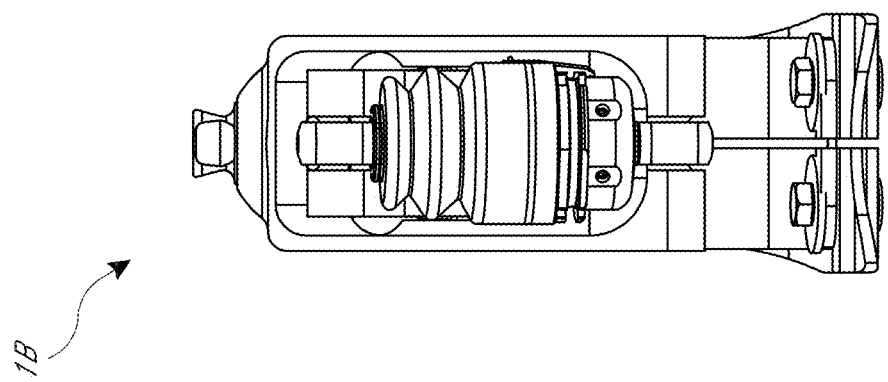
FIG. 17 is a front view of the prosthetic foot of FIG. 16.
Figure 19:
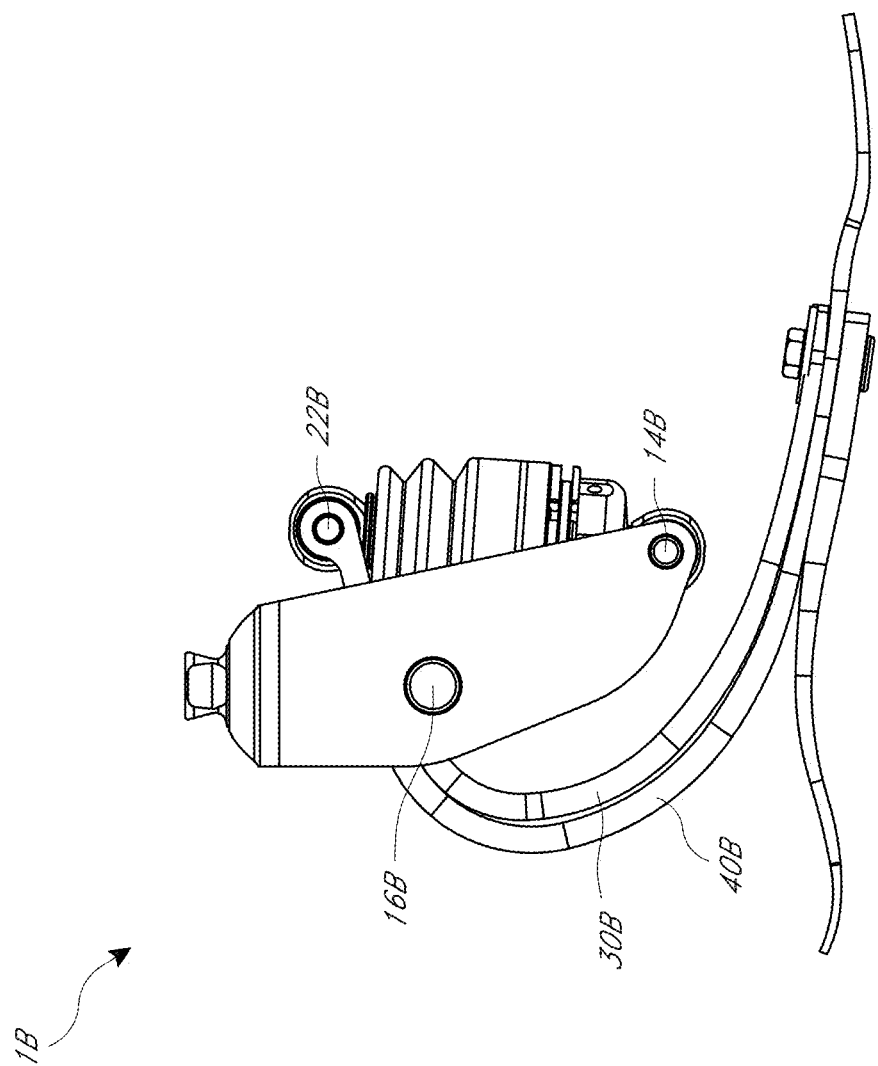
FIG. 19 is a side view of the prosthetic foot of FIG. 16.
Figure 20:
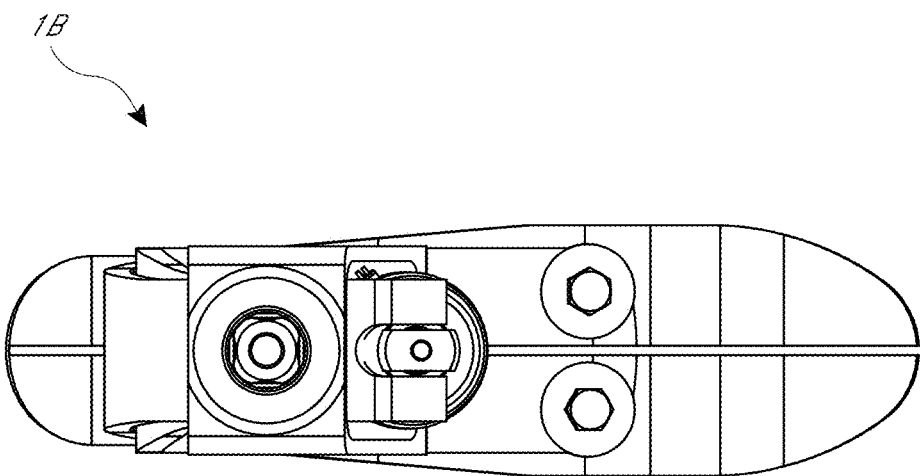
FIG. 20 is a top view of the prosthetic foot of FIG. 16.
Figure 21:
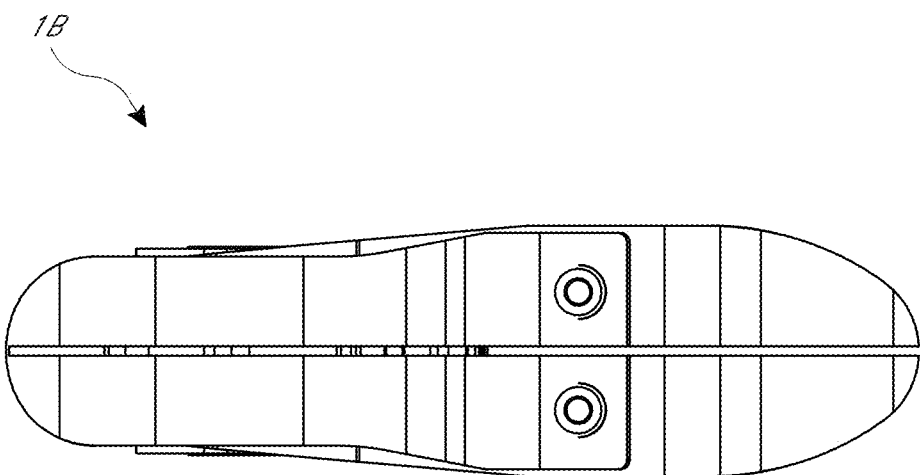
FIG. 21 is a bottom view of the prosthetic foot of FIG. 16.

Further, in some embodiments the C-shaped portion 32A can be substantially similar to that shown in FIGS. 9-15, but include an additional flexible member 66A generally aligned with the C-shaped portion 32A, as best shown in FIG. 15A. The additional flexible member 66A can connect to the attachment member 10A in a manner similar to the first flexible member 30A. The additional flexible member 66A can then extend tangent with the first flexible member 30A along the C-shaped portion 32A and terminate at a free end unattached to the fifth connection body 39A. A stiffness control member similar to the stiffness control member 60 can then be provided between the C-shaped portion 32A and the additional flexible member 66A. For example, slits can be provided in the C-shaped portion 32A and the additional flexible member 66A to receive a fastening member that can be moved along the length of the slit to adjust the flexibility and resistance of the C-shaped portion 32A, as illustrated. In further embodiments, such adjustability of the flexibility and resistance of the flexible members 30A, 40A, 50A can be provided with other suitable mechanisms. For example, in some embodiments the fifth connection body 38A (including the supplemental connection body 39A) can be movable in an anterior-posterior direction along the second flexible member 40A to change the location of the fifth connection body 38A on the second flexible member 40A. For example, in some embodiments the second flexible member 40A can include a slot that can receive a fastener to fasten the fifth connection body 38A in place along the second flexible member. However, other suitable mechanisms can be used to adjust the location of the fifth connection body 38A relative to the second flexible member 40A (e.g., a track and worm gear arrangement).

Additionally, the depicted prosthetic foot 1A depicts an alternative method for attaching the second and third flexible members 40A, 50A. As shown, these members can be attached by two bolts 62A, on opposite sides of the slit 36A. However, it will be understood that other attachment methods can be used, such as those described above. Further, an adjustable fastening member can be provided in the slit 36A, as discussed above, to vary the flexibility and resistance of the prosthetic foot 1A.

FIGS. 16-23 depict yet another embodiment of a prosthetic foot 1B. It will again be understood that the prosthetic foot 1B in these figures has features similar to the prosthetic foot 1 described above, and thus will be described in terms of its differences. As shown, the prosthetic foot 1B provides a design with the actuator 20B in a forward portion of the prosthetic foot. As shown, the attachment member 10B can still attach to the first flexible element 30B at a rotatable third connection portion 16B. However, the third connection portion 16B can be provided at an upper rear portion of the attachment member 10B. The second connection portion 14B can connect to the actuator 20B at a lower forward portion of the attachment portion 10B. The actuator 20B can then extend upwards from the second connection portion 14B to attach to the second flexible member 40B. The second flexible member 40B can then form a C-shaped portion that follows the forward-facing C-shaped portion 32B in the first flexible member 30B.

Connection of the third flexible member 50B is depicted as being substantially similar to the third flexible member 50A depicted in FIGS. 9-15. Similar variations can also be provided, as discussed above. Further, as shown, the first flexible member 30B can extend to a foot portion 34A and attach to the second and third flexible members 40B, 50B by the same bolts 62B. Further, as shown, the second flexible member 40B can extend beyond the first and second flexible members 30B, 50B, to a toe portion of the prosthetic foot 1B.

Notably, as shown in this embodiment, the first and third flexible members 30B, 50B can end substantially at the location of the bolts 62B. This can aid flexing of the second flexible member 40B in a toe region of the prosthetic foot 1B. Thus, the toe region can be made more flexible than the middle and heel regions of the prosthetic foot 1B.

In further embodiments, the bolts 62B can be angled into the coronal plane (i.e., the bolts 62B can be aligned on a plane that extends at an angle to a longitudinal axis of the prosthetic foot 1B). This angling can follow the angle of a natural metatarsal joint, facilitating the guiding of roll-over of the prosthetic foot 1B (e.g., toward the medial side) during use. This arrangement of the bolts (e.g., aligned along a plane at an angle to the longitudinal axis of the prosthetic foot and generally corresponding to the angle of a natural metatarsal joint) can be provided in other prosthetic foot embodiments disclosed herein.

Figure 22:
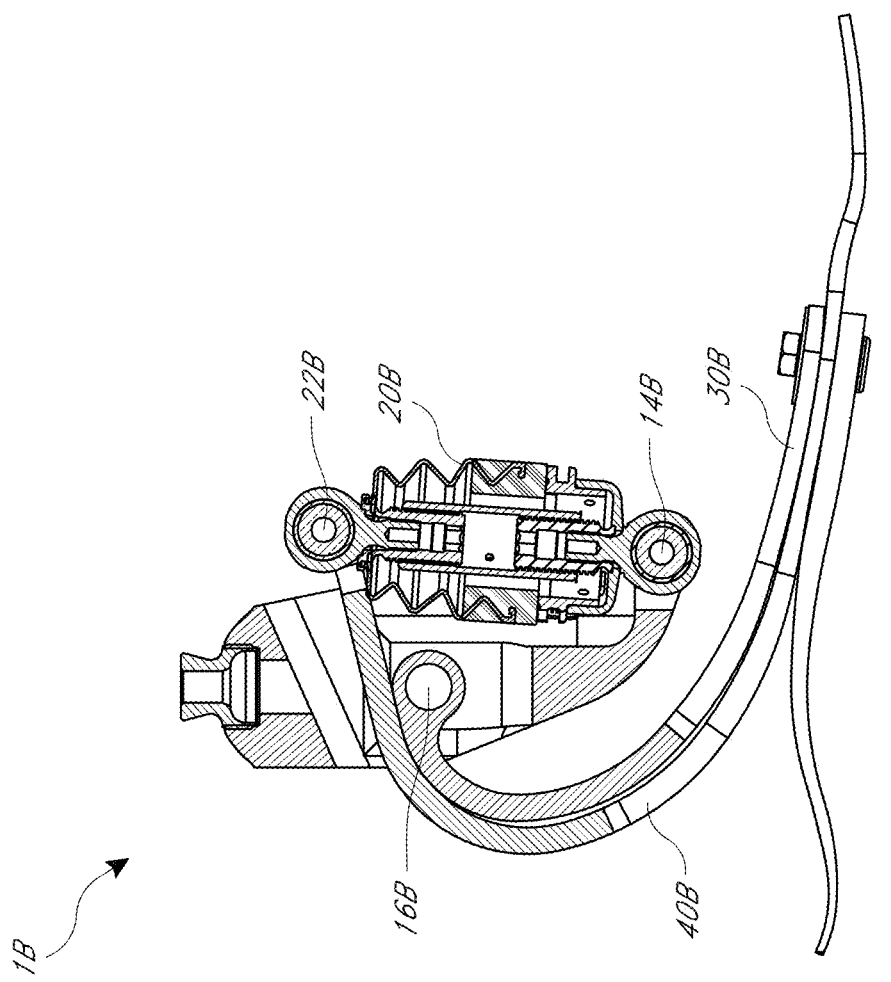
FIG. 22 is a cross-sectional side view of the prosthetic foot of FIG. 16.

Notably, the features in the embodiment in FIGS. 16-23 also form a triangle with at least one flexible portion and three rotatable connections, similar to that discussed above in the previous embodiments. For example, as best shown in FIG. 22, the prosthetic foot 1B includes a second connection portion 14B between the attachment member 10B and the actuator 20B. The actuator 20B can include a fourth connection portion 22B, connecting to the second flexible member 40B. The second flexible member 40A can come to abut the first flexible member 30B, as described above regarding the previous embodiments. The first flexible member 30B can attach to the attachment member 10B at the third connection portion 16B, completing the triangle.

Figure 23:
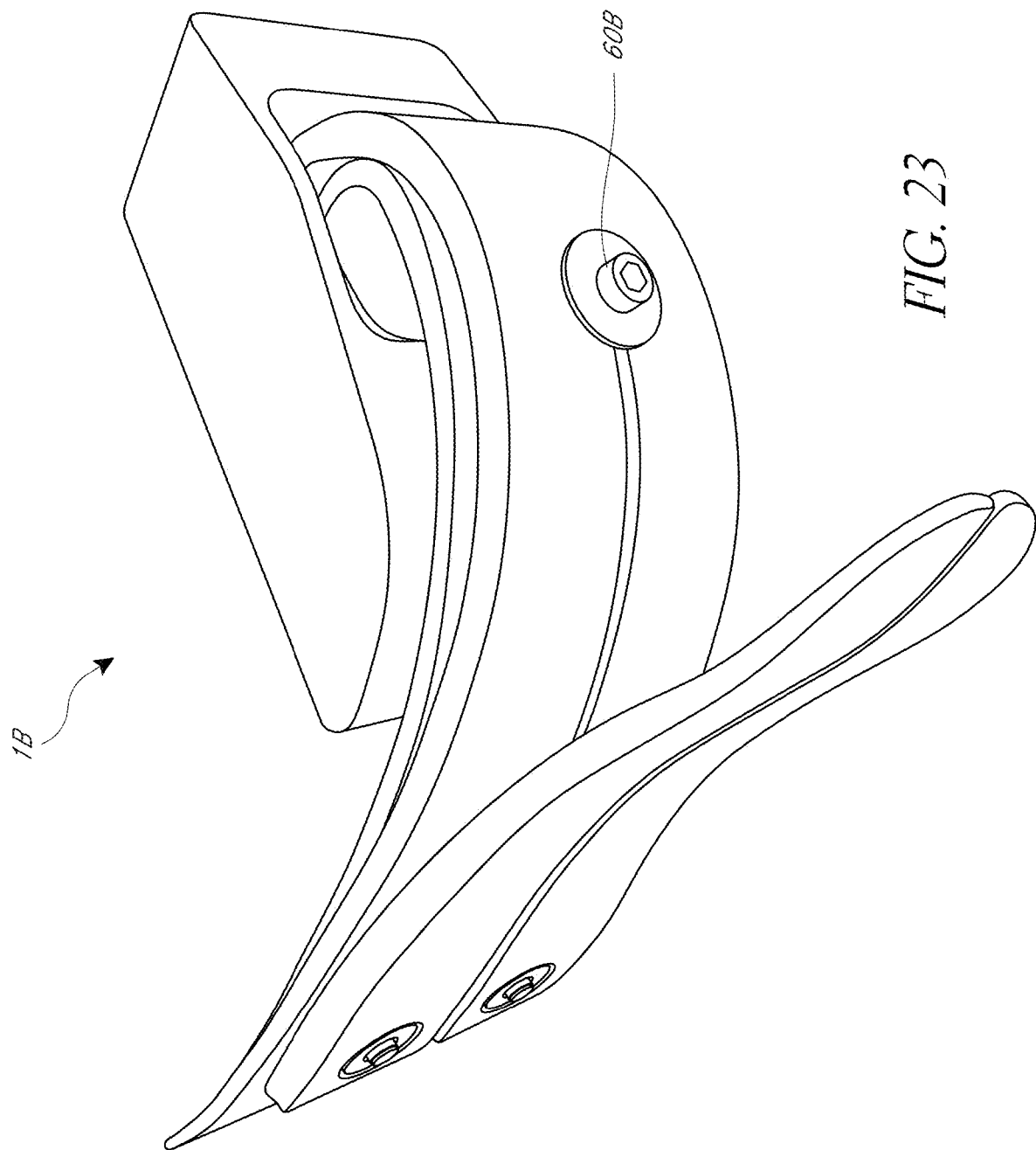
FIG. 23 is a view of the prosthetic foot of FIG. 16 with an additional fastener.

Further, as best shown in FIG. 23, the first and second flexible members 30B, 40B can be connected by a stiffness control member 60B. In the illustrated embodiment, the stiffness control member 60B is an adjustable fastening member 60B and can allow for varied resistance and flexibility in a manner similar to that in the embodiments discussed above. In the present embodiment, the adjustable fastening member 60B is provided between only the first and second flexible members 30B, 40B (and not the third flexible member 50B), and in a rear portion of the prosthetic foot 1B. Moving the adjustable fastening member 60B downward and forward results in a lever arm of the first and second flexible members 30B, 40B between the fastening member 60B and the attachment member 10B that is relatively longer, resulting in increased flexibility of the prosthetic foot 1B. Alternatively, moving the adjustable fastening member 60B upward results in a lever arm of the first and second flexible members 30B, 40B between the fastening member 60B and the attachment member 10B that is relatively shorter, resulting in increased stiffness of the prosthetic foot 1B.

Figure 24:
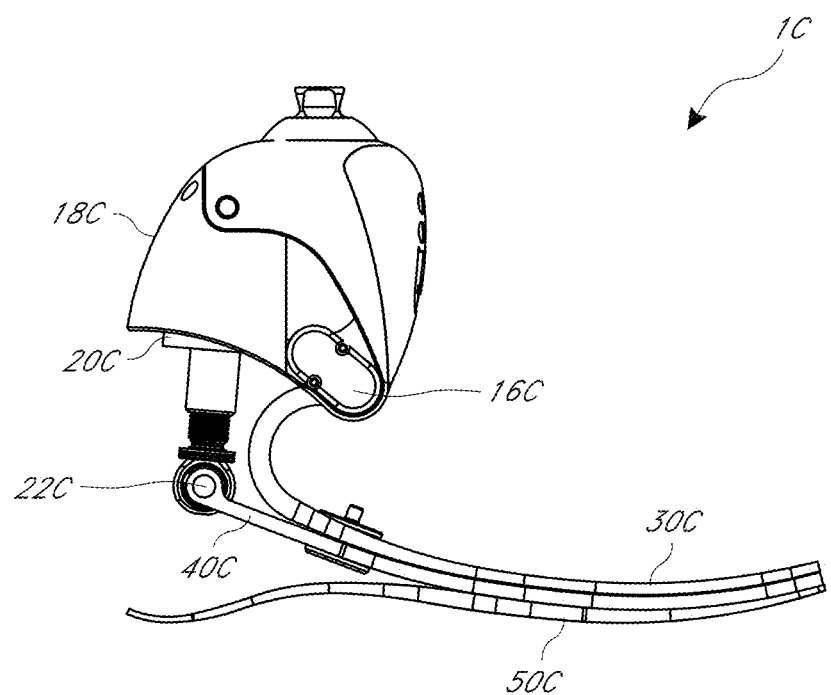
FIG. 24 is a side view of another embodiment of a prosthetic foot, similar to the prosthetic foot of FIG. 1.
Figure 25:
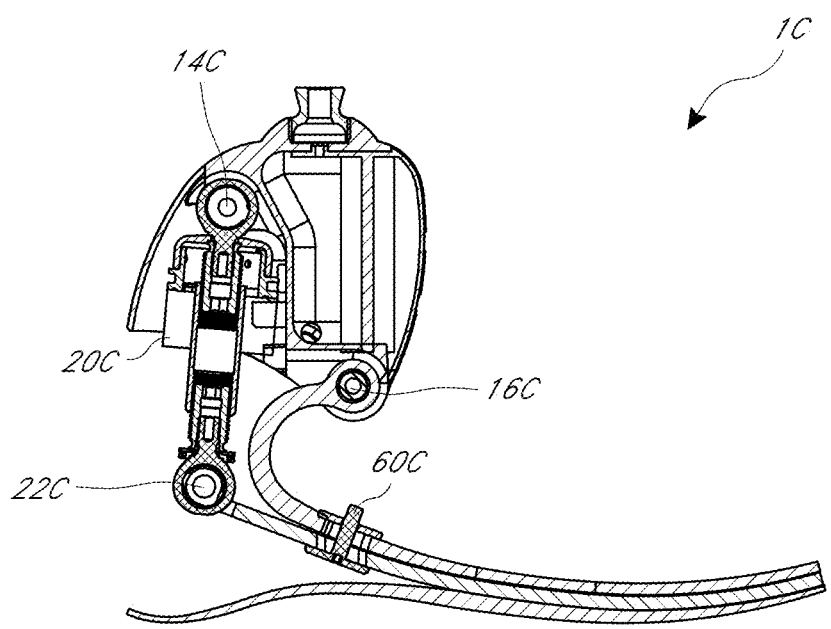
FIG. 25 is a cross-sectional side view of the prosthetic foot of FIG. 24.

FIGS. 24 and 25 depict yet another embodiment of a prosthetic foot 1C. This prosthetic foot 1C can be substantially similar to the prosthetic foot 1 depicted in FIGS. 1-8. Accordingly, similar components in the prosthetic foot 1C have the same numerical identifier as corresponding components in the prosthetic foot 1, except that the numerical identifier includes a "C". As shown, the first and second flexible members 30C, 40C can be coupled together by a fastening member 60C that does not hold the third flexible member 50C. Additionally, the cover 18C can extend further to the rear of the prosthetic foot 1C to protect a main operating portion of the actuator 20C, as best shown in FIG. 25. These additional or distinguishing features can optionally be included in the other embodiments described herein, and need not be used in combination with the additional features described.

Figure 26:
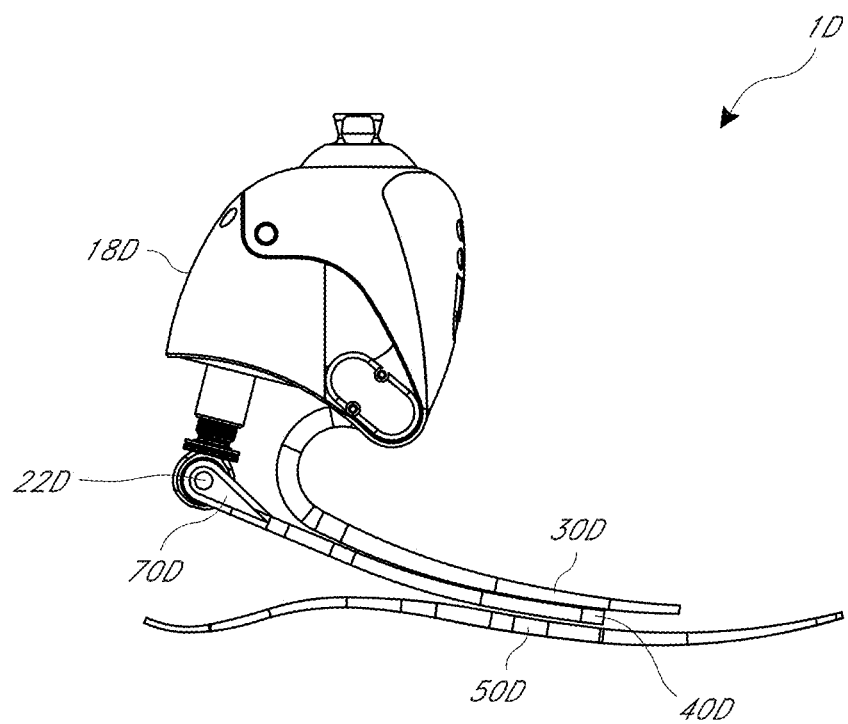
FIG. 26 is a side view of another embodiment of a prosthetic foot, similar to the prosthetic foot of FIG. 1.
Figure 27:
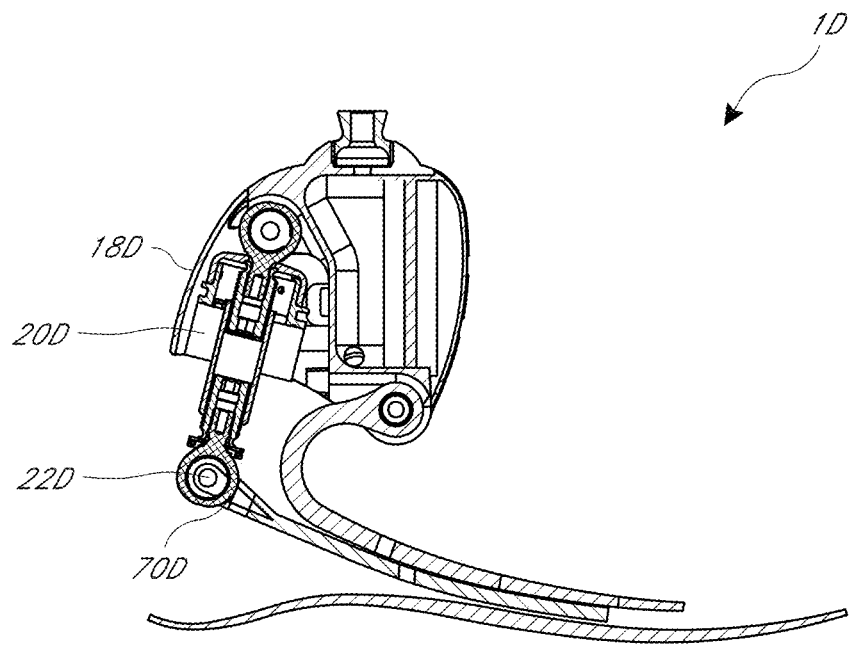
FIG. 27 is a cross-sectional side view of the prosthetic foot of FIG. 26.

FIGS. 26 and 27 depict yet another embodiment of a prosthetic foot 1D. This prosthetic foot 1D can be similar to the prosthetic feet 1, 1C depicted in FIGS. 1-8 and 24-25. Accordingly, similar components in the prosthetic foot 1D have the same numerical identifier as corresponding components in the prosthetic foot 1, 1C, except that the numerical identifier includes a "D". The prosthetic foot 1D can have a cover 18D similar to the cover 18C. The prosthetic foot 1D can also have first and second flexible members 30D, 40D shorter than the third flexible member 50D. Further, the second flexible member 40D can be shorter than the first flexible member 30D. The varying lengths of the flexible members 30D, 40D, 50D can alter the elastic resistance provided by the members as the foot bends over each portion of the members. For example, prosthetic foot 1D may provide less resistance to bending at the toe portion than bending at a middle portion of the foot. In some embodiments, the first and second flexible members 30D, 40D can end substantially at bolts such as the bolts 62B, described above in relation to prosthetic foot 1B. More generally, in some embodiments a reduced number of flexible members, such as only one or only two, can extend beyond bolts or other fasteners connecting these flexible members together.

Additionally, the second flexible member 40D can include a flexible member brace depicted as a wedge piece 70D. The wedge piece 70D can be disposed at a rear portion of the second flexible member 40D and form a part of the fourth connection portion 22D to the actuator 20D. In some embodiments, the wedge piece 70D can be of a material different from the remainder of the second flexible member 40D. For example, the wedge piece can be a more rigid and resilient material such as aluminum, titanium, steel, or other metals, while the flexible member can be a more flexible material such as carbon fiber, glass fiber, nylon, or the like. Thus, the wedge piece 70D can provide a strong connection with the actuator 20D while the rest of the flexible member 40D is flexible (e.g., can flex, bend). As shown, the wedge piece 70D includes a hole that can receive an axle connecting it to the actuator 20D to allow a rotatable connection. Additionally, as shown the wedge piece 70D can be substantially surrounded (e.g., completely circumscribed) by the other materials of the flexible member 40D, such that it is mounted within the flexible member. In some embodiments, the flexible member 40D can be molded, layered, or otherwise constructed around the wedge piece 70D. In another embodiment, the wedge piece 70D can be inserted into an opening formed in the flexible member 40D.

These additional or distinguishing features can optionally be included in the other embodiments described herein, and need not be used in combination with the additional features described.

Figure 28:
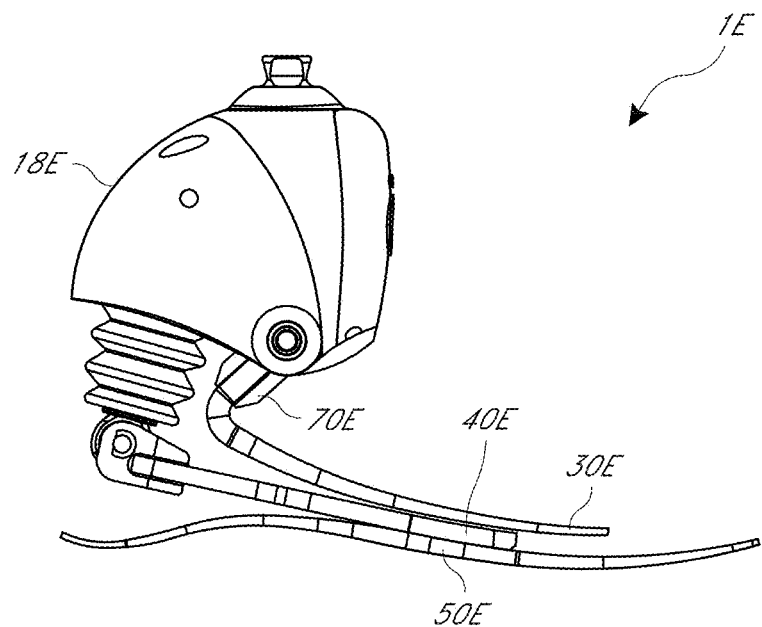
FIG. 28 is a side view of another embodiment of a prosthetic foot, similar to the prosthetic foot of FIG. 1.
Figure 29:
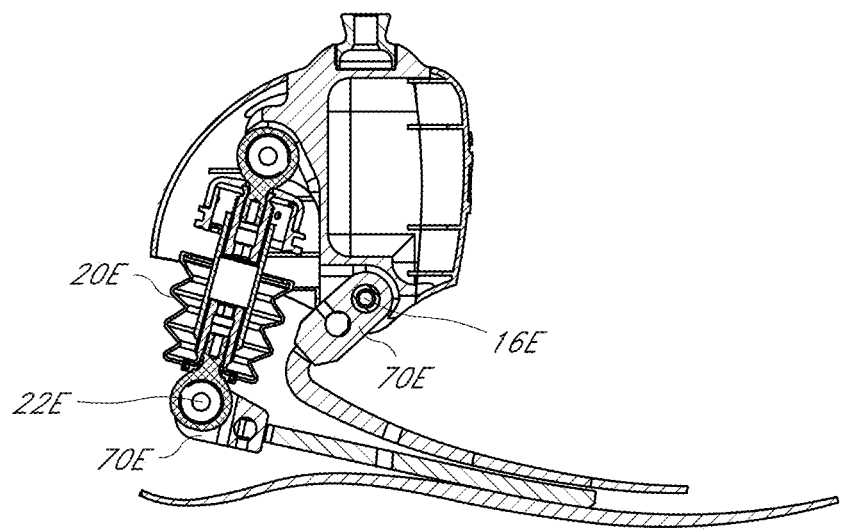
FIG. 29 is a cross-sectional side view of the prosthetic foot of FIG. 28.
Figure 30:
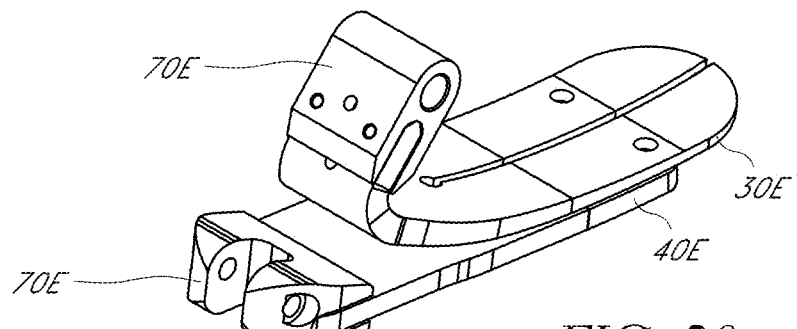
FIGS. 30 and 31 are perspective and exploded perspective views of flexible members and braces of the prosthetic foot of FIG. 29.

FIGS. 28 and 29 depict yet another embodiment of a prosthetic foot 1E, which is similar to the prosthetic foot 1C, 1D. Accordingly, similar components in the prosthetic foot 1E have the same numerical identifier as corresponding components in the prosthetic foot 1C, 1D, except that the numerical identifier includes an "E". The prosthetic foot 1E includes flexible members 30E, 40E, 50E with lengths similar to the flexible members of the prosthetic foot 1D. Notably, the first flexible member can have a sharper shape than the C-shapes described above. In particular, in this embodiment (and optionally in the other embodiments described herein) the shape can be substantially L-shaped, with a sharp corner. In other embodiments, the flexible member 30E can have a proximal portion that is angled (e.g. extends at an acute angle in the fore-aft direction, extends at an obtuse angle in the fore-aft direction) relative to a distal portion of the flexible member 30E. Additionally, the prosthetic foot 1E includes a flexible member brace 70E similar to the wedge piece 70D previously described. However, the flexible member brace 70E can mount around (e.g., over) a distal end of the more flexible portion of the flexible member 40E, as opposed to the flexible portion wrapping around the wedge piece 70D. A hole in the brace 70E can facilitate connection to the actuator 40E with an axle, as described in similar embodiments above.

Figure 31:
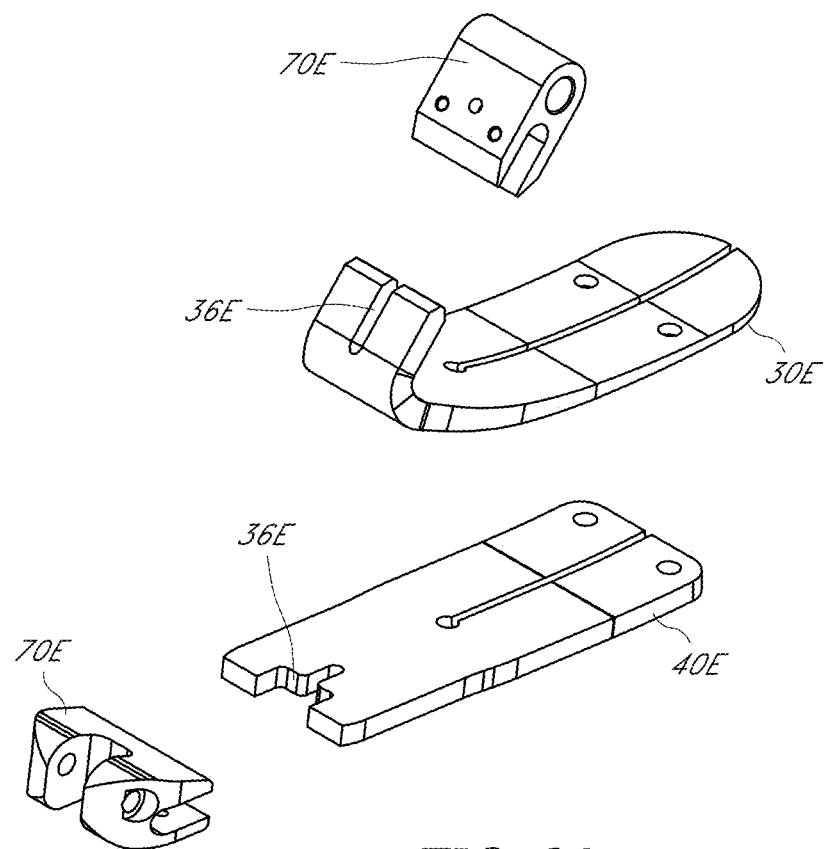
Figure 32:
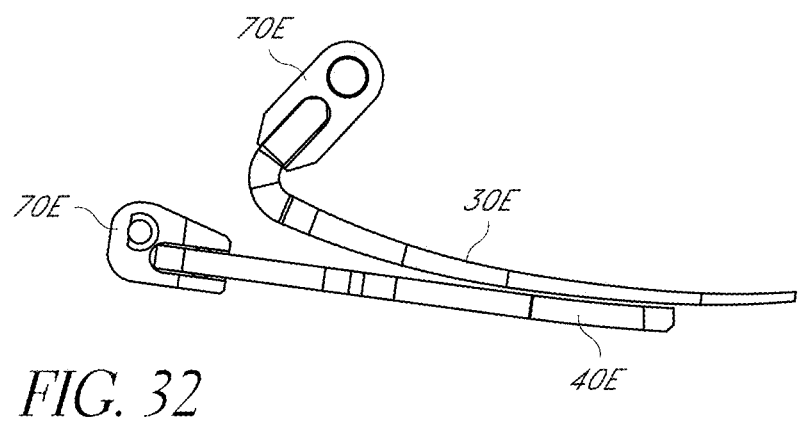
FIGS. 32 and 33 are side views of FIGS. 30 and 31.
Figure 33:
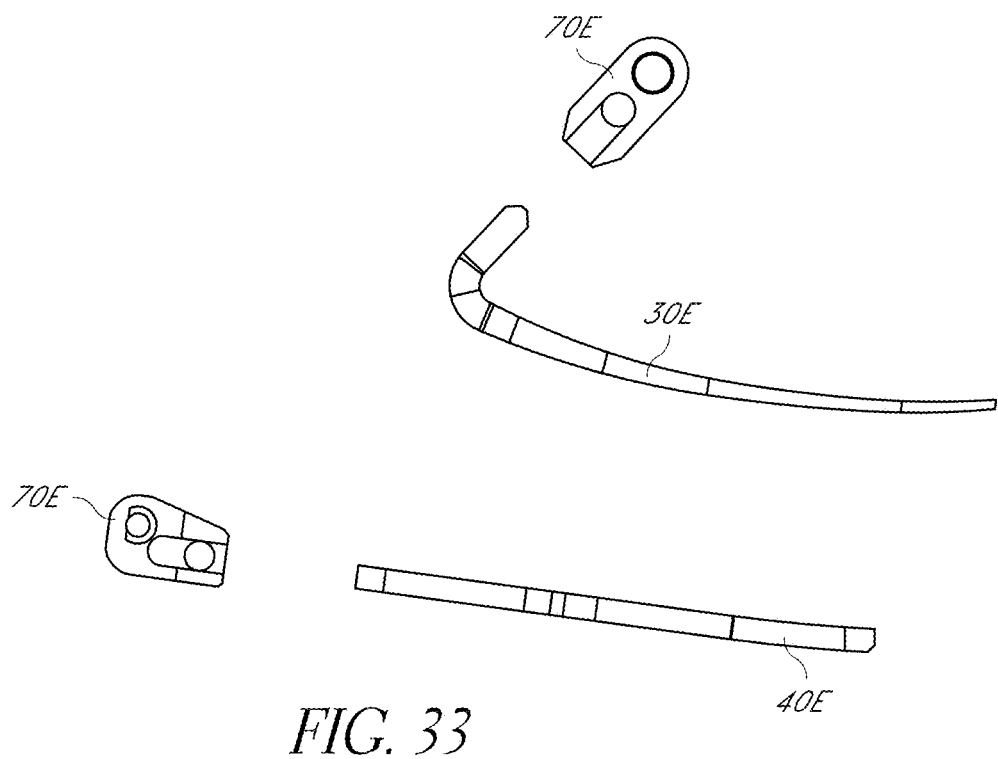
Figure 34:
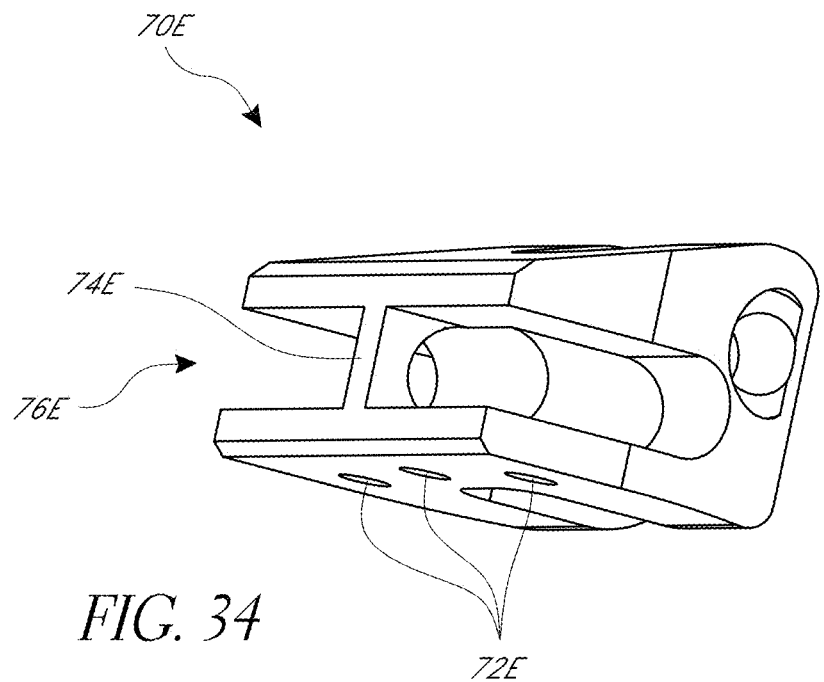
FIGS. 34 and 35 are perspective views of the braces of FIGS. 30-33.
Figure 35:
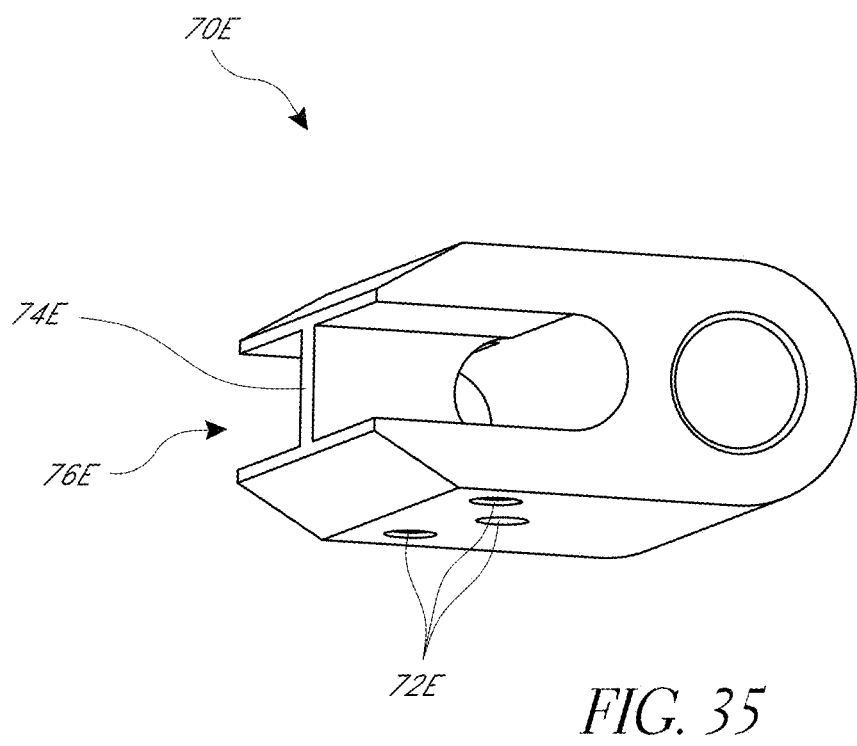

The flexible member brace 70E can have a C-shape with an opening that receives the flexible member 40E, as best shown in FIGS. 34 and 35. The flexible member brace 70E can be secured to the flexible member 40E after it has been made, by screws or other threaded fasteners that can be received in holes 72E. In other embodiments the flexible member brace 70E can be coupled to the flexible member 40E via other suitable mechanisms (e.g., an adhesive, press-fit connection). The receiving piece 70E can additionally include a solid divider 74E in a middle portion of the opening that receives the flexible member 40E, which can have a corresponding slot 76E. The divider 74E can provide the flexible member brace 70E with additional strength, preventing the piece from bending open when under load. As best shown in FIG. 31, the flexible members 30E, 40E can include corresponding slits 36E similar to the slits described above. The slits 36E can be shaped to match the divider 74E, and can optionally extend further, as discussed in other embodiments, herein. The slits 36E can form two arms that can receive the screws or other threaded fasteners, thus attaching the flexible member 40E to the brace 70E.

Notably, the first flexible member 30E can attach at the third connection portion 16E to the cover 18E with a similar flexible member brace 70E. The flexible member braces 70E can be substantially similar in their attachment to the flexible members 30E, 40E.

These additional or distinguishing features can optionally be included in the other embodiments described herein, and need not be used in combination with the additional features described.

Figure 36:
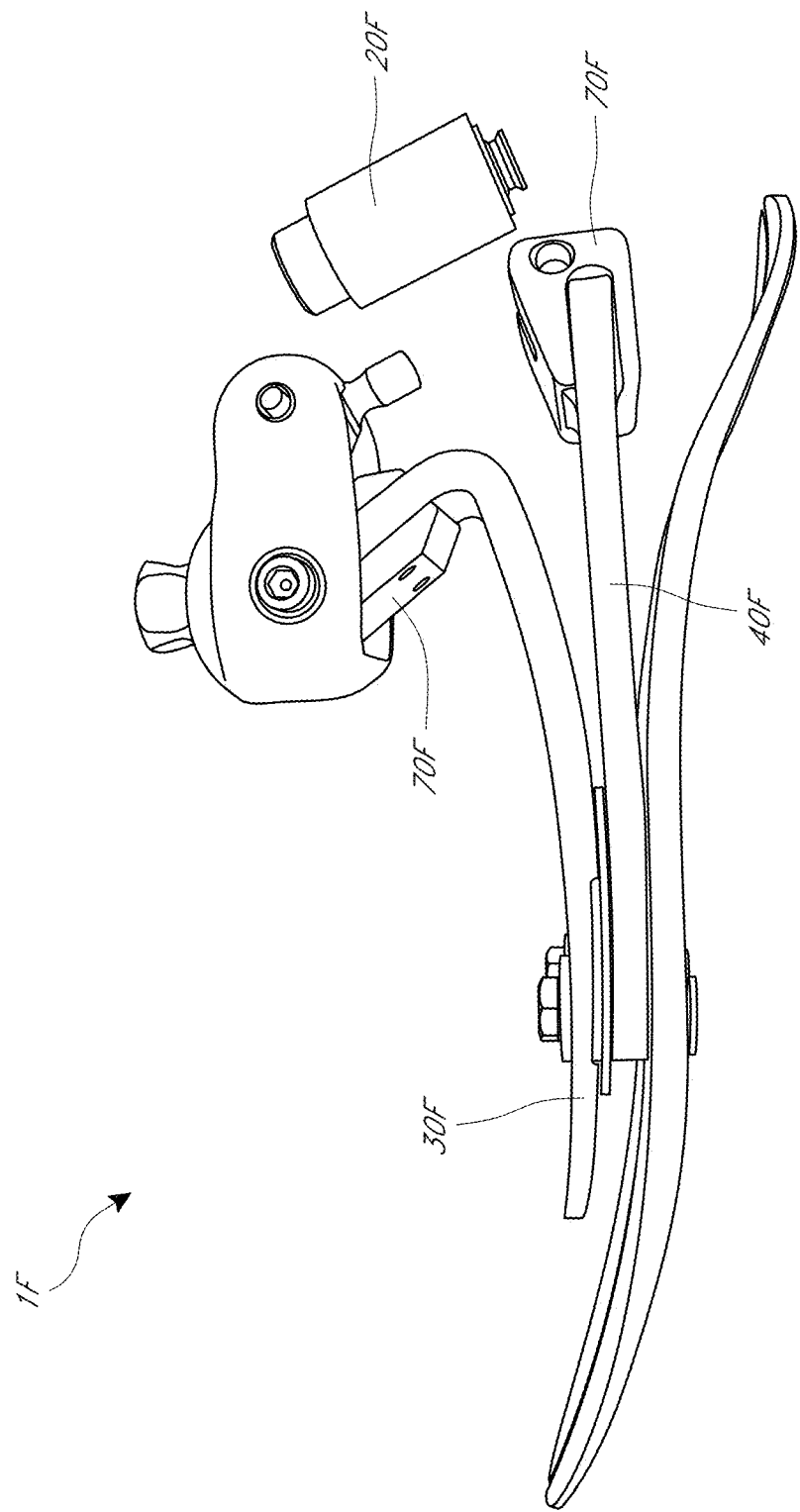
FIG. 36 is a side, exploded view of another embodiment of a prosthetic foot, similar to the prosthetic foot of FIG. 1.
Figure 37:
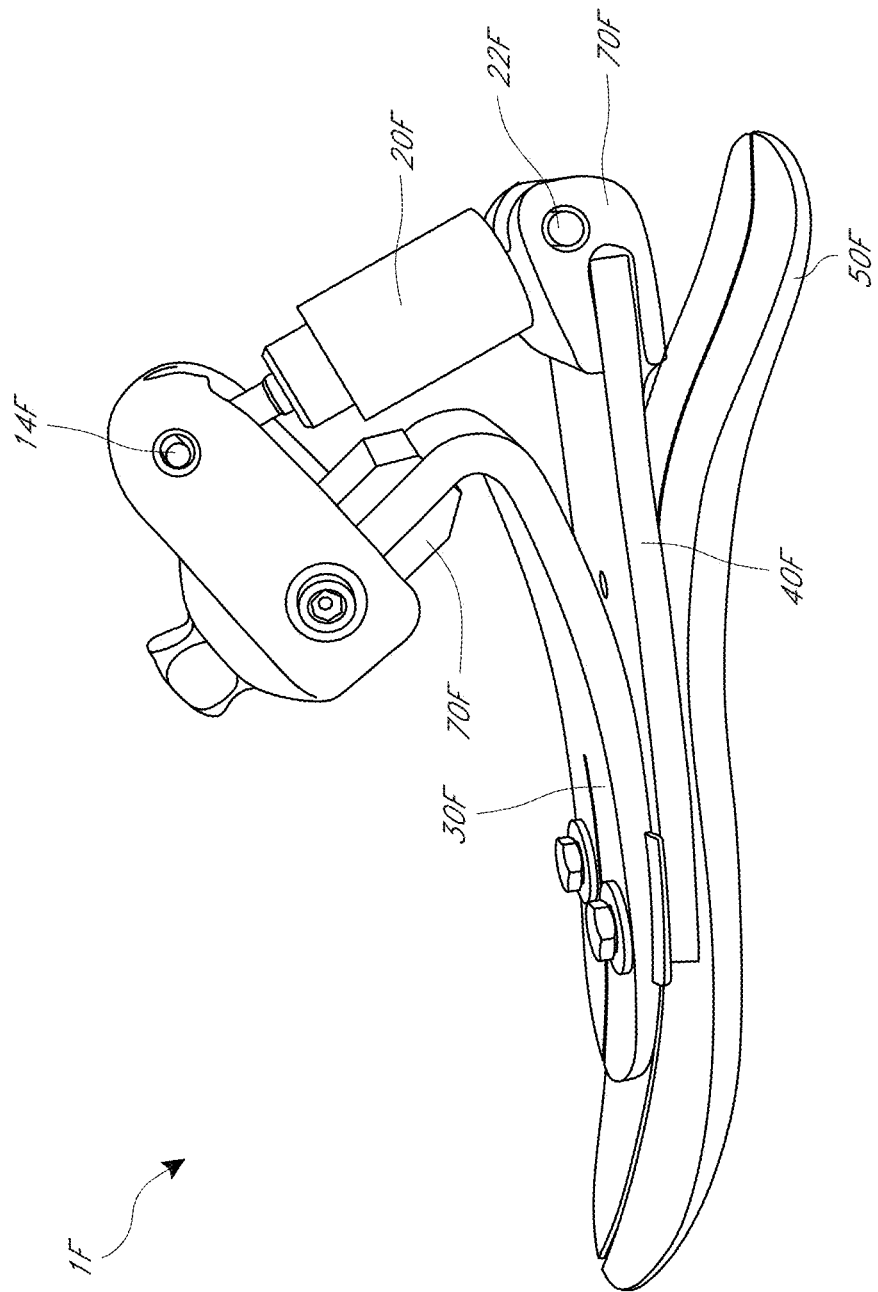
FIG. 37 is a side view of the prosthetic foot of FIG. 36 in assembled form.

FIGS. 36 and 37 depict yet another embodiment of a prosthetic foot 1F, substantially similar to the prosthetic foot 1E in FIGS. 28 and 29. Accordingly, similar components in the prosthetic foot 1F have the same numerical identifier as corresponding components in the prosthetic foot 1E, except that the numerical identifier includes an "F". The prosthetic foot 1F can have a lower profile and a smaller actuator. More particularly, in some embodiments the actuator can be replaced by a static heel-height adjustment element 20F. The heel-height adjustment element 20F can be in the form of an adjustable screw, as shown in the figures. The screw 20F can be rotated (e.g., manually rotated by a user) to adjust a distance between the second and fourth connection portions 14F, 22F, which can substantially set the heel height of the prosthetic foot 1F (e.g., by pivoting the adapter axis, such as the axis of a pyramid connector of the prosthetic foot, relative to the bottom flexible member 50F). Thus, the prosthetic foot 1F can optionally be a purely mechanical foot without any actuator. However, in further embodiments the heel-height adjustment element 20F can also include a dynamic actuator such as a hydraulic damping actuator, such that it can also provide a damping force during use. Further information can be found in U.S. application Ser. No. 13/622,991, filed Sep. 19, 2012, the entirety of which is hereby incorporated by reference and should be considered a part of this specification. Further, in some embodiments the heel-height adjustment element 20F can use other mechanical adjustment elements such as a friction lock, a set screw, a ratchet mechanism, a lock and pin, and the like to adjust the heel height of the prosthetic foot 1F to a desired heel height and to hold the element at said desired heel-height. These additional or distinguishing features can optionally be included in the other embodiments described herein, and need not be used in combination with the additional features described.

Figure 39:
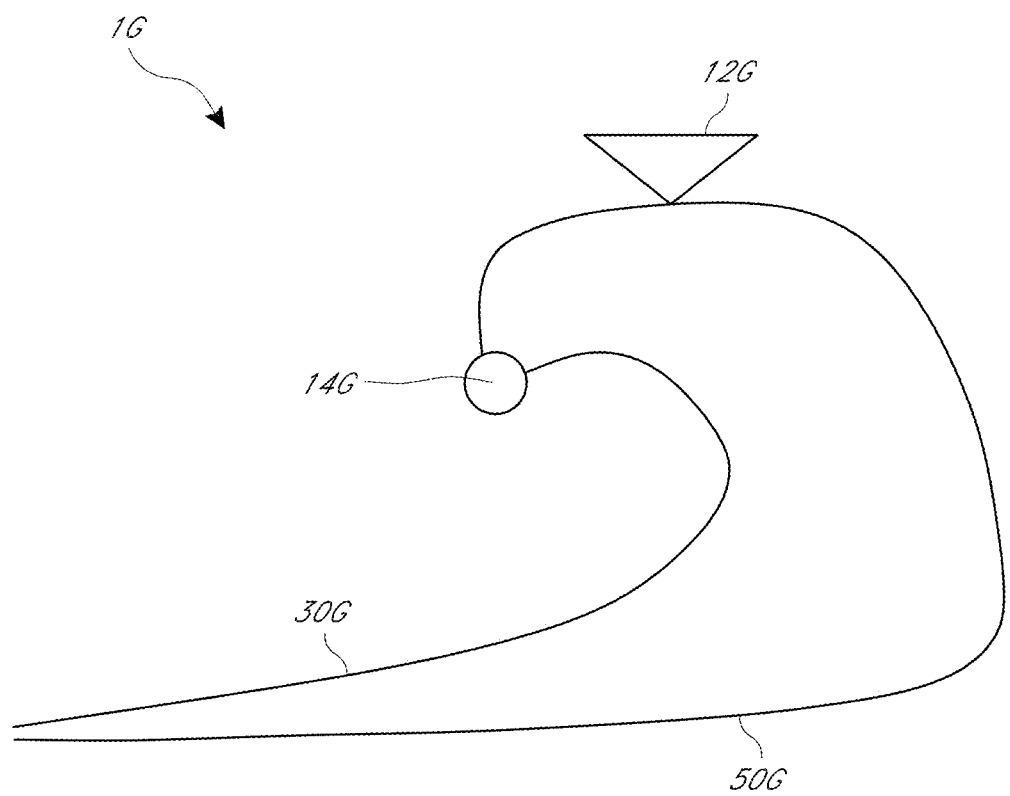
FIG. 39 is a side view of another embodiment of a prosthetic foot.

FIG. 39 depicts another embodiment of a prosthetic foot 1G. As shown in FIG. 39, a prosthetic foot comprising a first connection portion 12G that can be, for example, a pyramid connector. The first attachment portion 12G can connect to or be mounted on (e.g., clamped to, bolted to) a lower flexible member 50G that can be curved (e.g., have a C-shape). At an upper end of the lower flexible member 50G, it can rotatably connect at a second connection portion 14G to an upper flexible member 30G. The upper flexible member 30G can also be curved (e.g., have a C-shape), such that the upper flexible member 30G can be substantially within the lower flexible member 50G. The lower flexible member 50G can then contact the ground during use. The upper flexible member 30G can also press against the lower flexible member 50G during use, along a middle or toe portion of the prosthetic foot 1G to support forces applied through the first connection portion 12G. In the illustrated, the prosthetic foot 1G has a single pivot point between the lower flexible member 50G and the upper flexible element 30G provided by the second connection portion 14G.

Figure 40:
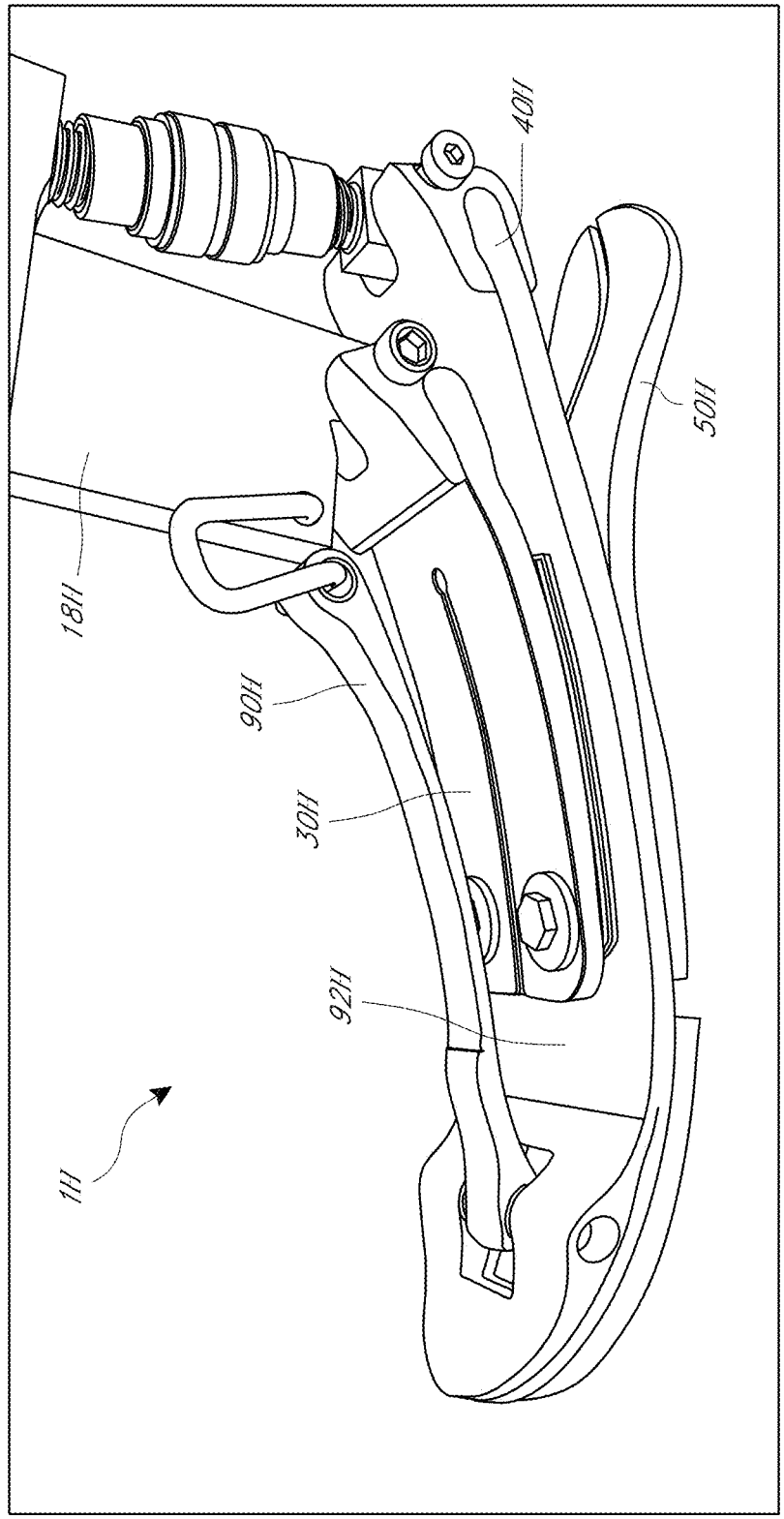
FIG. 40 is a side view of another embodiment of a prosthetic foot.

FIG. 40 depicts another embodiment of a prosthetic foot 1H. The prosthetic foot 1H can include a fourth flexible member 90H, but can otherwise be similar to the prosthetic foot 1F in FIGS. 36 and 37. The fourth flexible member 90H can connect to the cover 18H (or similarly to a first connection portion similar to the first connection portion 12) at one end and to another flexible member 30H, 40H, 50H at a toe region of the prosthetic foot 1H. As shown, the fourth flexible member 90H can connect to the second flexible member 40H in the toe region, and the other flexible members 30H, 50H can stop short of the toe region. Further, the second flexible member 40H can include a flexible region 92H that provides additional flexibility at a metatarsal region, just past the flexible members that do not extend to the toe region (first and third flexible members 30H, 50H here). Further, the flexible region 92H can be at a metatarsal region inward from the toe portion where the fourth flexible member 90H connects to the second flexible member 40H. As shown, the fourth flexible member 90H can connect at both ends by rotatable connections. Further, as shown, the fourth flexible member 90H can mount at a pivot axis that passes through the second flexible member 40H.

Advantageously, the prosthetic foot 1H can provide significant load bearing in the toe region when the foot is set to high heel heights. For example, the prosthetic foot 1H can provide significant load bearing in the toe region when used with a high-heel shoe. The second flexible member 40H can bend at the flexible region 92H such that the toe region is substantially flat when in a high-heel shoe. The fourth flexible member 90H can then transmit loads between the toe region and the rest of the prosthetic foot 1H, such as a first connection portion. Absent the fourth flexible member 90H, forces from the toe portion would be transmitted through the other flexible members 30H, 40H, 50H, which might be at extreme bending which could cause the material of the flexible members to fail.

Figure 41:
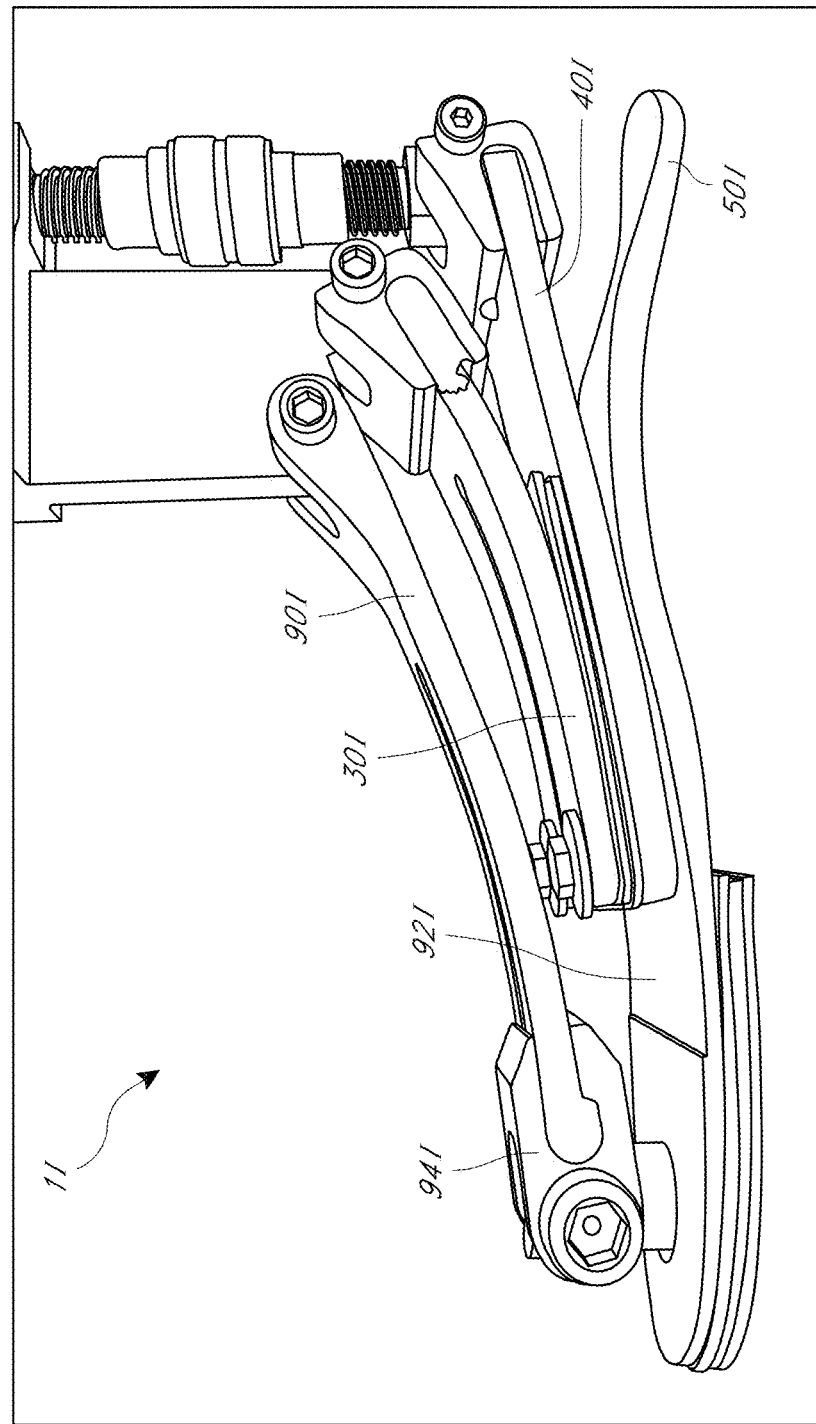
FIG. 41 is a side view of another embodiment of a prosthetic foot, similar to the prosthetic foot of FIG. 40.

FIG. 41 depicts another embodiment of a prosthetic foot 1I, similar to the prosthetic foot 1H. As shown, the fourth flexible member 90I connects to the third flexible member 50I instead of the second flexible member 40I. Further, the third flexible member 50I extends into the toe region like the second flexible member 40H in FIG. 40, and the second flexible member 40I in this embodiment does not extend to the metatarsal region, like the third flexible member 50H in FIG. 40. Further, the third flexible member 50I includes a flexible region 92I similar to the previously described flexible region. Finally, the connection between the third and fourth flexible members 50I, 90I can be raised from the third flexible member 50I and include a flexible member brace 94I similar to the flexible member brace 70E described in FIGS. 30-33.

FIGS. 42-45 show another embodiment of a prosthetic foot 1J. The prosthetic foot 1J has an attachment member or adapter 10J with a connector 12J. In the illustrated embodiment, the connector 12J is a male pyramid. However in other embodiments, the connector 12J can be of other suitable types (e.g., threaded hole, tube clamp, etc.). The connector 12J can attach to a stump of an amputated leg (e.g., via another prosthetic device, such as a pylon).

The prosthetic foot 1J can have a top plate assembly 30J, an intermediate plate 40J and a bottom plate 50J. The bottom plate 50J can extend from a heel end 50J1 to a toe end 50J2, which substantially correspond to heel and toe ends of the prosthetic foot 1J. In the illustrated embodiment, the bottom plate 50J can have a split 50J3 at least in the heel end 50J1. Though not shown, in some embodiments, the bottom plate 50J can have a split at least in a portion of the toe end 50J2.

With continued reference to FIGS. 42-45, the intermediate plate 40J can be disposed above the bottom plate 50J and can extend from a rear end 40J1 to a front end 40J2. The front end 40J2 and be located at a point on the prosthetic foot 1J proximal to the toe end 50J2 of the bottom plate 50J, such that the bottom plate 50J extends past the intermediate plate 40J. However, in other embodiments, the front end 40J2 of the intermediate plate 40J can be substantially aligned with the toe end 50J2 of the bottom plate 50J such that the intermediate and bottom plates 40J, 50J extend to generally the same position at a distal end of the prosthetic foot 1J. The rear end 40J1 of the intermediate plate 40J can have a connection portion (e.g., pivot portion) with an opening extending through the intermediate plate 40J (from the medial edge to the lateral edge) in the coronal plane, said opening sized to receive an axle therein. The rear end 40J1 can further have a slot or recess 40J1a into which at least a portion of a connector (e.g., bearing, such as a spherical bearing) 20J1 of a support member 20J (e.g., a mechanical actuator) can extend so that said axle can extend through the opening in the intermediate plate 40J and through the connector to interconnect the intermediate plate 40J with the support member 20J. A proximal portion 20J2 of the support member 20J can couple to a rear or proximal portion of the adapter 10J.

In one embodiment, the support member 20J can be pin connector of a set length that interconnects the intermediate plate 40J and the adapter 10J, where a proximal portion 20J2 of the support member 20J connects to the adapter 10J via a pivot connection 14J. In another embodiment, the support member 20J can be a mechanical actuator (e.g., a set screw) that can be mechanically actuated (e.g., with a key, via a lever, via a ratchet, etc.) to change the length of the support member 20J. In still another embodiment, the support member 20J can be a powered actuator and can have an electric motor that can be automatically actuated (or remotely actuated) to change the length of the support member 20J.

With continued reference to FIGS. 42-45, the top plate assembly 30J can include a first plate 30J1 and a second plate 30J2, where the second plate 30J2 is disposed above the intermediate plate 40J and the first plate 30J1 is disposed above the second plate 30J2. Optionally, the first plate 30J1 and the second plate 30J2 can be one elongated plate folded upon itself and around the pivot point 16J. The top plate assembly 30J can have a proximal end 32J and a distal end 34J. In the illustrated embodiment, the distal end 34J is generally aligned with the toe end 50J2 of the bottom plate 50J. However, in other embodiments, the distal end 34J can extend to a point proximal of or distal of the toe end 50J2 of the bottom plate 50J. The proximal end 32J of the top plate assembly 30J can couple to a distal portion 10J1 of the adapter 10J, as discussed further below. From the proximal end 32J, the top plate assembly 30J can curve rearward and downward in a generally C-shaped manner, and then extend forward to the distal end 34J along a generally planar section.

In the illustrated embodiment, the top plate assembly 30J has a split 36J that extends from the proximal end 32J to the distal end 34J (e.g., extends from the connection with the distal portion of the adapter 10J, through the C-shaped curved section and the generally planar section) of the top plate assembly 30J. As noted the top plate assembly 30J includes first and second plates 30J1, 30J2, and the split 36J extends through both plates 30J1, 30J2 from the proximal end 32J to the distal end 34J so that the first plate 30J1 is divided into medial and lateral members 30J1a, 30J1b and so that the second plate 30J2 is divided into medial and lateral members 30J2a, 30J2b. The top plate assembly 30J can couple to the intermediate plate 40J and/or bottom plate 50J via one or more fasteners 62 (e.g., bolts).

Figure 45:
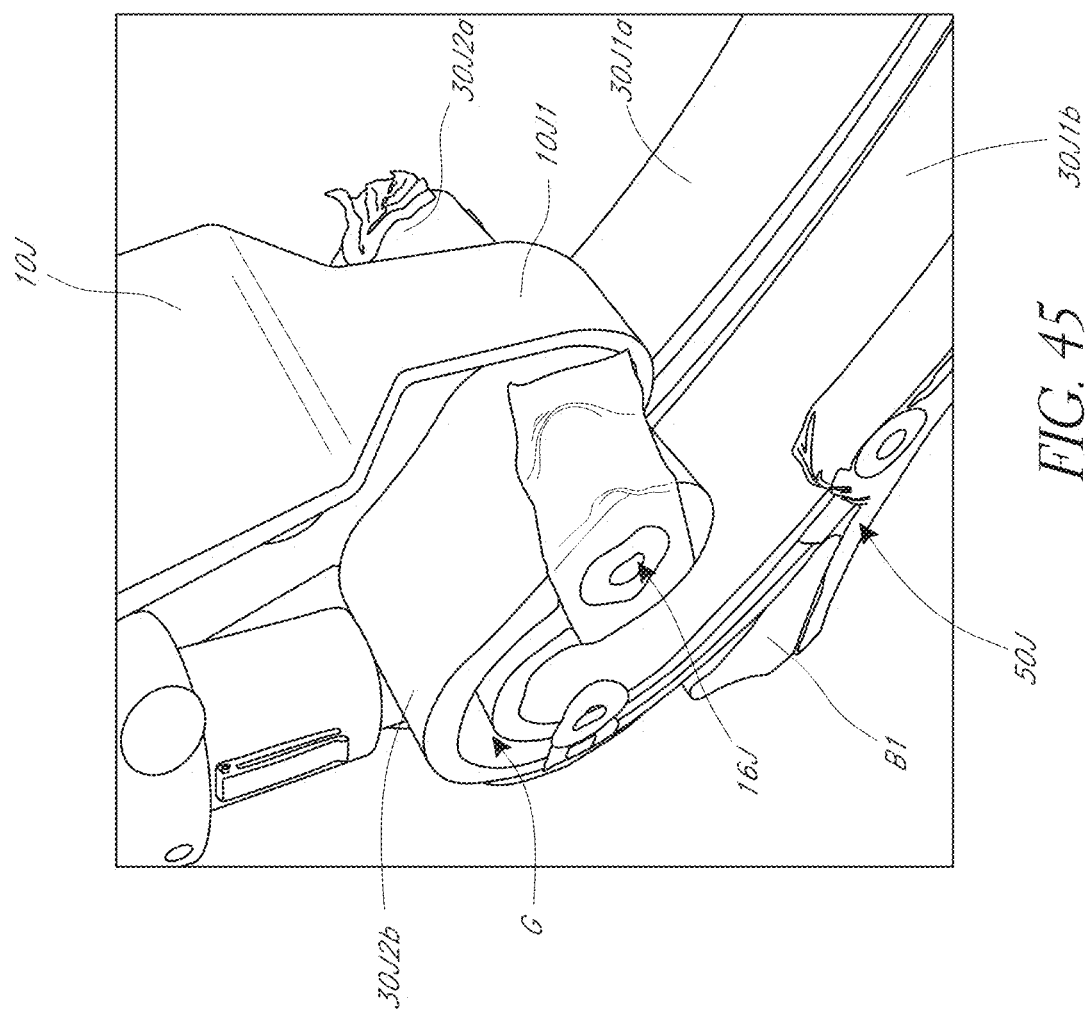
FIG. 45 is a partial perspective front view of the prosthetic foot of FIG. 42.

As best shown in FIG. 45, the distal end 10J1 of the adapter 10J can extend between the medial and lateral portions of the top plate assembly 30J (e.g., extend within the split 36J at the proximal end 32J of the top plate assembly 30J). The proximal end 32J can have an opening therein (along the coronal plane and perpendicular to the sagittal plane) sized to receive an axle that can extend from the medial to the lateral side of the top plate assembly 30J. Though not shown, the distal end 10J1 of the adapter 10J can have an opening through which said axle passes, such that the axle can interconnect the top plate assembly 30J (e.g., the first and second plates 30J1, 30J2) with the distal end 10J1 of the adapter 10J (e.g., via a bearing, such as a spherical bearing, in the distal end 10J1). Such a connection between the top plate assembly 30J and the distal end 10J1 of the adapter 10J advantageously facilitates medial and lateral movement of the prosthetic foot 1J, for example, by allowing twist or medial-lateral movement at the proximal end 32J of the top plate assembly 30J. Advantageously, the prosthetic foot 1J allows improved stability during stance (e.g., while the bottom plate 50J is in contact with the ground) by allowing medial-lateral or twist motion generally at a location of the prosthetic foot 1J (e.g., the proximal end 32J of the top plate assembly 30J) that generally corresponds with a location of a natural human ankle.

Figure 42:
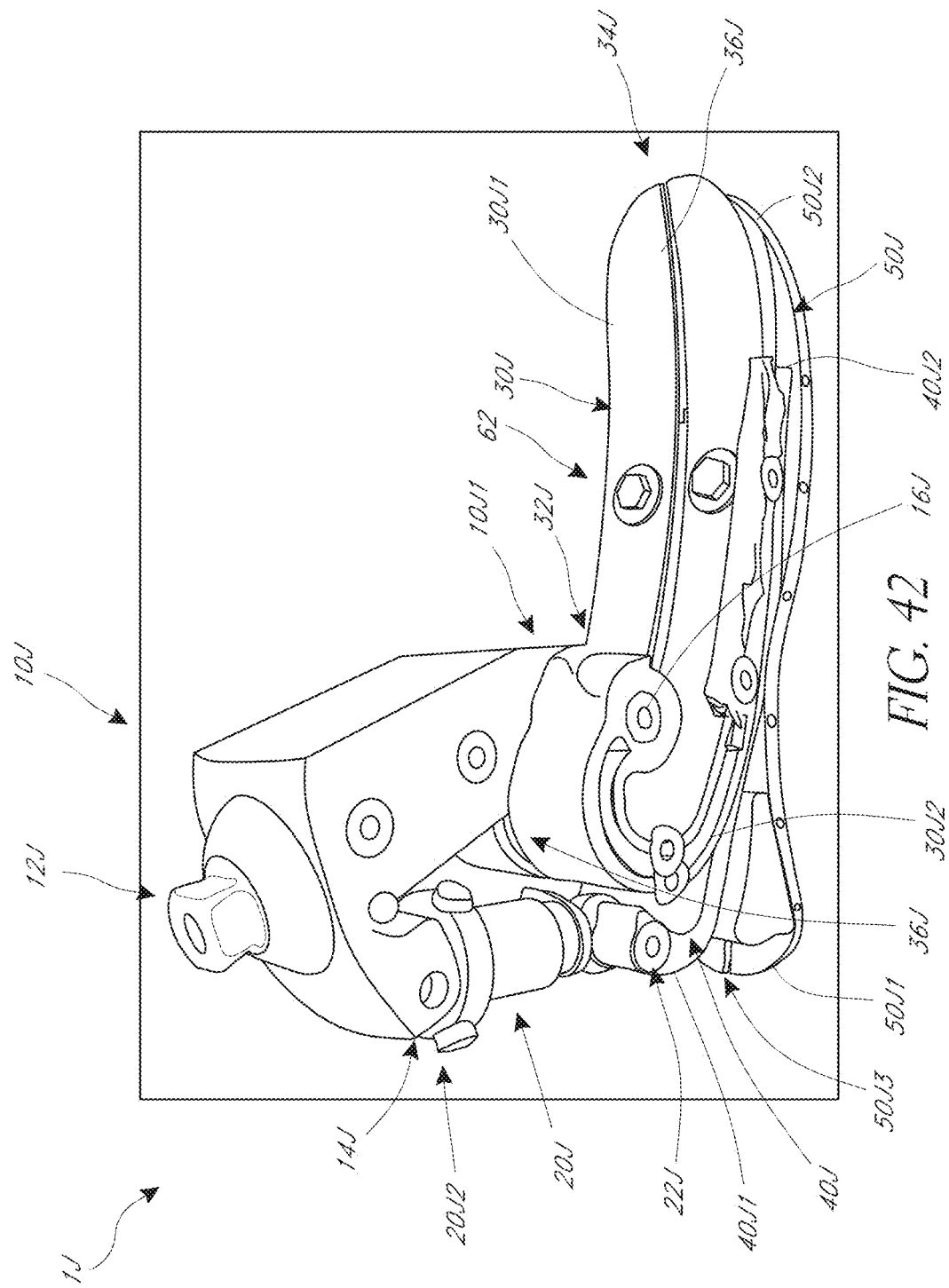
FIG. 42 is a perspective top view of another embodiment of a prosthetic foot
Figure 43:
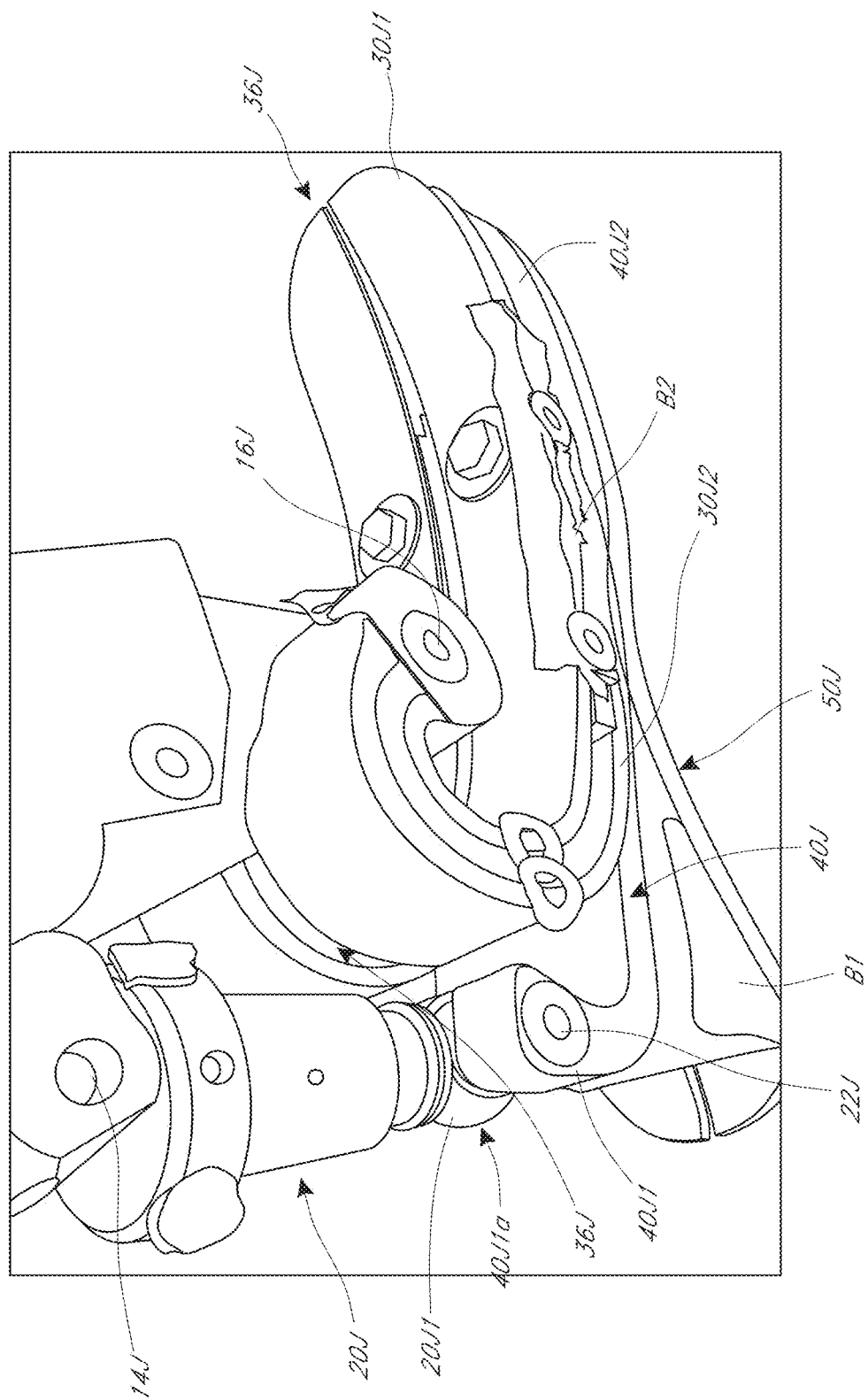
FIG. 43 is a partial perspective rear view of the prosthetic foot of FIG. 42.
Figure 44:
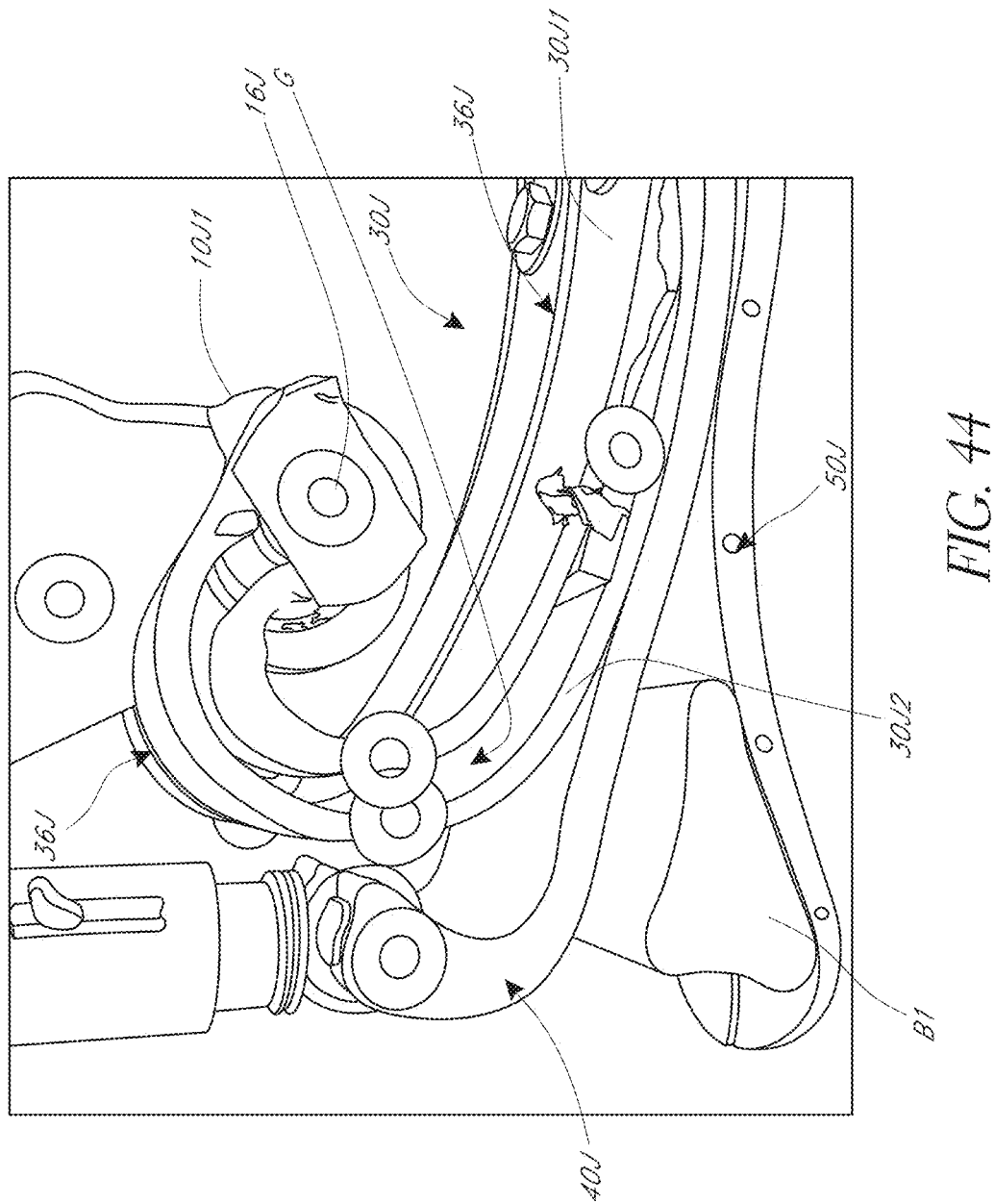
FIG. 44 is a partial side view of the prosthetic foot of FIG. 42.

In the illustrated embodiment, the top plate assembly 30J has two plates (the first and second plates 30J1, 30J2) that extend from the proximal end 32J to the distal end 34J. The first and second plates 30J1, 30J2 can be spaced from each other at least a long a portion of the length of the top plate assembly 30J to define a gap G between them, as shown in FIG. 45. The gap G can widen at the proximal end 32J to advantageously receive and hold the axle (e.g., an axle pin) therein. In some embodiments, one or more bumpers B2 are disposed between the first and second plates 30J1, 30J2 to facilitate the spacing of the plates 30J1, 30J2 apart from each other. As shown in FIG. 42, a bumper B1 (e.g., a triangular shaped bumper) can be disposed between the bottom plate 50J and the intermediate plate 40J near the heel end 50J1 of the bottom plate 50J. Stiffness of the prosthetic foot 1J, such as stiffness of the top plate assembly 30J can be adjusted using a stiffness control member, such as the stiffness control member 60 described above in connection with FIG. 8, or stiffness control member 60B described above in connection with FIG. 23.

Though the top plate assembly 30J in the illustrated embodiment has first and second plates 30J1, 30J2, in other embodiments the top plate assembly 30J can have only the first plate 30J1. In such an embodiment, the proximal end 32J of the first plate 30J1 can define the opening that receives the axle pin, or a connector (e.g., brace) can be connected to the proximal end 32J of the medial and lateral members of the first plate 30J1 to allow the coupling of the proximal end 32J to the distal end 10J1 of the adapter 10J.

Figure 46:
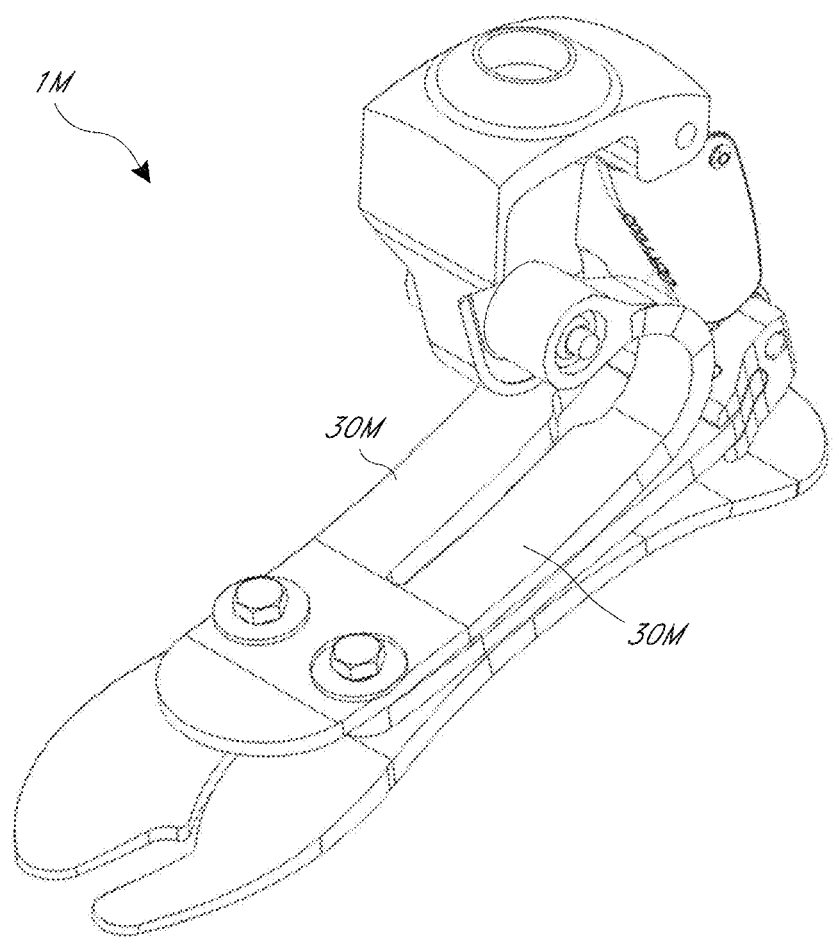
FIG. 46 is a perspective view of another embodiment of a prosthetic foot.
Figure 47:
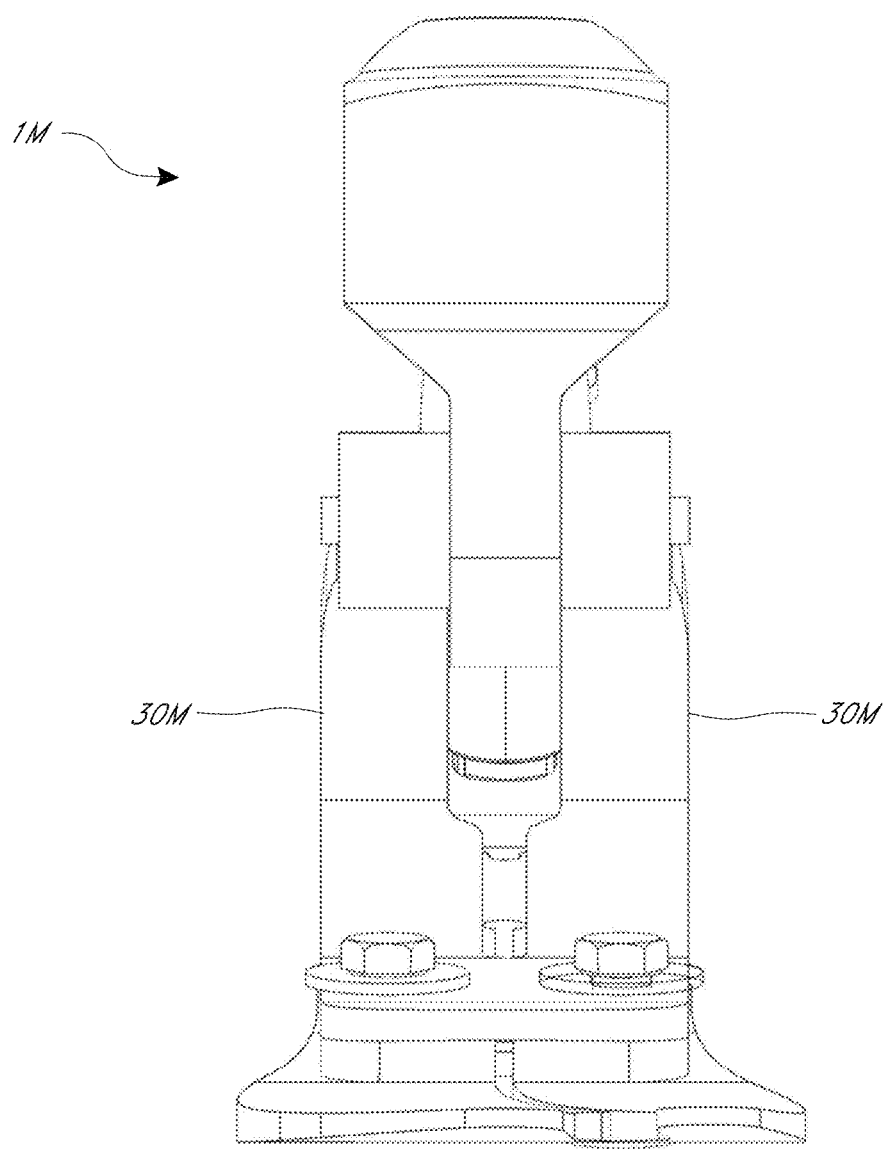
FIG. 47 is a front view of the prosthetic foot of FIG. 46.

FIGS. 46 and 47 depict a prosthetic foot 1M similar to the prosthetic foot 1J in FIGS. 41-45, and incorporate all the features of the prosthetic foot 1J described above, except that the first plate 30J1 and the second plate 30J2 combined into a single plate 30M, removing the gap G.

Figure 48:
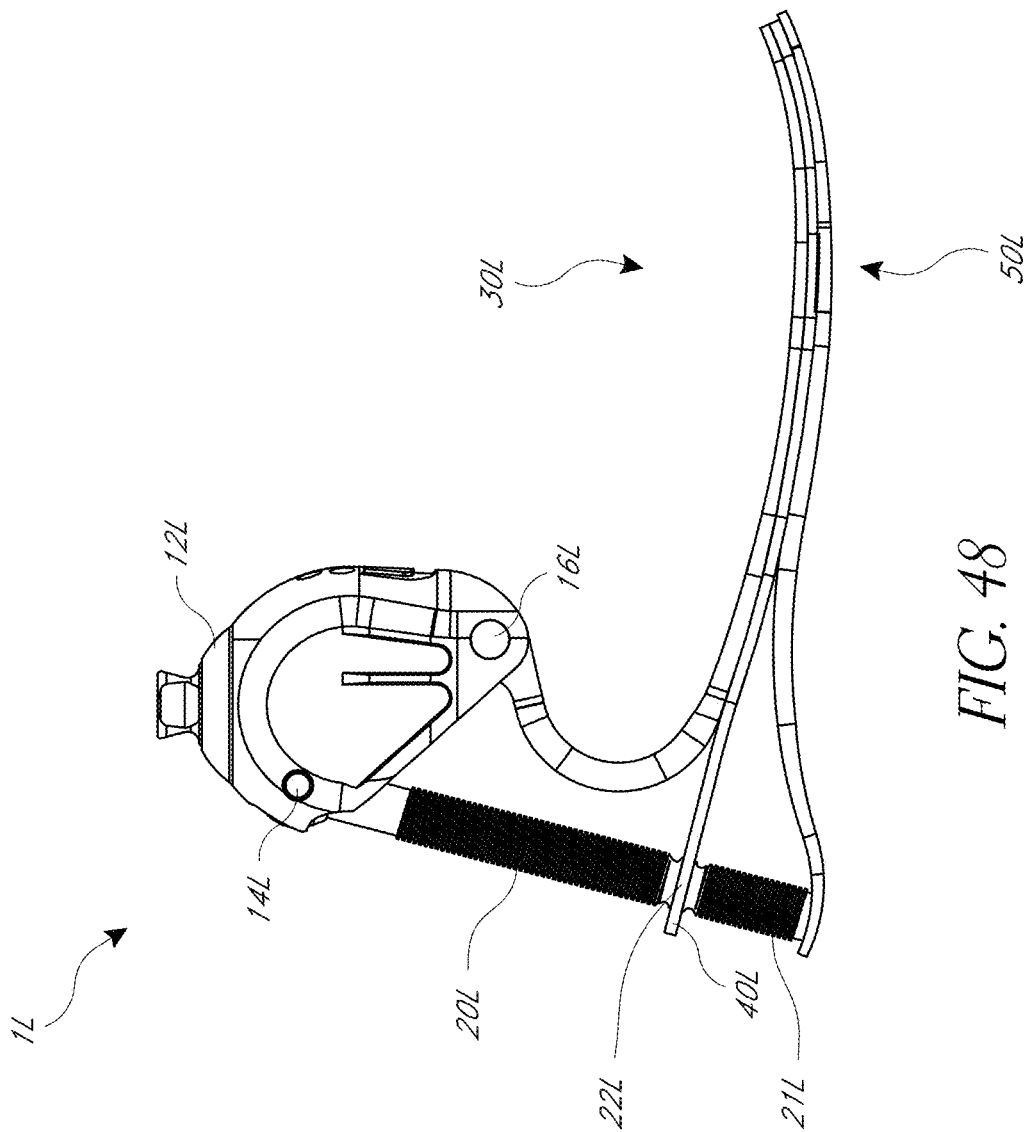
FIG. 48 is side view of another embodiment of a prosthetic foot.

FIG. 48 depicts another embodiment of a prosthetic foot 1L, similar to the prosthetic foot 1 depicted in FIGS. 1-8. Notably, in the depicted embodiment the actuator 20 can be removed and replaced with a first elastic connection 20L depicted as a coil spring. Thus, the second flexible member 40L can attach to the connection member 12L by the coil spring, providing energy storage and shock absorption in place of the actuator. In further embodiments, such a spring 20L can also be provided in a similar position, in series with the actuators described herein.

As further depicted in FIG. 48, the heel portions of the second and third flexible members 40, 50 can be connected by a second elastic connection 21L, also depicted as a coil spring. This can provide a structure that can more directly receive and absorb heel strike impacts, as the two elastic connections 20L, 21L can be arranged substantially along a direction of impact with the ground at the heel. In the illustrated embodiment, the first and second elastic connections 20L, 21L are aligned so as to be co-linear.

The elastic connections 20L, 21L can provide a degree of rotational freedom, such that the connection portions 14, 22 in the prosthetic foot 1 depicted in FIGS. 1-8 can be made non-rotatable connections. This can reduce the number of components included in the prosthetic foot 1L.

Figure 49:
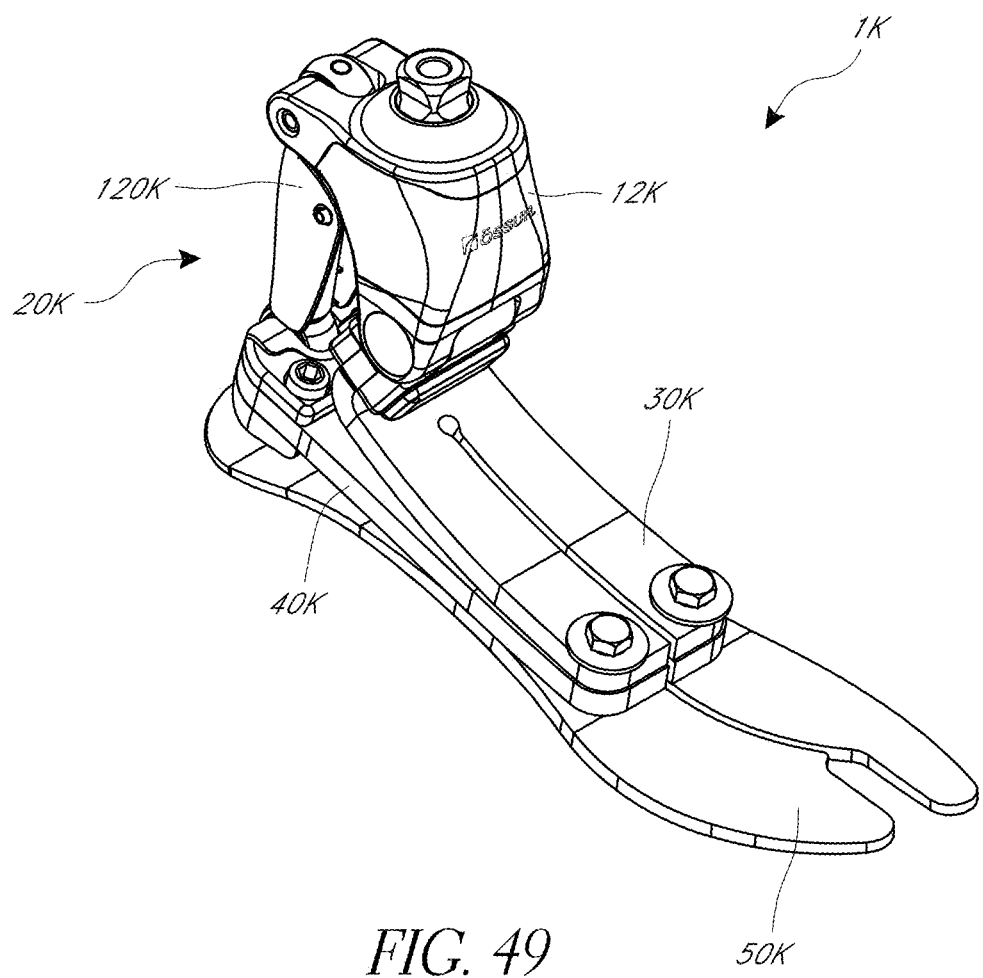
FIG. 49 is a perspective view of another embodiment of a prosthetic foot.
Figure 50:
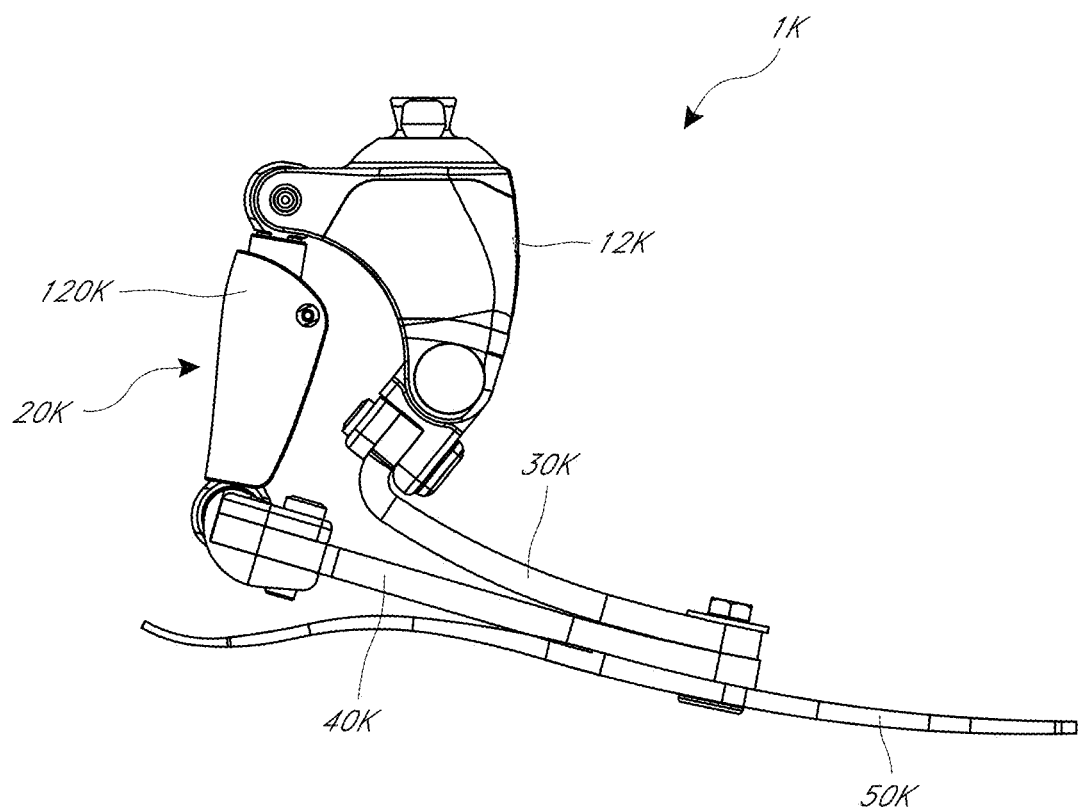
FIG. 50 is a side view of the prosthetic foot of claim 49.

FIGS. 49 and 50 depict another embodiment of a prosthetic foot 1K, similar to the prosthetic foot 1 depicted in FIGS. 1-8, and other prosthetic feet depicted herein. The prosthetic foot 1K can include a modified actuator 20K that can be protected by a housing 120K. The actuator 20K can be a powered actuator, damper, elastic member (such as a spring), or can be a rigid member such as a static bar or an adjustable screw member (such as the heel height adjustment element 20F depicted in FIGS. 36 and 37). Further, the flexible members 20K, 30K, 40K can be attached to the cover 18K and the actuator 20K using braces similar to the braces 70E depicted in FIGS. 28-35, such that the flexible members can be attached with screws, bolts, or other fasteners. Further, each of the flexible members can be attached by fasteners at a mid-foot section, such as depicted in FIG. 8.

In the illustrated embodiment, the third flexible member 50K can extend along an entire length of the prosthetic foot 1K (e.g., extend from heel-to-toe). The third flexible member 50K can additionally include a slit 36K similar to the slit 36 depicted in FIG. 5. The slit 36K can be curved inward, and expand a toe region to define a "big toe" or hallux portion. Further, the third flexible member 50K can generally curve inward and generally widen as it extends toward the toe portion such that the forefoot region is wider than the heel region. Further description is provided in U.S. Provisional Patent No. 62/019,233, filed 30 Jun. 2014, and incorporated by reference herein in its entirety. The second flexible member 40K can be disposed above the third flexible member 50K and extend from a proximal end operably coupled to the actuator 20K to a distal end at a location that is proximal of the toe end of the third flexible member 50K. The first flexible member 30K can have a generally L-shape, similar to that of the first flexible member 30E in FIG. 28, and can extend from a proximal end coupled to a bottom end of the connection member 12K to a distal end aligned with the distal end of the flexible member 40K.

Further variations to the design of the prosthetic feet are also possible. For example, the flexible members described above can be custom made for individual users. The thickness of each flexible member can then vary across the length of each flexible member to provide a desired amount of flexibility and resistance against bending at each portion of the members. The thickness of the flexible members can be determined by any combination of factors such as a user's weight, leg length, walking style, desired activities, residual limb strength, point of amputation, and the like.

Similarly, in some embodiments the flexibility of the flexible members can be varied by altering features in the flexible members such as the slits (described above). For example, in the depicted embodiments the slits extend over only a portion of any flexible element. However, in some embodiments the slit can extend across an entire flexible element, splitting it into two lateral pieces. The two lateral pieces can then be held together, for example, through their attachment to the other flexible elements. Additionally or alternatively, the slits in some embodiments can be asymmetric near a toe region of the flexible members. For example, the slit could curve inward (e.g., toward the medial side) near the toe region to promote a more natural roll-over during ambulation. The extent and direction of the slit can alter the flexibility in medial-lateral directions, thus potentially improving the medial-lateral stability of the prosthesis. Even further, in some embodiments there may be a distinct big-toe cutout in the flexible members to provide this and also allow fitting with a sandal.

As another variation, in some embodiments both of the first and second flexible members can be substantially straight (e.g., planar, flat) along their lengths. For example, the prosthetic foot 1E in FIG. 28 can be modified such that the first flexible member 30E is straight and the associated flexible member brace 70E can be rotated to hold the flexible member at the appropriate location and angle. The flat flexible members can facilitate a low-profile or symes prosthetic foot. Additionally, in an embodiment low-profile prosthetic foot the actuator can be substituted with a heel-height adjustment element to further facilitate the low-profile design.

Advantageously, the prosthetic foot embodiments disclosed can provide for a natural rocking motion during a stance phase of gait that can provide improved stability to the prosthetic foot (e.g., the attachment member can move relative to one or more of the flexible members during stance). This improved stability can also be provided in embodiments that include an actuator, e.g., when the actuator is locked in a particular position or is substantially inactive. For example, in some embodiments the actuator (e.g., electric actuator including an electric motor) can lock during at least a portion of the stance phase, or alternatively during all or substantially all of the stance phase. Locking the actuator during the stance phase can allow the flexible members to flex and thus provide damping and energy absorption for storage during the stance phase. Thus, as discussed further herein, the spring can be loaded during stance by the force placed on the flexible members by the user, storing energy. The stored energy can then be released at toe-off. Further, in some embodiments the actuator can be unlocked and actuated (e.g., via the electric motor of the actuator) to plantarflex the foot plate during toe-off to push the foot forward at this point in the gait cycle. Notably, if the actuator is not locked during the stance phase, force between the prosthetic foot and the ground may be transmitted into a motion of the actuator, instead of a desirable bending of the flexible members. However, if reducing bending in the flexible members is desirable, the actuator can be allowed to provide some marginal movement. Similarly, bending in the flexible members can be increased by activating the actuator to bend the members (e.g., at toe off, during stance phase).

The prosthetic foot can detect a time to unlock the actuator and optionally actuate the actuator (e.g., via an electric motor) to provide powered plantarflexion (such as at toe-off) with various sensors. For example, a load sensor can detect a change in forces on the prosthetic foot consistent with the on-set of toe-off. Additionally or alternatively, a gyroscope can indicate an angle of the prosthetic foot relative to the ground or a path of motion of the angle of the foot relative to the ground, again being consistent with the on-set of toe-off. In further embodiments, the prosthetic foot can be adjustable, such that the timing of the unlocking of the actuator and optional powered plantarflexion can be adjusted. Further, the actuator (e.g., electric actuator with an electric motor) can stop providing powered plantarflexion before the end of toe-off, such that only the spring or flexible members provide push-off at the end of the toe-off to push the foot forward and into swing.

Similarly, the strength of the plantarflexion could also be adjustable. These adjustments can be made in a variety of ways, such as with various controls on the device, or a computer, mobile device, or other device wired or wirelessly communicating (e.g., via Rf or IR communication) with the prosthetic foot and having associated software such as an app. Further, the strength of the plantarflexion can be adjusted (e.g., automatically adjusted via an electronic controller) according to a speed of ambulation by the user.

Further, in some embodiments, locking of the actuator can depend on the terrain a user is walking-on. For example, if the prosthetic foot detects movement on a decline, the actuator can be configured to not lock, such that the actuator can provide power during stance phase to ease the descent. In another example, the actuator can be configured not to lock while moving on stairs such that a sufficient range of motion is available.

Additionally, in some embodiments, the prosthetic foot can include a stiffness control member that can be mechanically actuated (e.g., manually or automatically) to vary a stiffness of one or more flexible members of the prosthetic foot to provided different levels of stiffness (e.g., during different types of gait).

Testing has shown that the designs described herein can reduce the impact transmitted through a first connection portion 12 to approximately one-third that created in conventional prosthetic feet. This reduced impact can relieve stress on an amputee's stump or additional prosthetic devices connected to the prosthetic foot, such as a prosthetic knee.

Vacuum Socket Attachment

In some embodiments, various feet and/or ankle modules shown and described herein can be configured to be compatible with vacuum suspension systems. Such a system generates negative pressure within a prosthetic socket to improve the fit and stability of the socket relative to the residual limb. The distal end of the residual limb typically has more soft tissue compared to the area closer to the knee. The distal end is therefore more susceptible to volume fluctuations throughout the day, which can impede stabilization and suspension of the socket. A vacuum suspension system that can be used with the feet described herein can therefore apply a vacuum to the distal end of the residual limb to improve stability and suspension. The system can include a frame coupled to the foot and a membrane disposed on or between parts of the frame. When the user places weight on the heel of the foot, the membrane expands, which causes air to be drawn out of the socket to create and maintain the vacuum. Additional details regarding such systems are shown and described in U.S. Publications 2013/0289742, 2013/0289741, and 2013/0221544 and U.S. Design Patent Nos. D711,510 and D718,861, which are incorporated by reference herein in their entirety and should be considered a part of this specification.

Conditional language used herein, such as, among others, "can," "could," "might," "may," "e.g.," and from the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it may be understood that various omissions, substitutions, and changes in the form and details of the ground contact sensing system, including the sensor components, logical blocks, modules, and processes illustrated may be made without departing from the spirit of the disclosure. As may be recognized, certain embodiments of the systems described herein may be embodied within a form that does not provide all of the features and benefits set forth herein, as some features may be used or practiced separately from others. Additionally, features described in connection with one embodiment can be incorporated into another of the disclosed embodiments, even if not expressly discussed herein, and the prosthetic device having the combination of features still fall within the scope of the invention. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted roadly based on the language employed in the claims and not limited to the examples described in the present specification or during the prosecution of the application, which examples are to be construed as non-exclusive.

What is claimed is:

1. A prosthetic foot comprising:
   an adapter member comprising a connector configured to connect the adapter member to a user or another prosthetic device;
   a lower plate extending between a proximal end and a distal end;

a support member extending between and interconnecting the proximal end of the lower plate and a proximal portion of the adapter member, the support member pivotally coupled to the proximal end of the lower plate; and a top plate assembly extending between a proximal end and a distal end, the top plate assembly including a split that extends from the proximal end to the distal end to divide the top plate assembly into at least a medial blade and a lateral blade, a distal portion of the adapter member extending through and pivotally coupled to the medial and lateral blades at the proximal end of the top plate assembly to thereby facilitate a medial-lateral and/or a twist movement of the prosthetic foot during stance when the prosthetic foot is in contact with a support surface in a standing or walking position.

2. The prosthetic foot of claim 1, wherein the top plate assembly comprises a first plate and a second plate, the second plate disposed above the lower plate and the first plate disposed above the second plate, the first and second plates spaced apart from each other at least along a portion of their lengths, wherein a gap between the first and second plates widens at the proximal end of the top plate assembly to receive an axle pin therein that interconnects the top plate assembly and the distal portion of the adapter member.

3. The prosthetic foot of claim 1, wherein the support member has a fixed length.

4. The prosthetic foot of claim 1, wherein the support member comprises a mechanical actuator mechanically actuatable to adjust a length of the support member.

5. The prosthetic foot of claim 1, wherein the support member comprises a powered actuator that is actuatable to adjust a length of the support member.

6. The prosthetic foot of claim 1, further comprising a bottom plate extending between a heel end and a toe end, the bottom plate being disposed below the lower plate.

7. The prosthetic foot of claim 6, wherein the toe end of the bottom plate extends distally of the distal end of the lower plate.

8. The prosthetic foot of claim 6, wherein the distal end of the top plate assembly is generally aligned with the toe end of the bottom plate.

9. The prosthetic foot of claim 1, further comprising a spherical bearing disposed between and pivotally coupling the distal portion of the adapter member and the proximal end of the medial and lateral blades.

10. The prosthetic foot of claim 9, wherein the support member is pivotally coupled to the proximal end of the lower plate via a second spherical bearing.

11. A prosthetic foot comprising:
an adapter member comprising a connector configured to connect the adapter member to a user or another prosthetic device;
a lower plate extending between a proximal end and a distal end;
a support member extending between and interconnecting the proximal end of the lower plate and a proximal portion of the adapter member, the support member pivotally coupled to the proximal end of the lower plate;
a spherical bearing connected to a distal portion of the adapter member; and
a top plate extending between a proximal end and a distal end, the proximal end of the top plate curved in a C-shape and comprising an opening to receive the spherical bearing, the top plate being coupled to the spherical bearing at the proximal end of the top plate to thereby facilitate a medial-lateral and/or a twist movement of the prosthetic foot during stance when the prosthetic foot is in contact with a support surface in a standing or walking position.

12. The prosthetic foot of claim 11, wherein the top plate comprises a first plate and a second plate, the second plate disposed above the lower plate and the first plate disposed above the second plate, the first and second plates spaced apart from each other at least along a portion of their lengths, wherein a gap between the first and second plates widens at the proximal end of the top plate to receive an axle pin therein that interconnects the top plate and the spherical bearing.

13. The prosthetic foot of claim 11, wherein the support member comprises a mechanical actuator mechanically actuatable to adjust a length of the support member.

14. The prosthetic foot of claim 11, wherein the support member comprises a powered actuator that is actuatable to adjust a length of the support member.

15. The prosthetic foot of claim 11, further comprising a bottom plate extending between a heel end and a toe end, the bottom plate being disposed below the lower plate.

16. The prosthetic foot of claim 15, wherein the toe end of the bottom plate extends distally of the distal end of the lower plate.

17. The prosthetic foot of claim 15, wherein the top plate comprises a split that extends to the distal end of the top plate to divide the top plate into a medial portion and a lateral portion.

18. The prosthetic foot of claim 11, wherein the support member is pivotally coupled to the proximal end of the lower plate via a second spherical bearing.

19. A prosthetic foot comprising:
an adapter member comprising a connector configured to connect the adapter member to a user or another prosthetic device;
a lower plate extending between a proximal end and a distal end;
a support member extending between and interconnecting the proximal end of the lower plate and a proximal portion of the adapter member, the support member pivotally coupled to the proximal end of the lower plate; and
a top plate assembly extending between a proximal end and a distal end and including an elongated plate folded upon itself to define a first plate and a second plate, the second plate disposed above the lower plate and the first plate disposed above the second plate, the first and second plates spaced apart from each other at least a long a portion of their lengths, wherein a gap between the first and second plates widens at the proximal end of the top assembly to receive an axle pin therein that interconnects the top plate assembly and a distal portion of the adapter member, and wherein the axle pin is configured to extend through the first plate and the second plate and couple with the distal portion of the adaptor member, and wherein the top plate assembly comprises a split dividing the top plate assembly into a medial portion and a lateral portion,
wherein the distal portion of the adapter member is disposed between and pivotally coupled to the medial and lateral portions of the top blade assembly at the proximal end of the top plate assembly to thereby facilitate a medial-lateral and/or a twist movement of the prosthetic foot during stance when a bottom surface of the prosthetic foot is in contact with a support surface.

20. The prosthetic foot of claim 19, wherein support member comprises a mechanical actuator mechanically actuatable to adjust a length of the support member.

21. The prosthetic foot of claim 19, wherein the support member comprises a powered actuator that is actuatable to adjust a length of the support member.

22. The prosthetic foot of claim 19, further comprising a bottom plate extending between a heel end and a toe end, the bottom plate being disposed below the lower plate.

23. The prosthetic foot of claim 22, wherein the toe end of the bottom plate extends distally of the distal end of the lower plate.

24. The prosthetic foot of claim 19, wherein the split extends to the distal end of the top plate assembly.

25. The prosthetic foot of claim 24, further comprising a spherical bearing disposed between and pivotally coupling the distal portion of the adapter member and the proximal end of the medial and lateral blades.

\* \* \* \* \*